US011056232B2

(12) United States Patent
Avraham et al.

(10) Patent No.: US 11,056,232 B2
(45) Date of Patent: Jul. 6, 2021

(54) MEDICATION USAGE AUDITING BASED ON ANALYSIS OF INFUSION PUMP NETWORK TRAFFIC

(71) Applicant: Medigate tech Ltd., Tel-Aviv (IL)

(72) Inventors: Oran Avraham, Tel Aviv (IL); Yaakov Rubin, Tel Aviv (IL); Ben Mashiah, Haifa (IL); Itamar Cohen-Matalon, Omer (IL)

(73) Assignee: Medigate Tech Ltd., Tel-Aviv (IL)

( * ) Notice: Subject to any disclaimer, the term of this patent is extended or adjusted under 35 U.S.C. 154(b) by 81 days.

(21) Appl. No.: 16/543,570

(22) Filed: Aug. 18, 2019

(65) Prior Publication Data
US 2021/0050102 A1  Feb. 18, 2021

(51) Int. Cl.
*G16H 40/40* (2018.01)
*G16H 20/17* (2018.01)
(Continued)

(52) U.S. Cl.
CPC ............. *G16H 40/40* (2018.01); *G16H 20/17* (2018.01); *G16H 70/40* (2018.01); *H04L 69/22* (2013.01); *H04L 67/12* (2013.01)

(58) Field of Classification Search
CPC ........ G16H 40/40; G16H 20/17; G16H 70/40; H04L 67/12; H04L 69/22
(Continued)

(56) References Cited

U.S. PATENT DOCUMENTS 4,937,743 A    6/1990  Rassman et al.
5,088,981 A *  2/1992  Howson ................ A61M 5/172
                                              604/31
(Continued)

FOREIGN PATENT DOCUMENTS

WO    WO2006081041    8/2006
WO    WO2009023634    2/2009
WO    WO2018013666    1/2018

OTHER PUBLICATIONS

Jenny Knackmuß et al., "Security risk of medical devices in IT networks—the case of an infusion pump unit," Proceedings of SPIE—The International Society for Optical Engineering—Mar. 2015 (Year: 2015).*

(Continued)

*Primary Examiner* — Joshua B Blanchette
(74) *Attorney, Agent, or Firm* — Active Knowledge Ltd.

(57) ABSTRACT

This disclosure describes a system, a method, and a computer program that enable auditing reported amounts of infused medications at a medical facility. In one embodiment, a computer receives packets transmitted over a communication network, where the packets include data related to activity of infusion pump systems at the medical facility. The computer performs deep packet inspection (DPI) of the packets, and extracts, from results of the DPI, values that include dosages of medications delivered to patients during treatment sessions using the infusion pump systems. The computer calculates, based on the values, amounts of the medications that were provided to the patients during the treatment sessions (actual amounts). Additionally, the computer receives amounts of the medications reported as being provided to the patients during the treatment sessions (reported amounts). The computer forwards a result of a comparison between the actual amounts and the reported amounts.

20 Claims, 17 Drawing Sheets

(51) Int. Cl.
*G16H 70/40* (2018.01)
*H04L 29/06* (2006.01)
*H04L 29/08* (2006.01)

(58) Field of Classification Search
USPC ........................................................ 705/2, 3
See application file for complete search history.

(56) References Cited

U.S. PATENT DOCUMENTS

| | | | |
|---|---|---|---|
| 6,430,536 | B2 | 8/2002 | Irving et al. |
| 6,714,976 | B1 | 3/2004 | Wilson et al. |
| 6,738,798 | B1 | 5/2004 | Ploetz et al. |
| 6,751,630 | B1 | 6/2004 | Franks et al. |
| 6,839,753 | B2 | 1/2005 | Biondi et al. |
| 6,912,481 | B2 | 6/2005 | Breunissen et al. |
| 7,072,931 | B2 | 7/2006 | Goldhaber et al. |
| 7,411,946 | B2 | 8/2008 | Worrall et al. |
| 7,698,156 | B2 | 4/2010 | Martucci et al. |
| 8,036,925 | B2 | 10/2011 | Choubey |
| 8,038,593 | B2 | 10/2011 | Friedman et al. |
| 8,095,692 | B2 | 1/2012 | Mehta et al. |
| 8,334,768 | B2 | 12/2012 | Eaton et al. |
| 8,348,885 | B2 | 1/2013 | Moberg et al. |
| 8,799,009 | B2 | 8/2014 | Mellin et al. |
| 9,027,079 | B2 | 5/2015 | Comay et al. |
| 9,621,432 | B2 | 4/2017 | Gonzalez et al. |
| 9,971,871 | B2 | 5/2018 | Arrizza et al. |
| 10,049,346 | B2 | 8/2018 | Jensen et al. |
| 10,135,849 | B2 | 11/2018 | Jha et al. |
| 10,204,211 | B2 | 2/2019 | Hammerle et al. |
| 10,212,178 | B2 | 2/2019 | Cheng et al. |
| 10,242,060 | B2 | 3/2019 | Butler et al. |
| 2005/0055242 | A1 | 3/2005 | Bello et al. |
| 2005/0103354 | A1 | 5/2005 | Miyauchi et al. |
| 2008/0046286 | A1 | 2/2008 | Halsted |
| 2008/0094207 | A1 | 4/2008 | Collins et al. |
| 2008/0255880 | A1 | 10/2008 | Beller et al. |
| 2009/0099867 | A1 | 4/2009 | Newman |
| 2009/0112630 | A1 | 4/2009 | Collins et al. |
| 2009/0150484 | A1 | 6/2009 | Roberts |
| 2009/0228330 | A1 | 9/2009 | Karras et al. |
| 2009/0281867 | A1 | 11/2009 | Sievenpiper et al. |
| 2010/0313009 | A1* | 12/2010 | Combet ............. G06Q 30/0204 713/150 |
| 2011/0316701 | A1* | 12/2011 | Alper .................. G08B 21/245 340/573.1 |
| 2012/0011253 | A1 | 1/2012 | Friedman et al. |
| 2012/0072238 | A1 | 3/2012 | Collins et al. |
| 2013/0031237 | A1 | 1/2013 | Talbert |
| 2013/0087609 | A1 | 4/2013 | Nichol et al. |
| 2014/0129248 | A1 | 5/2014 | Zuehlsdorff et al. |
| 2014/0207371 | A1 | 7/2014 | Johnson |
| 2014/0266790 | A1 | 9/2014 | Al-Ali et al. |
| 2014/0317228 | A1 | 10/2014 | Dharmasanam |
| 2015/0116126 | A1 | 4/2015 | Hyde et al. |
| 2015/0154364 | A1* | 6/2015 | Biasi ....................... H04L 67/12 709/223 |
| 2015/0178451 | A1 | 6/2015 | Wallace et al. |
| 2015/0234995 | A1 | 8/2015 | Casady et al. |
| 2015/0339445 | A1 | 11/2015 | Gruby et al. |
| 2016/0034655 | A1 | 2/2016 | Gray et al. |
| 2016/0212099 | A1 | 7/2016 | Zou et al. |
| 2016/0294951 | A1 | 10/2016 | Durrant et al. |
| 2017/0024520 | A1 | 1/2017 | Michon et al. |
| 2017/0136176 | A1* | 5/2017 | Gray ..................... G16H 20/17 |
| 2018/0113765 | A1 | 4/2018 | Ukis et al. |
| 2018/0144139 | A1 | 5/2018 | Cheng et al. |
| 2018/0225960 | A1 | 8/2018 | Al-Ali et al. |
| 2018/0270229 | A1 | 9/2018 | Zhang et al. |
| 2019/0014137 | A1 | 1/2019 | Du et al. |
| 2019/0065681 | A1 | 2/2019 | Gmeiner |
| 2019/0098028 | A1 | 3/2019 | Ektare et al. |
| 2019/0130075 | A1* | 5/2019 | Henein ................. G06F 21/577 |
| 2019/0167902 | A1* | 6/2019 | Kamen .................. G16H 10/65 |

OTHER PUBLICATIONS

Antonello, Rafael, et al. "Deep packet inspection tools and techniques in commodity platforms: Challenges and trends." Journal of Network and Computer Applications 35.6 (2012): 1863-1878.

Catlin, Ann Christine, et al. "Comparative analytics of infusion pump data across multiple hospital systems." American Journal of Health-System Pharmacy 72.4 (2015): 317-324.

Ferreira, Ricardo Jorge Teixeira, et al. "Data Quality in HL7 Messages—A Real Case Analysis." 2015 IEEE 28th International Symposium on Computer-Based Medical Systems. IEEE, 2015.

Hoh et al., "Building a Smart Infusion System Drug Library", Jan. 30, 2017. Downloaded from https://www.ismp.org/resources/building-smart-infusion-library.

Lehr, Jennifer, et al. "Achieving outcomes with innovative smart pump technology: partnership, planning, and quality improvement." Journal of nursing care quality 34.1 (2019): 9.

O'Brien, Gavin, et al. Securing Wireless Infusion Pumps in Healthcare Delivery Organizations. No. NIST Special Publication (SP) 1800-8 (Draft). National Institute of Standards and Technology, 2017.

Oliveira, Raphael, et al. "Open-source based integration solution for hospitals." 2016 IEEE 29th International Symposium on Computer-Based Medical Systems (CBMS). IEEE, 2016.

Paessler, "Healthcare IT—a monitoring primer", Feb. 2019, downloaded Mar. 14, 2019 from https://go.paessler.com/hubfs/content/whitepaper/healthcare-it.pdf.

Saint Francis Medical Center, Case Study: "Midwestern Hospital Transforms Infusion Pump Management, Drives Higher Quality, Efficiency and Performance". Downloaded Apr. 16, 2019, from: https://www.bd.com/documents/case-studies/infusion/MMS_IF_DOC-12-85054-AB_Saint-Francis-Asset-Mgmt-Case-Study-BD-Final-BCCR_CS_EN.pdf.

Svoboda, Jakub, Ibrahim Ghafir, and Vaclav Prenosil. "Network monitoring approaches: An overview." Int J Adv Comput Netw Secur 5.2 (2015): 88-93.

Wood, Daniel, Noah Apthorpe, and Nick Feamster. "Cleartext data transmissions in consumer iot medical devices." Proceedings of the 2017 Workshop on Internet of Things Security and Privacy. ACM, 2017.

* cited by examiner

Recommended Device:
Infusion pump 1202, Utilization: Low
Location: Room 606b

Other devices:
Infusion pump 1204, Utilization: High
Location: Room 501a

⋮

154

Recommended Location Switch:

Infusion pump 1202, Utilization: Low
Location: Room 606b

↕

Infusion pump 1204, Utilization: High
Location: Room 501a

156

MEDICATION USAGE AUDITING BASED ON ANALYSIS OF INFUSION PUMP NETWORK TRAFFIC

BACKGROUND

Medical facilities often have large inventories of medications that are used to treat patients with infusion pump systems. Keeping track of such inventories is a necessary, but somewhat challenging task. In particular, it can be difficult to identify irregularities in reported medication utilization that may arise to cover excessive inventory shrinkage (e.g., due to various reason such as improper storage, misuse of medications, and even theft). Because it is often difficult to keep track of exact dosages of medications used for treatments, it can be difficult to compare quantities of medications that are reported as being utilized with records of actual use. Thus, there is a need for a way to audit reported amounts of infused medications.

SUMMARY

Described herein are embodiments of a system, method, and computer-readable media storing computer programs, which audit reported amounts of infused medications. Embodiments described herein utilize data collected from monitoring packets that include data related to activity of infusion pump systems, which are transmitted over a communication network of a medical facility, in order to keep track of actual amounts of medications utilized in treatments using the infusion pump systems. In one embodiment, the actual amounts are compared with amounts of the medications reported as being provided to the patients during the treatment sessions. For example, the reported amounts may be based on changes in amounts of the medications in an inventory of the medical facility. A large difference between the actual and reported amounts can be an indication of irregular and/or excessive inventory shrinkage.

Various embodiments described herein involve capturing and/or analyzing packets that include data related to activity and/or operation of medical devices, which are transmitted over a communication network of a medical facility through the routine operation of the medical devices. In some embodiments, the packets are captured using a mirror port on a networking device (e.g., a switch) that is connected to the communication network. Analysis of this data may involve performing deep packet inspection (DPI) of the packets, in order to learn various properties about the medical devices at the medical facility, such as identifying what types of devices were used to generate packets, protocols used to transmit the packets, and/or standards with which the packets comply (e.g., HL7, DICOM, or some proprietary standard). Additionally, the DPI may involve extracting information from data payloads of captured packets.

It is to be noted that the reliance on capturing transmitted packets, as opposed to communicating directly with the medical devices and/or with an electronic medical records (EMR) system has various advantages. In addition to not interfering with operations of existing systems, the fact that data is captured rather than specifically sent for the purpose of the claimed invention, means that aspects of the claimed invention may be implemented with legacy medical devices and EMR systems, which might have not been designed or programmed for the purpose of the claimed invention. For example, the claimed invention may be implemented with network connected infusion pumps, which have not been designed to provide information for the purpose of auditing medication usage based on analysis of infusion pump network traffic.

One aspect of this disclosure involves a system configured to audit reported amounts of infused medications. In one embodiment, the system includes a computer that receives packets transmitted over a communication network, where the packets include data related to activity of infusion pump systems. The computer performs deep packet inspection (DPI) of the packets, and extracts, from results of the DPI, values that include dosages of medications delivered to patients during treatment sessions using the infusion pump systems. The computer calculates, based on the values, amounts of the medications that were provided to the patients during the treatment sessions (referred to as "actual amounts"). Additionally, the computer receives amounts of the medications reported as being provided to the patients during the treatment sessions (referred to as "reported amounts"). The computer forwards a result of a comparison between the actual amounts and the reported amounts.

In one embodiment, the computer receives additional packets that were transmitted over communication networks of multiple medical facilities, where the additional packets comprise data related to activity of additional infusion pump systems. The computer performs DPI of the additional packets, and extracts, from results of the DPI of the additional packets, additional values that include dosages of medications delivered to additional patients during additional treatment sessions using the additional infusion pump systems. The computer calculates, based on the additional values, amounts of the medications that were provided to the additional patients during the additional treatment sessions (additional actual amounts). The computer also receives amounts of the medications reported as being provided to the patients during the additional treatment sessions (additional reported amounts). The computer reports a comparison between (i) a magnitude of a difference between the actual amounts and the reported amounts, and (ii) magnitudes of differences between the additional actual amounts and the additional reported amounts. Optionally, the computer reports a comparison between (i) a magnitude of a difference between the actual amounts and the reported amounts for a certain care area and (ii) magnitudes of differences between the additional actual amounts and the additional reported amounts for the certain care area at the multiple medical facilities.

In another embodiment, the computer receives additional packets that were transmitted over communication networks of multiple medical facilities, where the additional packets comprise data related to activity of additional infusion pump systems. The computer performs DPI of the additional packets, and extracts, from results of the DPI of the additional packets, additional values that include dosages of a certain medication delivered to additional patients during additional treatment sessions using the additional infusion pump systems. The computer calculates, based on the additional values, amounts of the certain medication that were provided to the additional patients during the additional treatment sessions (additional actual amounts). The computer also receives amounts of the medications reported as being provided to the patients during the additional treatment sessions (additional reported amounts). The computer reports a comparison between (i) a magnitude of a difference between an amount of the certain medication provided to the patients during the treatment sessions and an amount of the certain medication reported as being provided to the patients during the treatment sessions, and (ii) magnitudes of differences between the additional actual amounts and the additional reported amounts.

In one embodiment, the computer calculates the reported amounts based on indications of changes in amounts of the medications in an inventory of the medical facility, which were received from a computer system having access to state information of said inventory.

In one embodiment, the computer extracts, from the results of the DPI, indications of care areas at which the treatments sessions were conducted, and calculates, based on the values and the indications, amounts of the medications that were provided to patients during the treatment sessions at each of the care areas (actual care area amounts). The computer also receives amounts of the medications reported as being provided to the patients during the treatment sessions in each care area (reported care area amounts). The computer forwards a result of a comparison between the actual care area amounts and the reported care area amounts.

In another embodiment, the computer extracts, from the results of the DPI, identities of caregivers that administered the treatment sessions, and calculates, based on the values and the identities, amounts of the medications that were provided to patients during the treatment sessions by each of the caregivers (actual caregiver amounts). The computer also receives amounts of the medications reported as being provided to the patients during the treatment sessions administered by each of the caregivers (reported caregiver amounts). The computer forwards a result of a comparison between the actual caregiver amounts and the reported caregiver amounts.

In one embodiment, the communication network includes a networking device that has a mirror port that is configured to duplicate the packets, which are transmitted over the communication network. The computer is connected to the mirror port and is configured to receive the packets via the mirror port.

In one embodiment, the computer does not have access to an EMR system to which at least some of the packets are sent. Additionally or alternatively, the computer may not have permission to access and/or command any of the infusion pump systems. Additionally or alternatively, the computer may not transmit packets over the communication network. Additionally or alternatively, the computer may be connected to a single networking device that is connected to the communication network.

Another aspect of this disclosure involves a method for auditing reported amounts of infused medications. In one embodiment, the method involves the following steps: capturing packets transmitted over a communication network, where the packets comprise data related to operation of infusion pump systems at a medical facility; performing deep packet inspection (DPI) of the packets; extracting, from results of the DPI, values that include dosages of medications delivered to patients during treatment sessions using the infusion pump systems; calculating, based on the values, amounts of the medications that were provided to the patients during the treatment sessions (actual amounts); receiving amounts of the medications reported as being provided to the patients during the treatment sessions (reported amounts); and forwarding a result of a comparison between the actual amounts and the reported amounts.

In one embodiment, the method optionally includes the following steps: extracting, from the results of the DPI, indications of care areas at which the treatments sessions were conducted; calculating, based on the values and the indications, amounts of the medications that were provided to patients during the treatment sessions at each of the care areas (actual care area amounts); receiving amounts of the medications reported as being provided to the patients during the treatment sessions in each care area (reported care area amounts); and forwarding a result of a comparison between the actual care area amounts and the reported care area amounts.

In one embodiment, the method optionally includes the following steps: extracting, from the results of the DPI, identities of caregivers that administered the treatment sessions; calculating, based on the values and the identities, amounts of the medications that were provided to patients during the treatment sessions by each of the caregivers (actual caregiver amounts); receiving amounts of the medications reported as being provided to the patients during the treatment sessions administered by each of the caregivers (reported caregiver amounts); and forwarding a result of a comparison between the actual caregiver amounts and the reported caregiver amounts.

In one embodiment, the method optionally includes the following steps: capturing additional packets transmitted over communication networks of multiple medical facilities, wherein the additional packets comprise data related to activity of additional infusion pump systems; performing DPI of the additional packets; extracting, from results of the DPI of the additional packets, additional values comprising dosages of medications delivered to additional patients during additional treatment sessions using the additional infusion pump systems; calculating, based on the additional values, amounts of the medications that were provided to the additional patients during the additional treatment sessions (additional actual amounts); receiving amounts of the medications reported as being provided to the patients during the additional treatment sessions (additional reported amounts); and reporting a comparison between (i) a magnitude of a difference between the actual amounts and the reported amounts and (ii) magnitudes of differences between the additional actual amounts and the additional reported amounts.

In one embodiment, the method optionally includes the following steps: capturing additional packets transmitted over communication networks of multiple medical facilities, wherein the additional packets comprise data related to activity of additional infusion pump systems; performing DPI of the additional packets; extracting, from results of the DPI of the additional packets, additional values comprising dosages of a certain medication delivered to additional patients during additional treatment sessions using the additional infusion pump systems; calculating, based on the additional values, amounts of the certain medication that were provided to the additional patients during the additional treatment sessions (additional actual amounts); receiving amounts of the medications reported as being provided to the patients during the additional treatment sessions (additional reported amounts); and reporting a comparison between (i) a magnitude of a difference between amount of the certain medication provided to the patients during the treatment sessions and amount of the certain medication reported as being provided to the patients during the treatment sessions, and (ii) magnitudes of differences between the additional actual amounts and the additional reported amounts.

In one embodiment, the method optionally includes a step of calculating the reported amounts based on indications of changes in amounts of the medications in an inventory of the medical facility, which were received from a computer system having access to state information of said inventory.

In one embodiment, the method optionally includes a step of receiving at least some of the packets utilizing port mirroring of a port on a networking device connected to a communication network.

Yet another aspect of this disclosure involves a non-transitory computer-readable medium having instructions stored thereon that, in response to execution by a system including a processor and memory, causes the system to perform operations that include: capturing packets transmitted over a communication network, where the packets comprise data related to operation of infusion pump systems at a medical facility; performing deep packet inspection (DPI) of the packets; extracting, from results of the DPI, values comprising dosages of medications delivered to patients during treatment sessions using the infusion pump systems; calculating, based on the values, amounts of the medications that were provided to the patients during the treatment sessions (actual amounts); receiving amounts of the medications reported as being provided to the patients during the treatment sessions (reported amounts); and forwarding a result of a comparison between the actual amounts and the reported amounts.

BRIEF DESCRIPTION OF THE DRAWINGS

The embodiments are herein described by way of example only, with reference to the following drawings.

DETAILED DESCRIPTION

Figure 1:
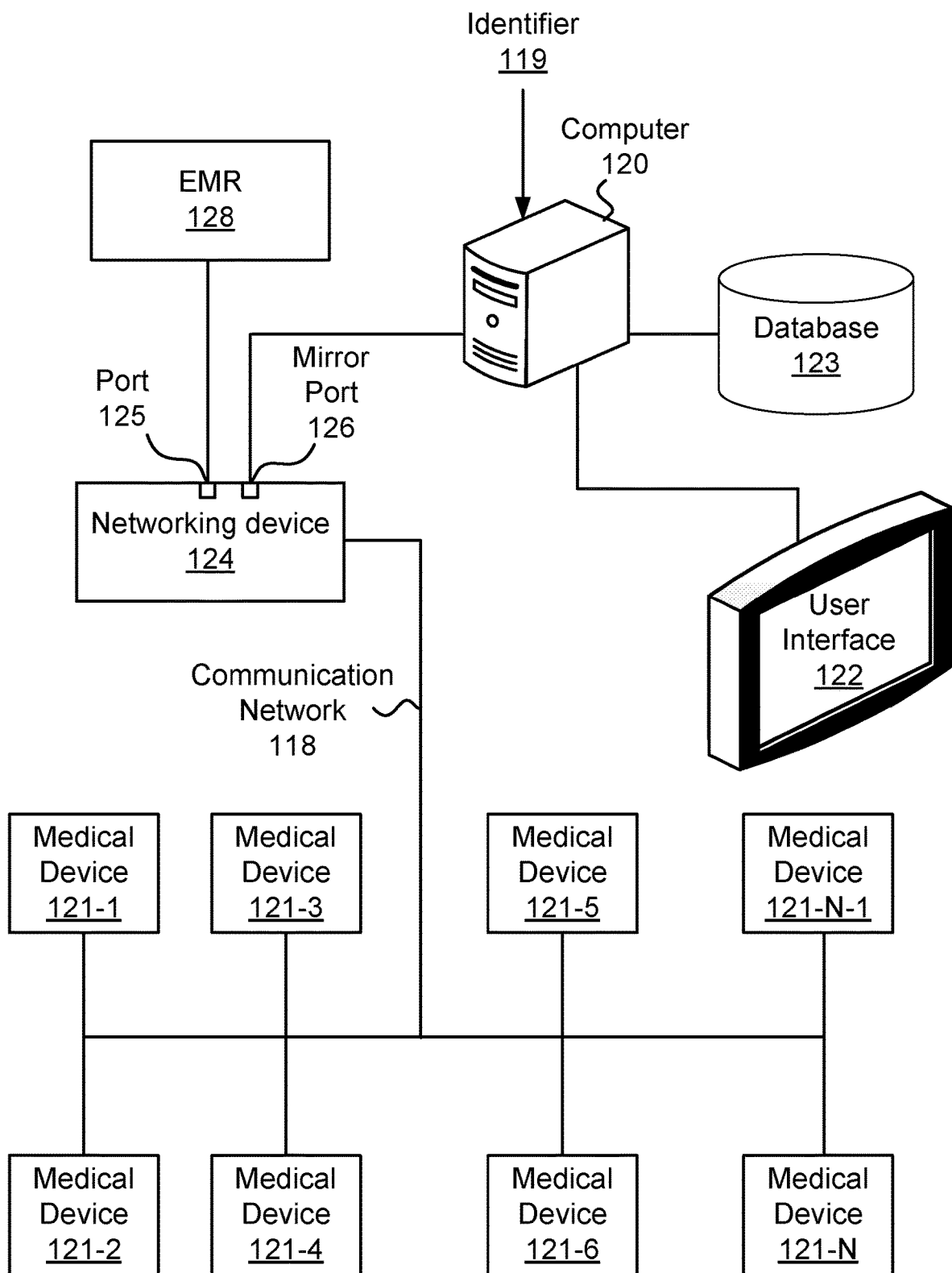
FIG. 1 illustrates one embodiment of a system configured to notify about availability of a medical device that is intended to receive maintenance.

Herein, a "medical device" refers to a device that is utilized in the treatment of a person (also referred to as a patient). Medical devices may be found in a medical facility, such as a hospital, clinic, convalescence home, or nursing home. Some examples of medical devices include an infusion pump system, a patient-controlled analgesia (PCA) system, a patient (vital signs) monitor (e.g., an $SpO_2$ sensor, an $EtCO_2$ sensor, a cardiac output monitor, a gastric tonometer, etc.), a Radiology or Radiotherapy device (CT, X-RAY, MRI, PET, ultrasound, C-Arm), a bedside blood analyzer (e.g. blood glucose), an Auto-ID module (barcode scanner, RFID reader), and other devices which may measure physiological parameters and/or assist with the clinical care of a patient. Medical devices referred to in this disclosure are typically connected to a communication network via a wired connection and/or a wireless connection, and can send and/or receive packets of transmitted data.

Infusion pump systems (also referred to as "infusion pumps", "smart pumps", or the like) may refer to a variety of devices, which can include, but are not limited to, peristaltic pumps and syringe pumps. Infusion pump systems can generally be used to infuse fluids that may include drugs, medicaments (e.g., antibiotics, blood clotting agents, and analgesics), nutrients, blood, and/or other substances, into a patient's circulatory system. Infusion pump systems can infuse fluids into the body of a patient utilizing any of several routes such as, for example, intravenously, subcutaneously, arterially, or epidurally. Infusions can be delivered according to various delivery profiles, such as continuous, intermittent, or patient controlled.

In some embodiments, an infusion pump system may include a "control unit" (or "control module") and one or more "pump modules" that are each capable of infusing a separate fluid into the patient. Thus, a patient may simultaneously be infused with more than one fluid. Optionally, the control unit may be connected to a communication network of a medical facility, and transmit data (e.g., to an EMR), while the pump modules may not be connected to said communication network. Optionally, the pump modules may be connected to the control unit via a separate, dedicated network that is not the communication network of the medical facility.

Herein, statements about a medical device that "is utilized to treat a patient" or a medical device that "is utilized in the treatment of the patient", or similar language, may refer to the medical device being used directly to treat the patient, or in an indirect manner that supports the treatment of the patient. For example, an infusion pump system that provides medication may be considered to be used directly to treat the patient, while a patient monitor may be considered, in some cases, to be used indirectly in the treatment of the patient.

Data transmitted to and/or from medical devices over a communication network of a medical facility can involve communications exchanged between the medical devices and various computer systems of the medical facility, such as electronic medical record (EMR) systems or electronic health record (EHR) systems (the terms EMR and EHR are used herein interchangeably). As used herein, an EMR system stores health information related to patients (e.g., symptoms, test results, and prescribed treatments), including information originating from medical devices utilized to treat patients and/or information intended for the medical devices. Records stored on an EMR may be shared through network-connected, enterprise-wide information systems, or other information networks and exchanges.

As used herein a "communication network" (may also be referred to as a "computer network" or simply a "network") facilitates communication between various devices, such as medical devices, networking devices, and/or other electronic devices. A communication network includes one or more links between the devices, which are used to enable communication among the devices connected to the communication network. Some examples of devices that may be connected to a communication network include routers, switches, mobile access points, bridges, hubs, intrusion detection devices, storage devices, standalone server devices, blade server devices, sensors, desktop computers, firewall devices, laptop computers, handheld computers, tablet computers, smartphones, various medical devices described herein, and other types of computing devices. In various embodiments, a communication network may include various types of links (e.g., wired and/or wireless links). Furthermore, in various embodiments, a communication network may be implemented at various scales. For example, a communication network may be implemented as one or more local area networks (LANs), metropolitan area networks, subnets, wide area networks (such as the Internet), or can be implemented at another scale.

The term "networking device", as used herein, refers to a device that enables the transfer of data in a communication network, such as, but not limited to, a switch, a gateway, a router, a bridge, a hub, a daisy-chain device, and/or a repeater.

Packets comprising data may be exchanged among various devices (e.g., networking devices and/or medical devices) connected to a communication network over links using various predefined network communication protocols. Some examples of protocols include the Transmission Control Protocol/Internet Protocol (TCP/IP), User Datagram Protocol (UDP), Asynchronous Transfer Mode (ATM) protocol, Frame Relay protocol, or any other suitable protocol.

Various embodiments described herein involve capturing and/or analyzing packets that include data related to activity of medical devices; such packets may also be referred to as "data related to medical device activity", or using some other similar language. In some embodiments, the packets may be referred to as including data related to activity of a specific type of medical device, such as infusion pump systems or medical imaging devices. Examples of what constitutes packets related to activity of medical devices include packets sent by medical devices, packets sent to medical devices, packets that include parameters and/or instructions for operating medical devices, and packets that include data generated by medical devices. Optionally, at least some of the packets related to activity of medical devices may be compliant with a standard that is utilized in the healthcare filed, such as the Health Level Seven (HL7) standard, the Digital Imaging and Communications in Medicine (DICOM) standard, the Integrating the Healthcare Enterprise (IHE) standard, and/or some other standard that is utilized in the healthcare field. Additionally or alternatively, at least some of the packets related activity of medical devices may be compliant with a proprietary standard used by a certain vendor and/or manufacturer.

Various embodiments described herein involve receiving packets transmitted over a communication network. These packets may be considered "captured" (or "sniffed") from the network traffic. Capturing packets can be done using various techniques known in the art. One approach that may be used involves port mirroring, which is a method often used for monitoring network traffic. With port mirroring enabled, a networking device, such as a switch, sends a copy of all network packets seen on one port (or an entire VLAN) to another port, where the packets can be analyzed. Port mirroring is known in the art by several names. For example, port mirroring on a Cisco Systems switch is generally referred to as Switched Port Analyzer (SPAN) or Remote Switched Port Analyzer (RSPAN), and on 3Com switches port mirroring may be referred to as Roving Analysis Port (RAP). Other vendors may use other names for port mirroring.

Some embodiments may utilize other approaches in addition to, or instead of, port mirroring in order to capture packets. In some embodiments, packets may be captured utilizing a network TAP (Terminal Access Point). A Network TAP denotes a system that monitors events on a local network, which typically includes a dedicated hardware device that provides a way to access the data flowing across the local network. Another approach that may be utilized to capture packets in some embodiments is to enable promiscuous mode on a monitoring host (e.g., a server) that is connected to the communication network. And still another approach that may be utilized in some embodiments involves deployment of software plug-ins at servers and/or medical devices connected to the communication network to monitor their communications and transmit this data to a server for further analysis.

Some embodiments described herein may utilize an approach referred to as deep packet inspection (DPI) in order to analyze data contained in packets that are transmitted over a communication network. In general, DPI refers to analysis that involves inspecting the payload of a packet, which may carry control data, regular data, or any other type of information. DPI may also involve inspecting packet header information and/or other data utilized to route the packet. Optionally, DPI may be used to retrieve the content of the packets, which is typically not captured by administrative tools that capture metrics regarding traffic/application flows. Optionally, as part of the analysis, DPI of packets may involve identifying what types of devices were used to generate packets, protocols used to transmit the packets, and/or standards with which the packets comply (e.g., HL7, DICOM, or some proprietary standard), and utilizing this information in order to infer a specific structure and/or format for the data payload of the packets.

Results obtained from DPI of one or more packets may include various types of information. In some embodiments, results of DPI of one or more packets include information that is not included in headers of the one or more packets, and/or information that is not utilized for routing the one or more packets in the communication network. In some embodiments, results of DPI of one or more packets include information that cannot be inferred from headers and/or other routing information of the one or more packets.

Results obtained from DPI of one or more packets may include, in some examples, information that may be obtained from a single packet from among the one or more packets, such as an identifier of a medical device, a location of a medical device, one or more operating parameters of the medical device, or an identifier of a patient being treated utilizing the medical device. In other examples, results obtained from DPI of multiple packets may include information that is based on data from the multiple packets (and which may not be available from a single packet). For example, in some scenarios, determining the duration of a treatment session may involve inspecting the multiple packets to receive indications of when a patient was connected, and then later disconnected, from a medical device.

Various types of values may be used as "an identifier of a medical device" in embodiments described herein. The following are examples of types of values that may be utilized separately, or be combined, in order to produce an identifier of a medical device. In one example, an identifier of a medical device may be, or include, a serial number of the medical device (e.g., as provided by the manufacturer). In another example, an identifier of a medical device may be, or include, a name of the type or model of the medical device. In yet another example, an identifier of a medical device may be, or include, a name provided to the medical device by technical personnel (e.g., by IT personnel or a biomedical engineer at a medical facility). For example, the name may be "ICU MRI machine" OR "internal medicine patient monitor 18". In still another example, an identifier of a medical device may include an address or identifier of a networking device to which the medical device is connected and/or an address or identifier of a physical network connection (e.g., a network wall jack) to which the medical device is connected. In yet another example, an identifier of a medical device may include a physical address of a location at which the medical device is located (e.g., a floor number and/or a room number).

Data extracted from results of DPI of packets, may be stored, in some embodiments, in a database. Optionally, the database may include status information for one or more medical devices. Examples of status information of a medical device may include one or more of the following: an indication whether the medical device is being utilized to treat a patient, a location of the medical device, an identifier of a patient treated utilizing the medical device, an identifier of a staff member operating the medical device, information related to a treatment session with the medical device (e.g., start time, end time, operating parameters), and more.

Herein, the term "database" is used broadly to include any known or convenient means for storing data, whether centralized or distributed, relational or otherwise. Some examples of databases include a flat file stored on a file system, a hash table or array stored in a memory of a computer, a cloud-based data repository, and an SQL database. In particular, a reference to a database being accessed by a computer may correspond to a processor of the computer accessing memory residing in the computer.

It is to be noted that analysis of packets (e.g., utilizing DPI) can be a continuous process in various embodiments described herein. For example, a packet sent at a first time may indicate that a treatment of a certain patient has begun utilizing a specific medical device. Analysis of results of DPI of that packet can reveal this information, and the status of the specific medical device can be updated accordingly (e.g., in a database). Over the course of the treatment session, the specific medical device may transmit and/or receive additional packets that may be captured and analyzed using DPI. At a second time, somewhat after the first time, another packet may indicate that the patient is no longer being treated, or that the treatment is near it end (or has already ended). For example, a packet sent at the second time may indicate that the specific medical device is in an idle state, and not actively being used to provide treatment. Thus, in some embodiments, the database can provide a snapshot, at any given time, indicating the current status of medical devices connected to a communication network, according to analysis of network traffic that includes packets transmitted over the communication network. Optionally, the database can be accessed to provide an indication for each of the medical devices of whether it is being utilized to treat a patient. Additionally or alternatively, the database may be accessed to determine when a treatment session with a specific medical device started, and/or when a treatment session with a specific medical device is expected to end.

The extent of data transmitted over a communication network of a medical facility, which is captured and/or analyzed, may vary between embodiments disclosed herein. In some embodiments, essentially all packets transmitted over the communication network are captured (e.g., using a mirror port on a networking device which mirrors a port through which all the packets pass). Optionally, all captured packets are analyzed through DPI. In some embodiments, one or more filtering criteria may be employed to determine which of the packets are to be captured and/or analyzed using DPI. For example, filtering can select packets sent from and/or addressed to specific network addresses, packets sent using a specific protocol, and/or packets having specific characteristics (e.g., size, frequency of transmission, etc.).

In some embodiments, results obtained from DPI of one or more packets are utilized to determine whether a medical device was being used to treat a patient (at a certain time). Making such a determination can be done in various ways. In one embodiment, the one or more packets may include data fields that indicate a mode of operation of the medical device and/or an identifier of a patient with which the medical device is associated. This information can be used to determine that at the time the one or more packets were being sent, the medical device was being utilized to treat a patient. In another embodiment, characteristics of transmission of the packets can indicate whether a medical device is being utilized. For example, when a medical device is being utilized to treat a patient, one or more of the following may be observed: (i) the medical device may transmit and/or receive packets using a certain protocol (which typically not used when the medical device is not utilized to treat a patient); (ii) the medical device may transmit and/or receive packets at a certain frequency (which is typically higher when the medical device is not being utilized); and/or (iii) the medical device may transmit and/or receive a higher volume of data when being utilized, compared to times when it is not being utilized to treat patients.

Given the mobile nature of some types of medical devices (e.g., infusion pumps and patient monitors), it may be difficult to locate the medical devices since they can get moved around quite often, as the need arises. This can make obtaining a system-wide view of medical devices in a medical facility challenging, which can be problematic for efficient running of the medical facility. For example, a problem medical personnel encounter quite frequently is how to locate an available medical device; they can spend a lot of time scanning the rooms and corridors looking for a device that is not being utilized to treat patients. A similar problem arises when medical devices need to be serviced (e.g., for preventative maintenance), and technical staff spend a lot of time trying to locate those devices.

Some embodiments described in this disclosure utilize results of the DPI of packets to determine the location of medical devices. Obtaining location of medical devices may be done in various ways.

In some embodiments, a medical device may report its location in data it transmits. For example, packets sent by the medical device may include a location field in the data payload. Optionally, this value may be configurable. For example, when installing the device a technician may set its location, such as designating a care area in which it is located. In another example, the location may be a value that may be entered each time the medical device is used (or a previous entered location may be used as a default). As discussed above, various types of values may be used to designate a location. For example, a location of a medical device may include one or more of the following values: a building address, a name of a care area (e.g., ICU, pediatrics, dialysis, etc.), a floor number, a room number, or a bed number.

In other embodiments, a location of a medical device may be determined based on an address of a physical network connection point to which the medical device is connected. Optionally, the address of the physical network connection point is obtained from routing information of a packet. Additionally or alternatively, the address of the physical network connection point may be obtained from information of a data payload of a packet. Optionally, the address of the physical network connection point may be provided by identifying a certain network wall jack or a certain networking device to which the medical device is connected via a wire (e.g., a switch, hub, or router). By knowing the name/location of the physical network connection point, one can deduce the location of the medical device since it is likely to be nearby and connected via a wire to the network connection point. Examples of values that may be used as addresses of the physical network connection point include media access control (MAC) addresses and/or a networking device serial numbers. Optionally, location and/or identifier of the networking device can be converted to a physical location (e.g., room number) via a mapping of MAC addresses and/or networking devices to their actual locations in a medical facility (e.g., as recorded by IT personnel when setting up the networking infrastructure at a medical facility).

In yet other embodiments, a location of a medical device may be determined based on an address of a wireless access point (e.g., a WiFi access point) with which the medical device is connected. Optionally, the address of the wireless access point is obtained from routing information of a packet. Additionally or alternatively, the address of the wireless access point may be obtained from information of a data payload of a packet. Optionally, the address of the wireless access point may be a MAC address of the access point or an identifier of the access point, such as a base station identifier (BSSID), or a name of the access point (ESSID). The address of the wireless access point can be used to determine an approximate location of the medical device. Optionally, the approximate location may be estimated based on the fact that connecting to a certain access point typically means that a medical device is not far from the access point (e.g., within 100 feet or less), otherwise due to the wide spread of access points, the medical device would connect to a different access point that provides a stronger wireless signal.

Some embodiments described herein may be realized in a manner that does not interfere with the operations of existing systems at a medical facility (such as networking and electronic health records systems). Thus, adding an embodiment to a medical facility's computer system, or removing it therefrom, requires very little, if any changes to be done to the existing systems at the medical facility. Often this will result in there being no interruption to operations of the existing computer systems and the medical facility (which are typically mission critical systems). In particular, embodiments described herein may utilize a computer that does not even have access to computer systems of the medical facility, such as an EMR of the medical facility.

It is to be noted that the reliance of many of the embodiments described herein on capturing transmitted packets, as opposed to communicating directly with medical devices and/or with an EMR system, has various advantages. In addition to not interfering with operations of existing systems, the fact that data is captured rather than specifically sent for the purpose of being utilized by embodiments described herein, means that aspects of the inventions described herein may be implemented with legacy medical devices and EMR systems, which might have not been designed or programmed for the purpose performed by the embodiments of the inventions. For example, some embodiments may be implemented with network connected infusion pumps, patient monitors, or medical imaging devices, which have not been designed to provide information for the purpose of the various services provided in embodiments described herein.

Thus, in some embodiments, packets captured and utilized for analysis (e.g., by performing DPI of the packets and utilizing the results) are not transmitted in response to a query to an EMR system by a computer that performs the analysis. Optionally, these packets are not transmitted in response to a communication sent by said computer. Optionally, the computer that utilizes the results of DPI of the packets may not have access to an EMR system to which at least some of the packets are sent. Additionally or alternatively, the computer that analyzes results of the DPI of the packets may not have permission to access data stored on the medical devices and/or to command the medical devices to perform any operations.

In some embodiments described herein a computer that analyzes results of the DPI of packets (to realize the inventions described herein) is separate from the existing networking and computer systems of a medical facility at which it is installed (possibly with the exception of having a connection via a mirror port, as discussed above). Optionally, the computer does not transmit packets over the communication network. Optionally, the computer is connected to a single networking device that is connected to the communication network.

FIG. 1 illustrates one embodiment of a system configured to notify about availability of a medical device that is intended to receive maintenance. In one embodiment, the system includes a computer 120, which receives and analyzes packets transmitted over a communication network 118. The computer 120 may include one or more of the computers described in this disclosure (e.g., computer 400 illustrated in FIG. 18). The system may optionally include other elements such as a user interface 122, a database 123, and other optional elements as described below. The computer 120 is configured to run one or more computer programs that cause it to perform operations described below (which may correspond to at least some of the steps of the method illustrated FIG. 2).

In some embodiments, the computer 120 receives packets transmitted over the communication network 118. Optionally, the packets are received via a mirror port 126 on a networking device 124. In other embodiments, the computer 120 may receive the packets using other mechanisms (e.g., a network TAP, a host set to operate in promiscuous mode, and plug-ins), as described further above in this disclosure.

The networking device 124 is connected to the communication network 118 belonging to a medical facility. A plurality of N medical devices (denoted by reference numerals 121-1 to 121-N) are connected to the communication network 118 (via a wired connection and/or a wireless connection). Optionally, the mirror port 126 mirrors network traffic that includes packets travelling through port 125 of the networking device 124 and provides a copy of said traffic to the computer 120. Optionally, the packets travelling through the port 125 include packets transmitted to, and/or transmitted by, EMR 128 (or some other computer systems of the medical facility). In one example, the traffic includes packets that include data related to medical device activity at the medical facility, which is related to the operation of medical devices 121-1 to 121-N, and EMR 128 stores at least some of this data.

It is to be noted that herein, using the suffix 1 to N (as with the medical devices 121-1 to 121-N), or with other elements in this disclosure (e.g., references to communication networks at multiple facilities) is intended to denote a plurality of similar elements, unless noted otherwise.

The computer 120 performs deep packet inspection (DPI) of the packets related to medical device activity it receives. Optionally, if results of the DPI of certain packets received by the computer 120 indicate that they are not related to medical device activity (e.g., they were not sent by, or to, the medical devices 121-1 to 121-N), the certain packets and/or results obtained from DPI of the certain packets are not utilized by the computer 120 for additional analysis.

The computer 120 extracts, from results of the DPI of the packets, values that include identifiers of medical devices (which are from among the medical devices 121-1 to 121-N), and indications of whether these medical devices were being utilized in treatments of patients. Optionally, the extracted values correspond to treatment sessions, indicating for each treatment session an identifier of a medical device being utilized in the treatment session and an indication of the time (which can help determine when the treatment session started and/or provide an indication of the last known time it took place). Optionally, the values are utilized to update the database 123 that stores statuses of the medical devices.

It is to be noted that the analysis of the packets, by the computer 120, can be viewed, in some embodiments, as an essentially continuous process, with the status of each medical device being updated "on-the-fly" as additional packets are captured and analyzed. Thus, the database 123 can provide a snapshot, for any given time that includes the status of each of the medical devices 121-1 to 121-N, according to analysis of network traffic that includes packets transmitted over the communication network 118. Optionally, the database 123 can be accessed to provide an indication for each of the medical devices of whether it is being utilized to treat a patient. Additionally or alternatively, the database 123 may be accessed to determine when a treatment session with a specific medical device started and/or when a treatment session with a specific medical device is expected to end.

Information obtained from the results of the DPI of the packets may be utilized in various ways to assist in streamlining the running of a medical facility. The following discussion relates to making the task of providing maintenance to medical devices more efficient. To this end, the computer 120 receives an identifier 119 of a certain medical device that needs to receive maintenance. For example, the identifier may be received from a biomedical engineer at the medical facility, a computerized system used to manage inventory at the medical facility, or a technician or company that needs to provide maintenance to the certain medical device. Depending on the status of the certain medical device, the computer 120 may perform different operations.

In an event that the computer 120 determines that the device is not being utilized, the computer 120 may provide an indication of this fact. For example, the computer 120 may provide a notification to a technician and/or biomedical engineer indicating that the certain medical device is available for maintenance. Optionally, the notification may provide a location of the certain medical device (as determined based on results of the DPI of at least some of the packets). Optionally, the computer 120 may also provide an indication (e.g., to a nurse station), that the certain medical device should not be utilized at the moment (until it receives the maintenance).

In an event that the certain medical device is being utilized, this can introduce delays and inefficiencies into the process of providing maintenance to medical devices at the facility, since typically medical devices are not supposed to receive maintenance, and/or may be incapable of receiving maintenance, when they are being utilized to treat a patient. When the computer 120 is faced with such a situation, it may perform several operations that assist in making the maintenance process at the medical facility more efficient.

In one embodiment, the computer 120 determines, based on values extracted from a result of DPI of a first packet, that the certain medical device was being utilized to treat a patient. For example, the certain medical device transmitted the first packet that included information indicating that it is being utilized (e.g., the data in the first packet included a patient ID and/or values of parameters related to a treatment session). Optionally, this information is used to update the status of the certain medical device in the database 123.

Upon receiving the identifier 119 of the certain medical device, the computer 120 can send, based on the knowledge of the status of the certain medical device at the time, a first notification indicating that the certain medical device should not be utilized to treat additional patients. Optionally, this first notification is sent in order to help make the certain medical device available for maintenance as soon as possible, and avoid a situation in which the certain medical device is used in another treatment session after the current one it is used in. Optionally, the first notification is sent to nursing personnel, such as a message that appears on terminals and/or devices at one or more nursing stations in the vicinity of the certain medical device. Optionally, the first notification is sent is response to a query, received by the computer 120, which is intended to check the status of the certain medical device (in order to determine whether it is available to be utilized to treat patients).

Following that, the computer 120 may continue to monitor traffic on the communication network 118. After some time, the computer 120 may determine, based on values extracted from a result of DPI of a second packet, which was transmitted after the first packet, that the certain medical device was no longer being utilized to treat any patient. In this event, the computer 120 may send a second notification indicating that the certain medical device is available for maintenance. For example, the second notification may be sent to a technician and/or biomedical engineer who is supposed to provide the maintenance.

In one embodiment, the computer 120 sends a notification indicating to postpone maintenance on the certain medical device, responsive to determining, based on values extracted from a result of DPI of a third packet transmitted some time after the second notification was sent, that the certain medical device is being utilized in the treatment of a patient. This third notification can save a person seeking to provide maintenance to the certain medical device from wasting time searching for the certain medical device, only to find it is being utilized (and thus not amenable to receive maintenance).

The computer 120 may utilize, in some embodiments, information obtained from results of the DPI to provide locations of medical devices, and in particular provide the location of the certain medical device in notifications it sends. In one embodiment, the computer 120 obtains a value indicative of a physical location of the certain medical device from the results of the DPI of the second packet, and provides the physical location of the certain medical device in the second notification. Optionally, the computer 120 presents the location of certain medical device on the user interface 122.

In addition to determining a current status of a medical device, the computer 120 may rely on analysis of results of the DPI of the packets to determine when the status of a medical device is expected to change. In one example, the computer 120 may calculate, based on values extracted from DPI of one or more of the packets (which were transmitted at an earlier time than the first packet was transmitted), a time at which utilization of the certain medical device to treat the patient will end. The computer 120 may send the second notification before the calculated time. For example, the second notification may be sent 10 or 15 minutes before the calculated time the treatment will end. Optionally, the second notification may include an indication of the time at which utilization of the certain medical device to treat the patient is expected to end.

In one embodiment, the user interface 122 may be configured to present the second notification while the patient is still being treated utilizing the certain medical device. For example, the user interface 122 may belong to a device of a person tasked with providing the maintenance to the certain device. Optionally, devices in use are presented to the maintenance person in different colors than devices not in use.

Calculating the time at which utilization of the certain medical device to treat the patient is expected to end, can be done in various ways. In some embodiments, the calculation involves extracting from results of DPI of the one or more of the packets, previous durations of treatment sessions, and using the previous durations to calculate the time the treatment session is expected to end. The computer 120 may use the previous durations to calculate the time the treatment session is expected to end in various ways. In one example, this calculation may involve adding the average of the previous durations to a start time of the treatment session (where the start time may be identified based on results of DPI of the first packet or some other packet transmitted ahead of it). In another example, the previous durations can be utilized to train a machine learning-based model that is utilized to predict a duration of a certain treatment session based on characteristics of the certain treatment session (e.g., operating parameters, location, etc.). This model can then be utilized by the computer 120 to predict the duration of the treatment session, and then the computer 120 may add the predicted duration to the start time of the treatment session in order to estimate the time the treatment utilizing the certain medical device will end.

The following are some examples of various ways in which the time the treatment session is expected to end may be calculated, which involve using different choices of previous durations.

In one embodiment, the computer 120 may calculate the time treatment session is expected to end by: extracting, from results of the DPI of the one or more of the packets, durations of previous treatment sessions of the patient, and calculating the time based on the durations. For example, the computer 120 may identify in the results of the DPI of the one or more packets, data relating to treatment sessions involving the same patient identification number, and extract the durations of those treatment sessions. For example, the calculated time may be an average of the durations of the previous treatment sessions, or some other function of those values.

In another embodiment, the computer 120 may calculate, based on the values obtain from DPI of at least some of the packets (which were transmitted before the first packet), durations of previous treatment sessions utilizing the certain medical device. These previous durations are then utilized by the computer 120 to calculate the time at which the utilization of the certain medical device to treat the patient is expected to end (under the assumption that the current treatment session will be similar to previous ones with the certain medical device).

In yet another embodiment, the computer 120 may calculate the time a treatment session is expected to end by extracting, from results of the DPI of the one or more of the packets, additional values comprising operating parameters utilized in previous treatment sessions utilizing medical devices of the same type as the certain medical device. The additional values may then be utilized to calculate the time based on durations of previous treatment sessions that had similar operating parameters to operating parameters of the certain medical device utilized to treat the patient.

It is to be noted that some embodiments of the system illustrated in FIG. 1 may be designed such that they do not interfere with operations of medical devices and/or other computer systems of the medical facility, nor may they require changes be made to the computer systems or communication networks (beyond a mechanism for capturing the packets). Therefore, in some embodiments, the packets received by the computer 120 are not transmitted in response to a query of the computer 120 to an EMR system or to any other computer system of the medical facility, and are not transmitted in response to a communication sent by the computer 120 (i.e., the packets are transmitted because of the routine operations of medical devices and not because of operations performed by the computer 120). Furthermore, the computer 120 need not be an integral part of the computing infrastructure of the medical facility. In one embodiment, the computer 120 does not have access to an EMR system to which at least some of the packets are sent. In another embodiment, the computer 120 does not have permission to access and/or command any of the medical devices 121-1 to 121-N. In yet another embodiment, the computer 120 does not transmit packets over the communication network 118. In still another embodiment, the computer 120 is connected to a single networking device 124 that is connected to the communication network 118.

Figure 2:
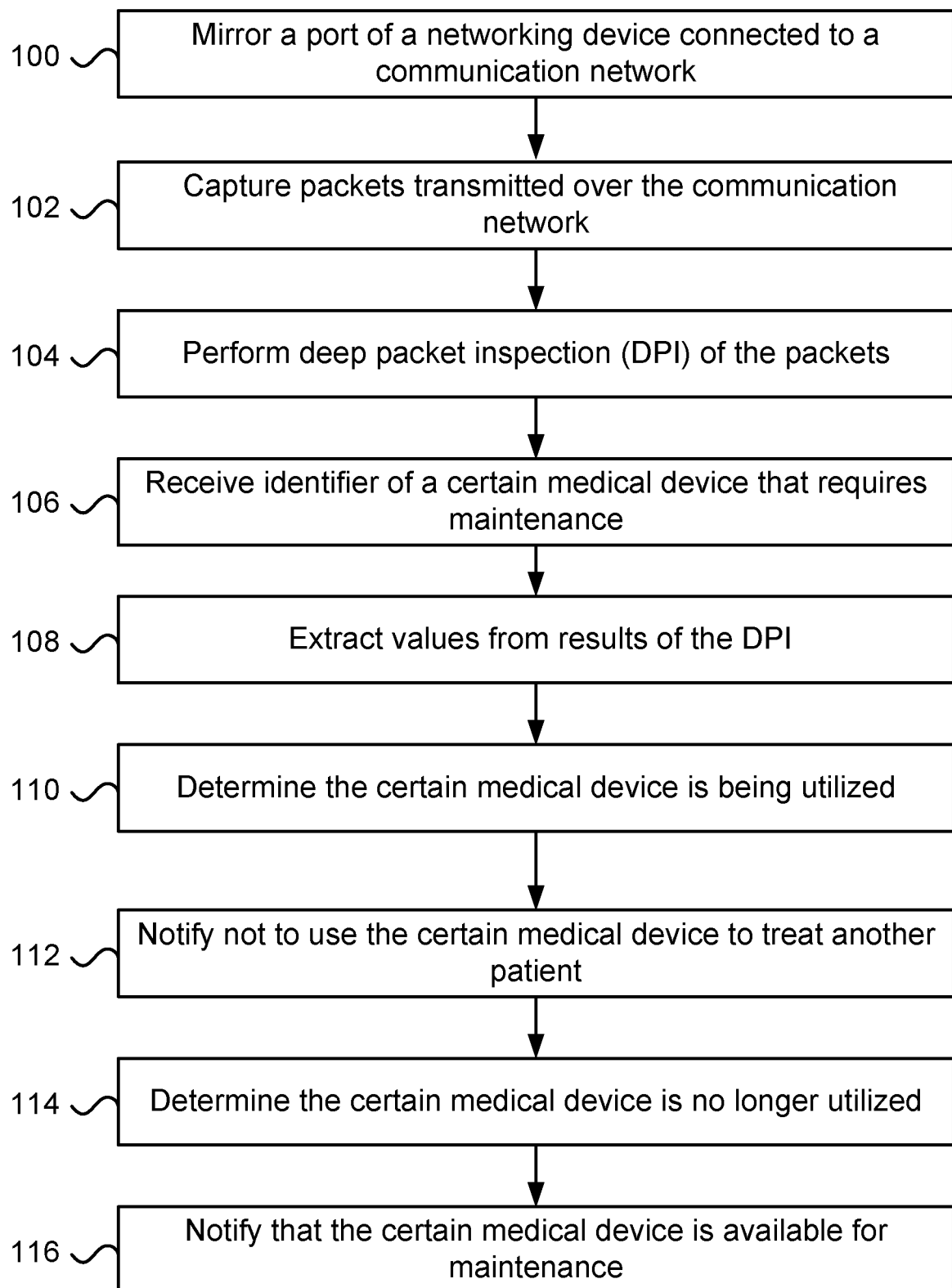
FIG. 2 illustrates steps involved in one embodiment of a method for notifying about availability of a medical device to receive maintenance.

FIG. 2 illustrates steps involved in one embodiment of a method for notifying about availability of a medical device to receive maintenance. The steps illustrated in FIG. 2 may be executed, in some embodiments, by systems modeled according to FIG. 1, which is described above. In some embodiments, instructions for implementing the method may be stored on a computer-readable medium, which may optionally be a non-transitory computer-readable medium. In response to execution by a computer system including a processor and memory (e.g., the computer 120 described above), the instructions cause the computer system to perform operations of the method.

In one embodiment, the method for notifying about availability of a medical device to receive maintenance includes at least the following steps:

In Step 102, receiving packets transmitted over a communication network (e.g., the communication network 118). Optionally, this step may be performed essentially continuously, through continuous monitoring and capturing of traffic of packets as they are sent over the communication network.

In Step 104, performing deep packet inspection (DPI) of the packets (e.g., by the computer 120, as described above).

In Step 106, receiving an identifier of a certain medical device that is intended to receive maintenance. In one example, the maintenance intended for the certain medical device is periodic preventative maintenance.

In Step 108, extracting, from results of the DPI, values comprising: identifiers of medical devices, and indications of whether the medical devices were being utilized in treatments of patients.

Values extracted in Step 108 may be utilized to decide how to respond to situations, such as an intent to provide maintenance to the certain medical device. The following steps of the method relate to a case in which the certain medical device is being utilized to treat a patient at a time the maintenance is planned. Other actions that may be performed are described above with relation to the operation of the computer 120 in different cases based on the results of the DPI of the packets sent over the communication network 118.

In Step 110, determining, based on the values extracted from a result of DPI of a first packet, that the certain medical device was being utilized to treat a patient. Optionally, this determination is done by querying the database 123, at a time after the first packet was analyzed using DPI, regarding the status of the certain medical device (e.g., by requesting the status of the certain medical device using the identifier received in Step 104). Optionally, the result returned by the database 123 indicates that at the time of the query the certain medical device was being utilized to treat a patient (and thus is not in a suitable state to receive maintenance).

In Step 112, sending a first notification indicating that the certain medical device should not be utilized to treat additional patients. Optionally, this first notification is sent with the intention of ensuring that the certain medical device will not be utilized again before receiving the maintenance it is due.

In Step 114, determining, based on values extracted from a result of DPI of a second packet, which was transmitted after the first packet, that the certain medical device was no longer being utilized to treat any patient. Optionally, this determination is done by querying the database 123, at a time after the second packet was analyzed using DPI, regarding the status of the certain medical device (e.g., by requesting the status of the certain medical device using the identifier received in Step 104); and In Step 116, sending a second notification indicating that the certain medical device is available for maintenance.

In some embodiments, the method may include optional Step 100, which involves receiving the packets utilizing port mirroring of a port on a networking device connected to the communication network (e.g., the packets may be received via the mirror port 126 that mirrors the port 125, as described above).

In one embodiment, the method may optionally include a step involving obtaining a value indicative of a physical location of the certain medical device from the DPI of the second packet, and providing the physical location of the certain medical device in the second notification. Optionally, the method also involves a step of presenting the location of the certain medical device on a user interface (e.g., the user interface 122).

In one embodiment, the method may optionally include a step involving sending a third notification indicating to postpone maintenance on the certain medical device, responsive to determining, based on values extracted from a result of DPI of a third packet transmitted some time after the second notification was sent, that the certain medical device is being utilized in the treatment of a patient.

In some embodiments, the method may optionally include a step involving calculating, based on values extracted from results of DPI of one or more of the packets, a certain time at which utilization of the certain medical device to treat the patient is expected to end, and sending the second notification before that time (instead of, or in addition to sending the notification in Step 112). Calculating the certain time may be done in various ways. In one embodiment, calculation of the certain time involves extracting, from the results of the DPI of the one or more of the packets, durations of previous treatment sessions of the patient, and calculating the certain time based on the durations. In another embodiment, calculation of the certain time involves calculating, based on at least some of the values, durations of previous treatment sessions utilizing the certain medical device, and utilizing the durations to calculate the certain time. In yet another embodiment, calculation of the certain time involves extracting, from the results of the DPI of the one or more of the packets, additional values comprising operating parameters utilized in previous treatment sessions utilizing medical devices of the same type as the certain medical device, and utilizing the additional values to calculate the certain time based on durations of previous treatment sessions that had similar operating parameters to operating parameters of the certain medical device utilized to treat the patient.

Figure 3A:
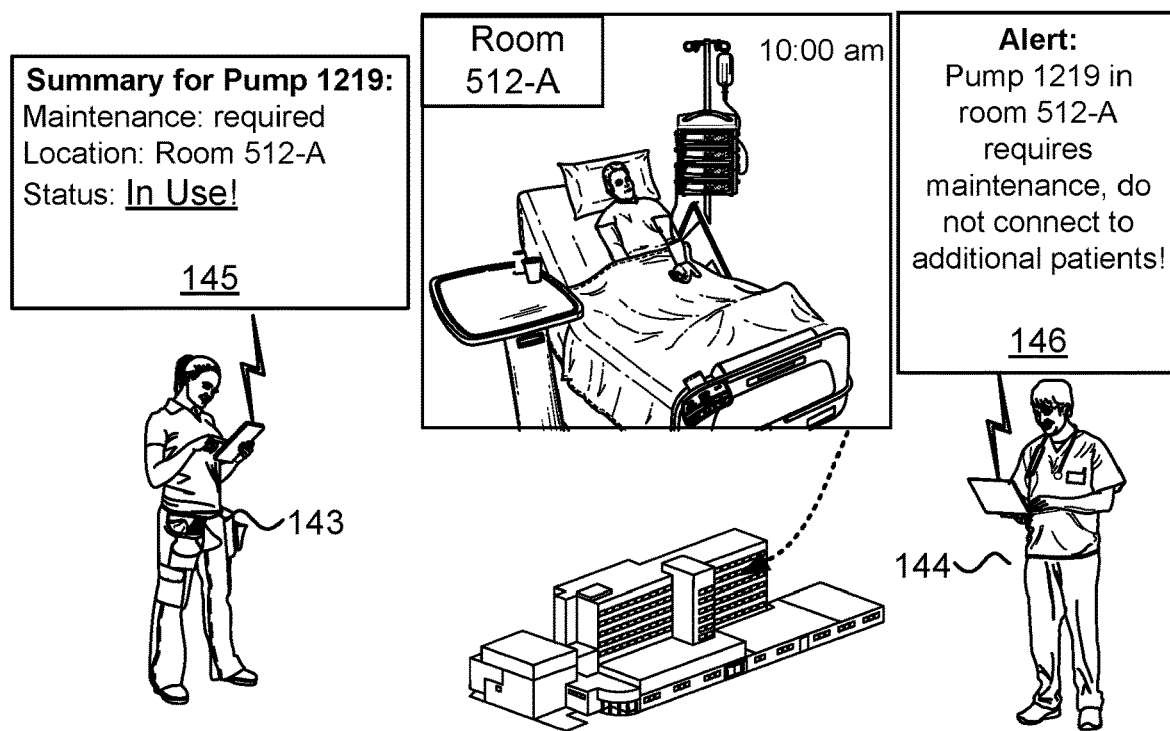
FIG. 3a and FIG. 3b illustrate notifying about availability of a medical device that is due for maintenance.
Figure 3B:
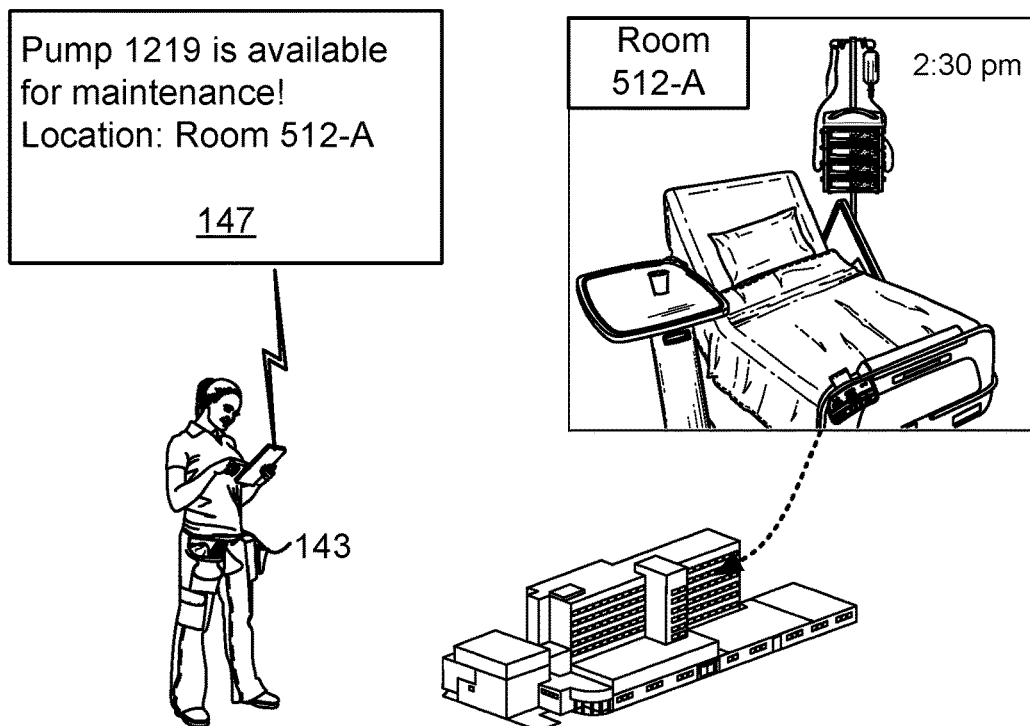

FIG. 3a and FIG. 3b illustrate notifying about availability of a medical device that is due for maintenance, as described in embodiments above. FIG. 3a illustrates an infusion pump that requires maintenance, but is being utilized. A technician 143 who is supposed to provide preventative maintenance to the infusion pump is notified via a notification 145 about the location of the infusion pump and the fact that it is currently in use (and therefore cannot be provided with preventative maintenance at that time). Additionally, a notification 146 is sent to nurse 144 requesting that the infusion pump not be connected to additional patients (this notification is an implementation of Step 112 of the method described above). FIG. 3b illustrates a later time, at which the infusion pump is no longer being utilized to treat a patient. When this situation is identified, a notification 147 is sent to technician 143 in order for her to attend to the infusion pump. This example illustrates how embodiments of the invention can save valuable time (and money) for medical facilities by directing maintenance personnel to medical devices at appropriate times (and freeing them to deal with other tasks when medical devices are not amenable to receive maintenance).

Figure 4:
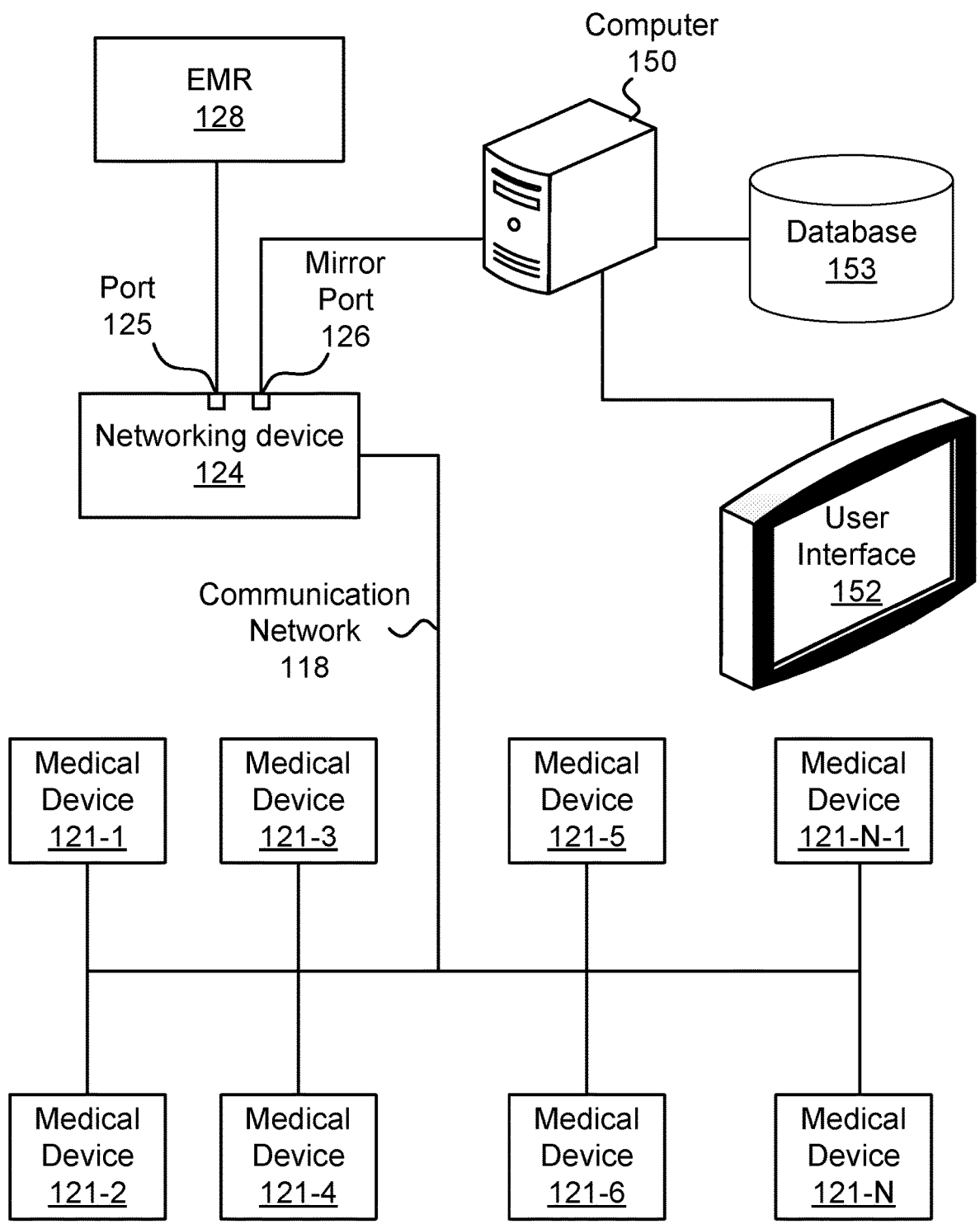
FIG. 4 illustrates one embodiment of a system configured to recommend utilization-based preventative maintenance to medical devices.

FIG. 4 illustrates one embodiment of a system configured to recommend utilization-based preventative maintenance to medical devices. In one embodiment, the system includes a computer 150, which receives and analyzes packets transmitted over the communication network 118. The computer 150 may include one or more of the computers described in this disclosure (e.g., computer 400 illustrated in FIG. 18). The system may optionally include other elements such as a user interface 152, a database 153, and other optional elements as described below. The computer 150 is configured to run one or more computer programs that cause it to perform operations described below (which may correspond to at least some of the steps of the method illustrated FIG. 5).

In some embodiments, the computer 150 receives packets related to activity of the medical devices 121-1 to 121-N, which are transmitted over the communication network 118. Optionally, the packets are received via the mirror port 126 on the networking device 124. In other embodiments, the computer 150 may receive the packets using other mechanisms, e.g., a network TAP, a host set to operate in promiscuous mode, and/or plug-ins, as described further above in this disclosure. Optionally, at least some of the medical devices 121-1 to 121-N receive preventative maintenance throughout their lifetime. Some of the embodiments described below describe how scheduling their preventative maintenance can be done based on the extent to which they were utilized.

The computer 150 performs deep packet inspection (DPI) of the packets related to medical device activity it received. Optionally, if results of the DPI of certain packets received by the computer 150 indicate that they are not related to medical device activity (e.g., they were not sent by, or to, the medical devices 121-1 to 121-N), the certain packets and/or results obtained from DPI of the certain packets are not utilized by the computer 150 for additional analysis.

The computer 150 extracts, from results of the DPI of the packets, values that include identifiers of medical devices (from among the medical devices 121-1 to 121-N), and indications of whether these medical devices were being utilized in treatments of patients. Optionally, the extracted values correspond to treatment sessions, indicating for each treatment session an identifier of a medical device being utilized in the treatment session and an indication of the time (which can help determine when the treatment session started/ended). Optionally, the extracted values comprise indications of the durations of the treatment sessions. Optionally, the extracted values comprise indications of the type of treatments provided in each treatment session (which may be indicative of a specific type of usage of the medical device during the treatment session). Optionally, the values are utilized to update a database 153 that stores values indicative of the extent of utilization of the medical devices (e.g., how many times and/or how many hours each device had been used over various periods of time).

It is to be noted that as mentioned above, the aforementioned analysis of the packets may be a continuous process. In some embodiments, the database 153 may be updated continuously ("on-the-fly") as utilization of medical devices is detected and/or periodically (e.g., at the end of the day, week, and/or month). Thus, the database 153 can provide upon request a summary the extent of utilization for each of the medical devices 121-1 to 121-N, according to analysis of network traffic that includes packets transmitted over the communication network 118. Optionally, the database 153 can be accessed to provide an indication for each of the medical devices 121-1 to 121-N of how many times, and/or how many hours, it was utilized to treat patients during a certain period. Additionally or alternatively, the database 153 may be accessed to determine when a treatment session with a specific medical device started, and/or when a treatment session with the specific medical device is expected to end.

The computer 150 receives dates at which preventative maintenance was provided to the medical devices 121-1 to 121-N. Optionally, at least some of the medical devices 121-1 to 121-N received preventative maintenance on different days. There may be various possibilities for how these dates are received. In one embodiment, this data may be sent by a computer system of the medical facility (e.g., an EMR). In another embodiment, the computer 150 may determine the dates at which preventative maintenance was provided based on results of DPI of previously captured packets transmitted over the communication network 118. For example, part of the preventative maintenance may involve running certain procedures that cause medical devices that received preventative maintenance to transmit certain packets that contain data indicating they received preventative maintenance (and this data is detected in results of DPI of the certain packets). In another example, preventative maintenance may be tied to updating version of certain software and/or firmware on a medical device, and an updated version may be detected in data transmitted by and/or to the medical device. In still another embodiment, the dates at which preventative maintenance was provided to the medical devices 121-1 to 121-N may be provided by a technician conducting the preventative maintenance and/or an employee at the medical facility. And in yet another example, preventative maintenance may be known to be provided at predetermined dates and/or intervals. Thus, the computer 150 may determine the dates at which preventative maintenance was provided to each of the medical devices 121-1 to 121-N by subtracting a predetermined duration from the date at which the computer 150 makes its recommendations.

In some embodiments, if a medical device from among the medical devices 121-1 to 121-N had yet to receive preventative maintenance, the date of the last preventative maintenance may correspond to some other date. Some examples of options for the date to use in such a case include: the date the medical device was received by the medical facility, the date the medical device was first detected as being connected to the communication network 118, and/or the date the medical device was first utilized to treat a patient (e.g., as detected based on results of DPI of packets transmitted over the communication network 118).

In order to make a utilization-based recommendation for preventative maintenance, the computer 150 calculates, based on values extracted from the results of the DPI of the packets and the dates at which preventative maintenance was provided to each of the medical devices 121-1 to 121-N, extents of utilization of the medical devices 121-1 to 121-N since receiving the most recent preventative maintenance. For example, the extents of utilization may be indicative, for each medical device, of the number of treatments in which the medical device was utilized and/or the number of hours the medical device was utilized in treatments. Optionally, the extents of utilization since last receiving preventative maintenance are calculated by subtracting current extents of utilization of the medical devices 121-1 to 121-N from extents of utilization they had when they last received preventative maintenance (e.g., as stored in the database 153). Alternatively, each time a medical device receives preventative maintenance, a counter representing its current extent of utilization is set to zero, and this value is incremented based on indications of treatment sessions identified in the results of the DPI of the packets.

In some embodiments, the calculated extents may be stratified to indicate extent of utilization for various types of treatments (thus for each type of treatment there is a calculated extent of utilization). Optionally, the types of treatments are determined based on results of DPI of the packets. Optionally, when discussing extent of utilization, the calculated extents may refer to a certain treatment type and/or a specific weighting of treatments, such that, for examples, an hour of utilization of a medical device for treatment type A may be considered more or less than an hour of utilization of the same medical device for treatment type B.

The computer 150 may utilize the calculated extents of utilization in various ways in order to recommend which of the medical devices 121-1 to 121-N should receive preventative maintenance next and/or to create an order in which at least some of the medical devices 121-1 to 121-N are to receive preventative maintenance. In one example, the medical facility can provide preventative maintenance during a certain period only to a certain number X<N of the medical devices 121-1 to 121-N, and the computer 150 selects a subset of X medical devices that includes the medical devices from among the medical devices 121-1 to 121-N that had the highest extents of utilization. In another example, the computer 150 may generate a service order that dictates an order an which the medical devices 121-1 to 121-N are to receive preventative maintenance; in this order, medical devices with higher extents of utilization are ranked ahead of medical devices with lower extents of utilization. For example, in this order, a first medical device that is ranked ahead of a second medical device is expected to receive preventative maintenance before the second medical device. In yet another example, medical devices from among the medical devices 121-1 to 121-N whose extent of utilization reaches a threshold are recommended to receive preventative maintenance, while medical devices from among the medical devices 121-1 to 121-N, whose extent of utilization does not reach the threshold, are not recommended to receive preventative maintenance.

Making recommendations for preventative maintenance of medical devices based on extents of utilization means that, in at least some cases, the computer 150 will recommend, based on the extents, that a certain medical device receive preventative maintenance before another medical device. In such cases, an extent of utilization of the certain medical device since its most recent preventative maintenance may be greater than an extent of utilization of the other medical device since the other medical device's most recent preventative maintenance. The fact that the computer 150 recommends that the certain medical device receive maintenance earlier than the other medical device may go against typical approaches to providing preventative maintenance, which rely on dates at which preventative maintenance was last provided. Thus, it may be the case that the aforementioned certain medical device had last received maintenance at a later date (or a date that is not earlier) than the date the other medical device last received maintenance.

In one embodiment, an extent of utilization of the aforementioned certain medical device since its most recent preventative maintenance reaches a predetermined threshold, and the extent of utilization of the other medical device since its most recent preventative maintenance does not reach the predetermined threshold. Optionally, the predetermined threshold is calculated based on data comprising: extents of utilization of various medical devices, and data regarding when non-routine maintenance was required for the various medical devices. Optionally, the various medical devices belong to various medical facilities. Such (crowd-based) data from multiple facilities, which may implement different preventative maintenance protocols can be used to determine a relationship between extent of utilization (between preventative maintenance sessions) and a probability of having a non-routine maintenance call (e.g., due to a medical device being non-operational). The predetermined threshold may be set such that the expected probability of having a non-routine maintenance call is below a certain value that offers a reasonable balance between the cost of preventative maintenance and the cost of having medical devices break down.

A recommendation that the certain medical device receive preventative maintenance before another medical device may be conveyed to various recipients. In one embodiment, this information is conveyed to a computer system of the medical facility, such as an enterprise resource planning (ERP) system. In another embodiment, this information is conveyed to a user interface 152. In one example, the user interface 152 may belong to a workstation of an administrator at the medical facility. In another example, the user interface 152 may be a tablet screen or smartphone of a technician or biomedical engineer that services medical devices at the medical facility.

It is to be noted that in embodiments described herein, which involve utilization-based recommendations for preventative maintenance (e.g., by the computer 150), the process of analyzing packets may be an ongoing process and involves packets transmitted over a long period. In one example, the packets analyzed by the computer 150 include packets comprising activity of the medical devices 121-1 to 121-N that dates back at least to their arrival at the medical facility or their last preventative maintenance session. In another example, the packets analyzed by the computer 150 were transmitted over a period that (i) began on or before the earliest from among the date of most recent preventative maintenance to the aforementioned certain medical device and (ii) began on or before the date of the most recent preventative maintenance to the aforementioned other medical device.

The extents of utilization of the medical devices 121-1 to 121-N may be utilized, in some embodiments, for additional purposes in addition to making scheduling decisions regarding preventative maintenance. In some embodiments, the extents of utilization of the medical devices 121-1 to 121-N can be used for the purpose of "load balancing" utilization of various medical devices of a certain type (e.g., infusion pumps), to reduce cases in which certain medical devices at a medical facility are heavily utilized, while other medical devices of the same type (perhaps in a different location in the medical facility) are utilized much less. Performing load balancing with the purpose of making the utilization of the different devices more uniform can have advantages in extending the life of the medical devices and making the preventative maintenance more efficient (i.e., have the medical devices receive preventative maintenance in a timely manner and not too early or too late).

Figure 7:
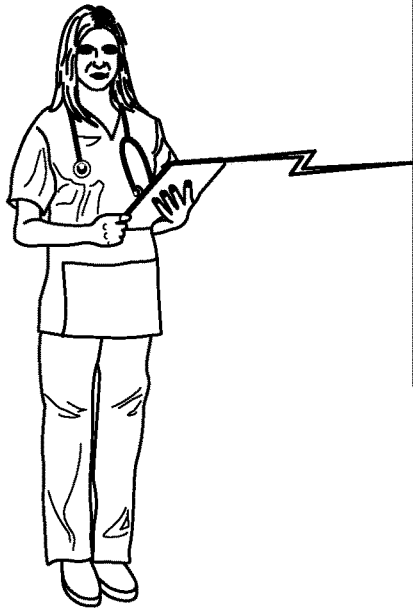
FIG. 7 illustrates a scenario in which a nurse receives a recommendation to utilize a certain infusion pump based on its lower.

In one embodiment, the computer 150 utilizes the extents of utilization of the medical devices 121-1 to 121-N (which are calculated based on results of DPI of the packets as described above), to recommend medical devices to be utilized to treat patients. Optionally, certain medical devices with lower utilization are recommended over medical devices with higher utilization (in order to achieve more uniform utilization across the medical devices 121-1 to 121-N). Optionally, when first and second medical devices are available to be utilized (e.g., the aforementioned other and certain medical devices, respectively), if the first medical device was utilized less than the second medical device, it is recommend more frequently than the second medical device. In this example, the computer 150 may receive a request to locate an available medical device that can be utilized to treat a patient. Given the situation above, the computer 150 may respond with an identifier and/or location of the first medical device (e.g., after querying the database 153), and recommend the first medical device over the second medical device. Optionally, the computer 150 may present such a recommendation on the user interface 152, which may be utilized by a worker of the medical facility who queried the computer 150 about an available medical device. FIG. 7 illustrates a scenario in which a nurse receives a recommendation 154 to utilize a certain infusion pump with low utilization over another infusion pump with higher utilization.

Recommending the first medical device over the second medical device may be done in various ways. In one example, the first medical device may be placed ahead of the second medical device on a list of medical devices displayed on the user interface 152. In another example, the first medical device may be displayed on the user interface 152, but the second medical device is not displayed on the user interface 152. In yet another example, the first medical device is displayed more prominently than the second medical device (e.g., using a larger icon or a visual effect such as flashing). In one embodiment, if an extent of utilization the first medical device is lower than an extent of utilization of the second medical device, the frequency at which the first medical device is recommended over the second medical device is higher than the frequency at which the second medical device is recommended over the first medical device.

Another way load balancing of medical devices may be achieved involves changing locations of medical devices at the medical facility. Not all rooms and care areas have the same loads and/or treatment needs. Therefore, it is quite often the case that a first medical device in a first care area may be highly used, but a second medical device, of the same type, in a second care area is not utilized as much. If at some point in time the locations of both medical devices are switched, this can help balance their extents of utilization.

Figure 8:
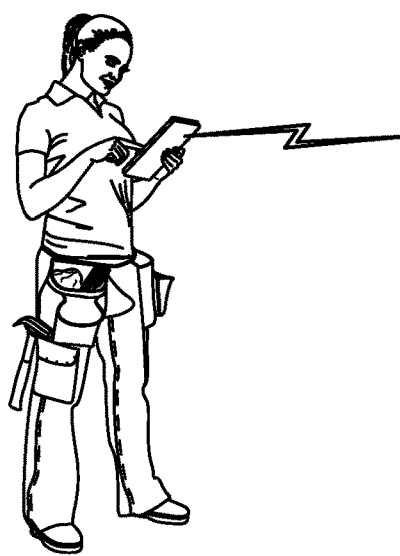
FIG. 8 illustrates a scenario in which a technician receives a recommendation to switch between locations of infusion pumps based on their utilization.

In one embodiment, the computer 150 makes a recommendation to switch between locations of first and second medical devices (e.g., the aforementioned certain and other medical devices, respectively). Optionally, this switch is suggested based on the fact that and extent of utilization of the first medical device since its most recent preventative maintenance was greater than an extent of utilization of the second medical device since the other medical device's most recent preventative maintenance. Optionally, the extents of utilization are obtained by querying the database 153. Optionally, querying the database 153 is performed periodically, e.g., by a biomedical engineer at the medical facility, in order to achieve more uniform utilization of the medical devices. The computer 150 may recommend switching locations of medical devices if certain criteria are met. For example, the first medical device's utilization may be above a first threshold, while the utilization of the second medical device may be below a second threshold, which is lower than the first threshold. In another example, the locations of the first and second medical devices are switched if the extent of utilization of the first medical device is at least a certain percentage greater than the extent of utilization of the second medical device. FIG. 8 illustrates a scenario in which a technician receives a recommendation 156 to switch between locations between a first lowly-utilized infusion pump and second highly-utilize one.

Suggesting the switching of locations of medical devices may be timed in order to postpone preventative maintenance that may be necessary if utilization patterns of the medical devices remain the same. In one example, the computer 150 makes a recommendation to switch between the aforementioned first and second medical devices a certain period (which is at least two months) before a scheduled date for preventative maintenance for the first medical device. Thus, given that for at least the certain period, the first medical device is expected to be utilized much less than before, the preventative maintenance scheduled for it might be able to be postponed (since the first medical device is not expected to have an extent of utilization that requires preventative maintenance as soon as it previously did, before switching the locations).

Whether switching locations of the aforementioned first and second medical devices will actually help to postpone preventative maintenance may be evaluated by the computer 150. In one embodiment, the computer 150 determines whether following the switch between locations, an increase in an extent of utilization of the first medical device is below a threshold. If it is below the threshold, the computer 150 may send a notification indicating to postpone scheduled preventative maintenance for the first medical device, since the increase in the extent of utilization following the switch is not expected to bring the total utilization to a level that warrants preventative maintenance as originally scheduled.

It is to be noted that some embodiments of the system illustrated in FIG. 4 may be designed such that they do not interfere with operations of medical devices and/or other computer systems of the medical facility, nor may they require changes be made to the computer systems or communication networks (beyond a mechanism for capturing the packets). Therefore, in some embodiments, the packets received by the computer 150 are not transmitted in response to a query of the computer 150 to an EMR system or to any other computer system of the medical facility, and are not transmitted in response to a communication sent by the computer 150 (i.e., the packets are transmitted because of the routine operations of medical devices and not because of operations performed by the computer 150). Furthermore, the computer 150 need not be an integral part of the computing infrastructure of the medical facility. In one embodiment, the computer 150 does not have access to an EMR system to which at least some of the packets are sent. In another embodiment, the computer 150 does not have permission to access and/or command any of the medical devices 121-1 to 121-N. In yet another embodiment, the computer 150 does not transmit packets over the communication network 118. In still another embodiment, the computer 150 is connected to a single networking device 124 that is connected to the communication network 118.

Figure 5:
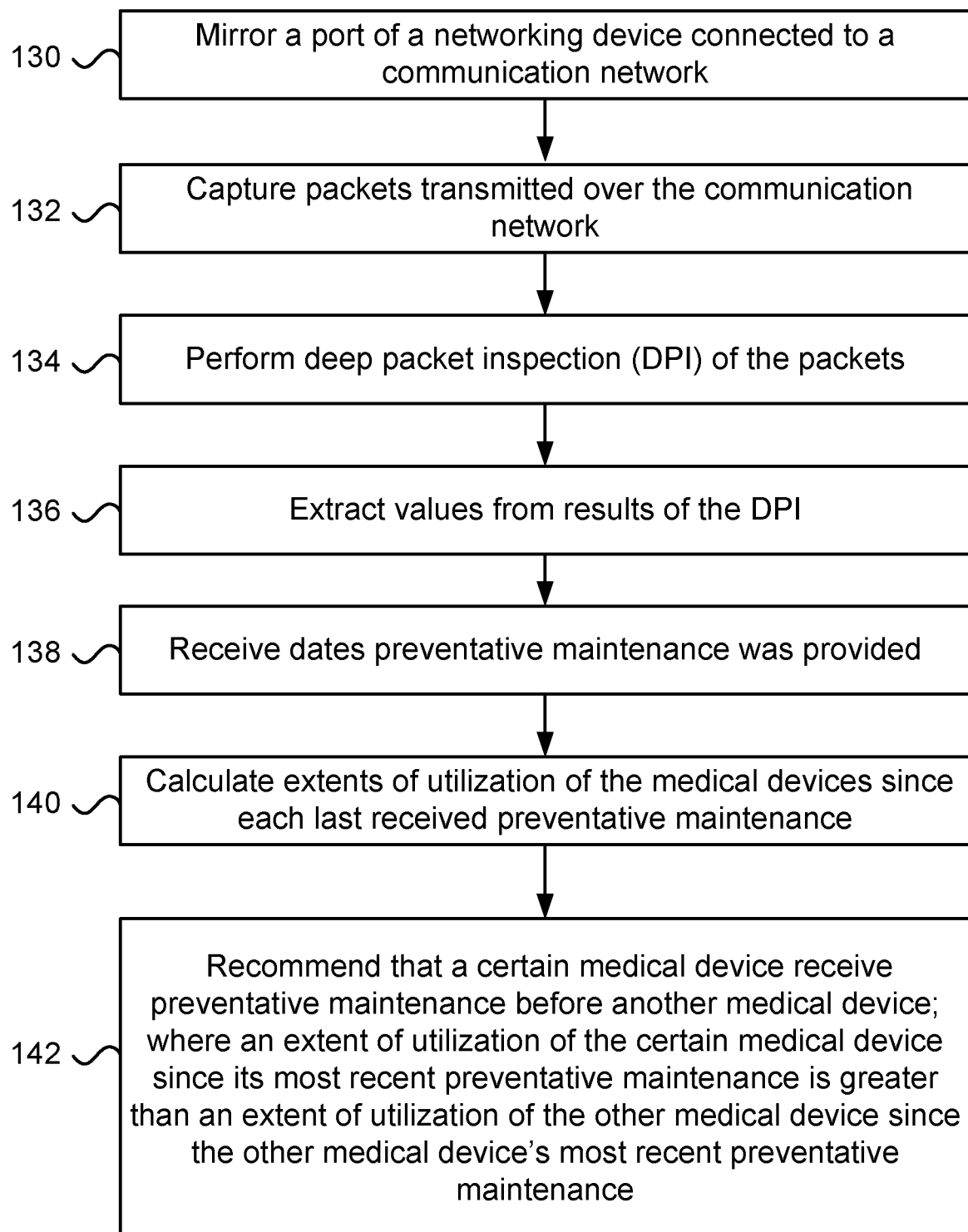
FIG. 5 illustrates steps involved in one embodiment of a method for recommending utilization-based preventative maintenance for medical devices.

FIG. 5 illustrates steps involved in one embodiment of a method for recommending utilization-based preventative maintenance for medical devices. The steps illustrated in FIG. 5 may be executed, in some embodiments, by systems modeled according to FIG. 4, which is described above. In some embodiments, instructions for implementing the method may be stored on a computer-readable medium, which may optionally be a non-transitory computer-readable medium. In response to execution by a computer system including a processor and memory (e.g., the computer 150 described above), the instructions cause the computer system to perform operations of the method.

In one embodiment, the method for recommending utilization-based preventative maintenance for medical devices includes at least the following steps:

In Step 132, capturing packets transmitted over a communication network (e.g., the communication network 118). Optionally, this step may be performed through continuous monitoring and capturing of traffic sent over the communication network.

In Step 134, performing deep packet inspection (DPI) of the packets (e.g., by the computer 150, as described above).

In Step 136, extracting, from results of the DPI, values comprising: identifiers of medical devices (from among the medical devices 121-to 121-N), and indications of whether the medical devices were being utilized in treatment of patients.

In Step 138, receiving dates at which preventative maintenance was provided to the medical devices 121-1 to 121-N.

In Step 140, calculating, based on the values and the dates, extents of utilization of each of the medical devices 121-1 to 121-N since receiving their most recent preventative maintenance (or since being introduced to the medical facility, if preventative maintenance was not provided to some of the medical devices 121-1 to 121-N).

And in Step 142 recommending, based on the extents, that a certain medical device receive preventative maintenance before another medical device. This recommendation may be based on the fact that an extent of utilization of the certain medical device since its most recent preventative maintenance is greater than an extent of utilization of the other medical device since the other medical device's most recent preventative maintenance. Optionally, the certain medical device had last received preventative maintenance at a later date than the date the other medical device last received preventative maintenance.

In some embodiments, the method may include optional Step 130, which involves receiving the packets captured in Step 132 utilizing port mirroring of a port on a networking device connected to the communication network (e.g., the packets may be received via the mirror port 126 that mirrors the port 125, as described above). Additionally, in some embodiments, capturing the packets (in Step 132) is performed over a period that begins not after the earliest from among the date of most recent preventative maintenance to the certain medical device and the date of the most recent preventative maintenance to the other medical device.

In one embodiment, the extent of utilization of the certain medical device since its most recent preventative maintenance reaches a predetermined threshold, and the extent of utilization of the other medical device since its most recent preventative maintenance does not reach the predetermined threshold. In this embodiment, the method may optionally include a step of calculating the predetermined threshold based on data comprising: extents of utilization of various medical devices, and data regarding when non-routine maintenance was required for the various medical devices. Optionally, the various medical devices were located at various facilities, and the predetermined threshold is calculated such that medical devices whose extent of utilization is below the predetermined threshold are expected to require non-routine maintenance at a probability that is lower than a certain value.

As discussed above, extents of utilization of the medical devices 121-1 to 121-N may be utilized in additional ways in order to achieve load balancing of the utilization of the medical devices. In one embodiment, the method may optionally include a step of recommending, based on the extents, which of the medical devices to utilize for treatments. Optionally, when the aforementioned certain medical device and the other medical device are both available to be utilized, the other medical device is recommended at a higher frequency than the certain medical device.

In another embodiment, the method may optionally include a step of recommending to switch between locations of the aforementioned certain medical device and the other medical device based on the extent of utilization of the certain medical device since its most recent preventative maintenance being greater than the extent of utilization of the other medical device since the other medical device's most recent preventative maintenance. Additionally, the method may optionally include a step of determining whether following the switch between locations, an increase in an extent of utilization of the certain medical device is below a threshold, and sending a notification indicating to postpone scheduled preventative maintenance for the certain medical device, responsive to a determination that the increase is below the threshold.

In addition to the use for recommending utilization-based preventative maintenance for medical devices, some embodiments modeled according to FIG. 4 may be utilized to identify a medical device scheduled for unnecessary preventative maintenance (which may be skipped). Skipping unnecessary preventative maintenance for medical devices with low utilization can offer great savings to medical facilities and allow them to focus their maintenance efforts on highly-utilized medical devices (that are more likely to benefit from receiving frequent preventative maintenance).

In some embodiments, a system configured to notify about a medical device scheduled for unnecessary preventative maintenance includes at least the computer 150. In these embodiments, the computer 150 is configured to run one or more computer programs that cause it to perform the operations described below, which may correspond to at least some of the steps of the method illustrated FIG. 6. In these embodiments, the computer 150 is configured to obtain the packets related to medical device activity transmitted over the communication network 118 (e.g., via the mirror port 126 of the networking device 124, as described above). The computer 150 performs DPI of the packets. The computer 150 extracts, from results of the DPI of the packets, values that include identifiers of medical devices (from among the medical devices 121-1 to 121-N), and indications of whether these medical devices were being utilized in treatments of patients. Optionally, the extracted values correspond to treatment sessions, indicating for each treatment session an identifier of a medical device being utilized in the treatment session and an indication of the time (which can help determine when the treatment session started/ended). Optionally, the values are utilized to update the database 153 that stores values indicative of the extent of utilization of the medical devices (e.g., how many times and/or how many hours each device had been used over various periods of time). Additionally, the computer 150 receives dates at which preventative maintenance was provided to each of the medical devices 121-1 to 121-N.

In some embodiments, the computer 150 calculates, based on values extracted from the results of the DPI of the packets and the dates at which preventative maintenance was provided to each of the medical devices 121-1 to 121-N, extents of utilization of the medical devices 121-1 to 121-N since receiving the most recent preventative maintenance. Given the calculated extents, the computer 150 may identify a medical device scheduled for an upcoming preventative maintenance whose extent of utilization is below a predetermined threshold, and provide a notification identifying said medical device. Optionally, the notification is displayed on the user interface 152 and/or sent to computer system of the medical facility.

The predetermined threshold utilized above may be a preset threshold, such as a threshold dictated by the manufacturer or a regulatory body. In other embodiments, the predetermined threshold may be based on crowd-based data from multiple facilities, as described above. In these embodiments, the computer 150 is further configured to calculate the predetermined threshold based on data comprising: extents of utilization of various medical devices, and data regarding when non-routine maintenance was required for the various medical devices.

In addition to identifying medical devices that may skip preventative maintenance, some embodiments may be utilized to notify about medical devices that require preventative maintenance (possibly at an earlier date than scheduled) because of high utilization. In these embodiments, the computer 150 may be further configured to: receive an indication of at least some medical devices, from among the medical devices 121-I to 121-N, which are scheduled to receive preventative maintenance. The computer 150 utilizes the calculated extents of utilization to identify a certain medical device, from among the medical devices 121-1 to 12-N, which is not among the at least some of the medical devices scheduled for preventative maintenance, whose extent of utilization reaches a second predetermined threshold, and notify about said certain medical device. The second predetermined threshold is greater than the predetermined threshold. Optionally, the second predetermined threshold represents at least twice the extent of utilization that the predetermined threshold represents.

Figure 6:
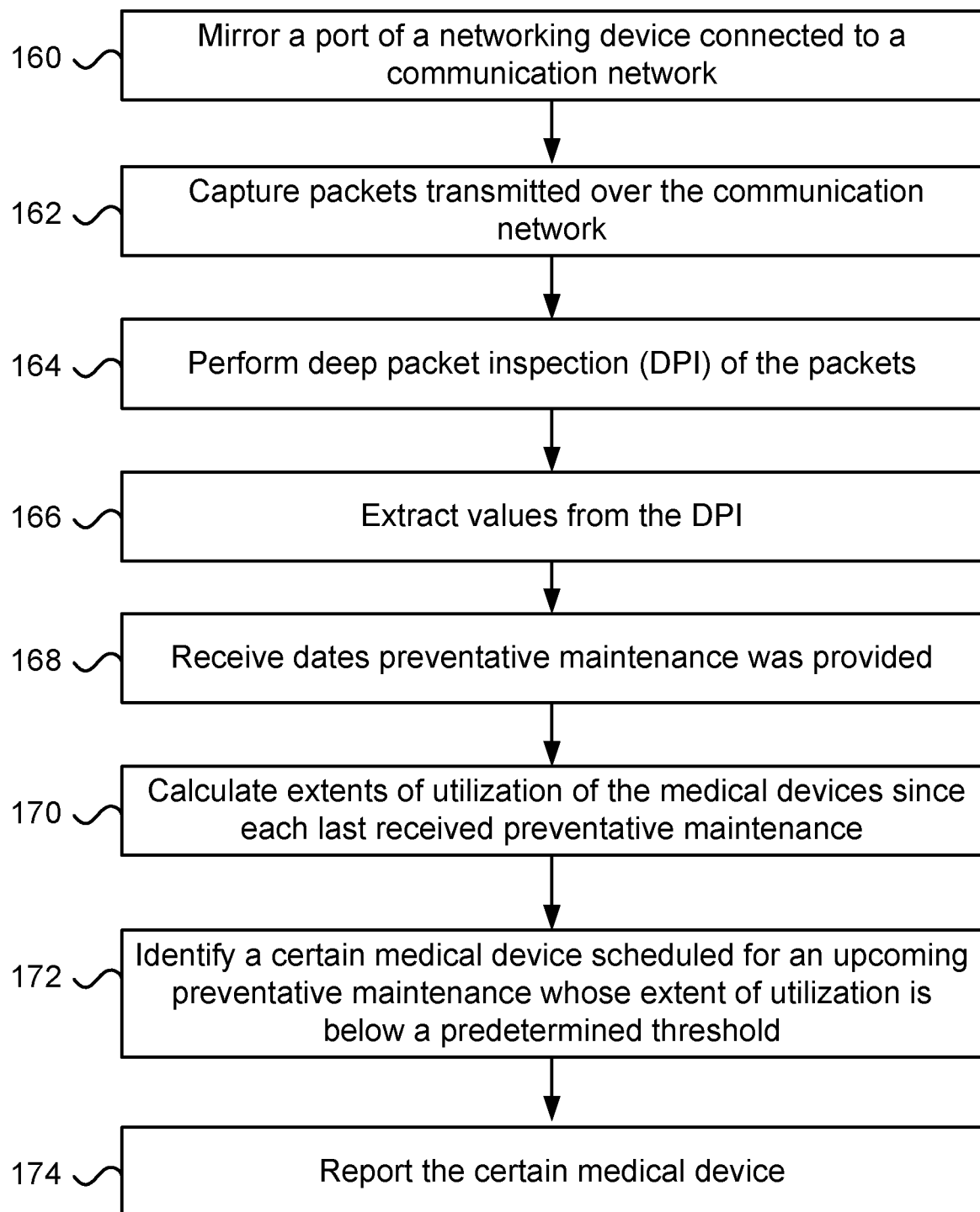
FIG. 6 illustrates steps involved in one embodiment of a method for notifying about a medical device scheduled for unnecessary preventative maintenance.

FIG. 6 illustrates steps involved in one embodiment of a method for notifying about a medical device scheduled for unnecessary preventative maintenance. The steps illustrated in FIG. 6 may be executed, in some embodiments, by systems modeled according to FIG. 4, as described above. In some embodiments, instructions for implementing the method may be stored on a computer-readable medium, which may optionally be a non-transitory computer-readable medium. In response to execution by a computer system including a processor and memory (e.g., the computer 150 described above), the instructions cause the computer system to perform operations of the method.

In one embodiment, the method for notifying about a medical device scheduled for unnecessary preventative maintenance includes at least the following steps:

In Step 162, capturing packets transmitted over a communication network (e.g., the communication network 118). Optionally, this step may be performed through continuous monitoring and capturing of traffic sent over the communication network.

In Step 164, performing deep packet inspection (DPI) of the packets.

In Step 166, extracting, from results of the DPI, values comprising: identifiers of medical devices, and indications of whether the medical devices were being utilized in treatment of patients.

In Step 168, receiving dates at which preventative maintenance was provided to each of the medical devices 121-1 to 121-N.

In Step 170, calculating, based on the values and the dates, extents of utilization of each of the medical devices 121-1 to 121-N since receiving the most recent preventative maintenance.

In Step 172, identifying, based on the extents calculated in Step 170, a certain medical device, from among the medical devices 121-1 to 121-N, which is scheduled for an upcoming preventative maintenance, whose extent of utilization is below a predetermined threshold.

And in Step 174, notifying about said certain medical device; for example, by sending a message to user interface 152 and/or sending a message to a computer system of the medical facility.

In some embodiments, the method may include optional Step 160, which involves receiving the packets captured in Step 162 utilizing port mirroring of a port on a networking device connected to the communication network (e.g., the packets may be received via the mirror port 126 that mirrors the port 125, as described above).

In one embodiment, the method may optionally include a step of calculating the predetermined threshold based on data comprising: extents of utilization of various medical devices, and data regarding when non-routine maintenance was required for the various medical devices. Optionally, the various medical devices are located at various facilities, and the predetermined threshold is calculated such that medical devices whose extent of utilization is below the predetermined threshold are expected to require non-routine maintenance at a probability that is lower than a certain value.

As discussed above, extents of utilization of the medical devices 121-1 to 121-N may be utilized in additional ways in order to achieve load balancing of the utilization of the medical devices. In one embodiment, the method may optionally include a step of recommending, based on the extents, which of the medical devices to utilize for treatments. Optionally, when the aforementioned certain medical device and the other medical device are both available to be utilized, the other medical device is recommended at a higher frequency than the certain medical device.

In another embodiment, the method may optionally include a step of recommending to switch between locations of the aforementioned certain medical device and the other medical device based on the extent of utilization of the certain medical device since its most recent preventative maintenance being greater than the extent of utilization of the other medical device since the other medical device's most recent preventative maintenance. Additionally, the method may optionally include a step of determining whether following the switch between locations, an increase in an extent of utilization of the certain medical device is below a threshold, and sending a notification indicating to postpone scheduled preventative maintenance for the certain medical device, responsive to a determination that the increase is below the threshold.

Figure 9:
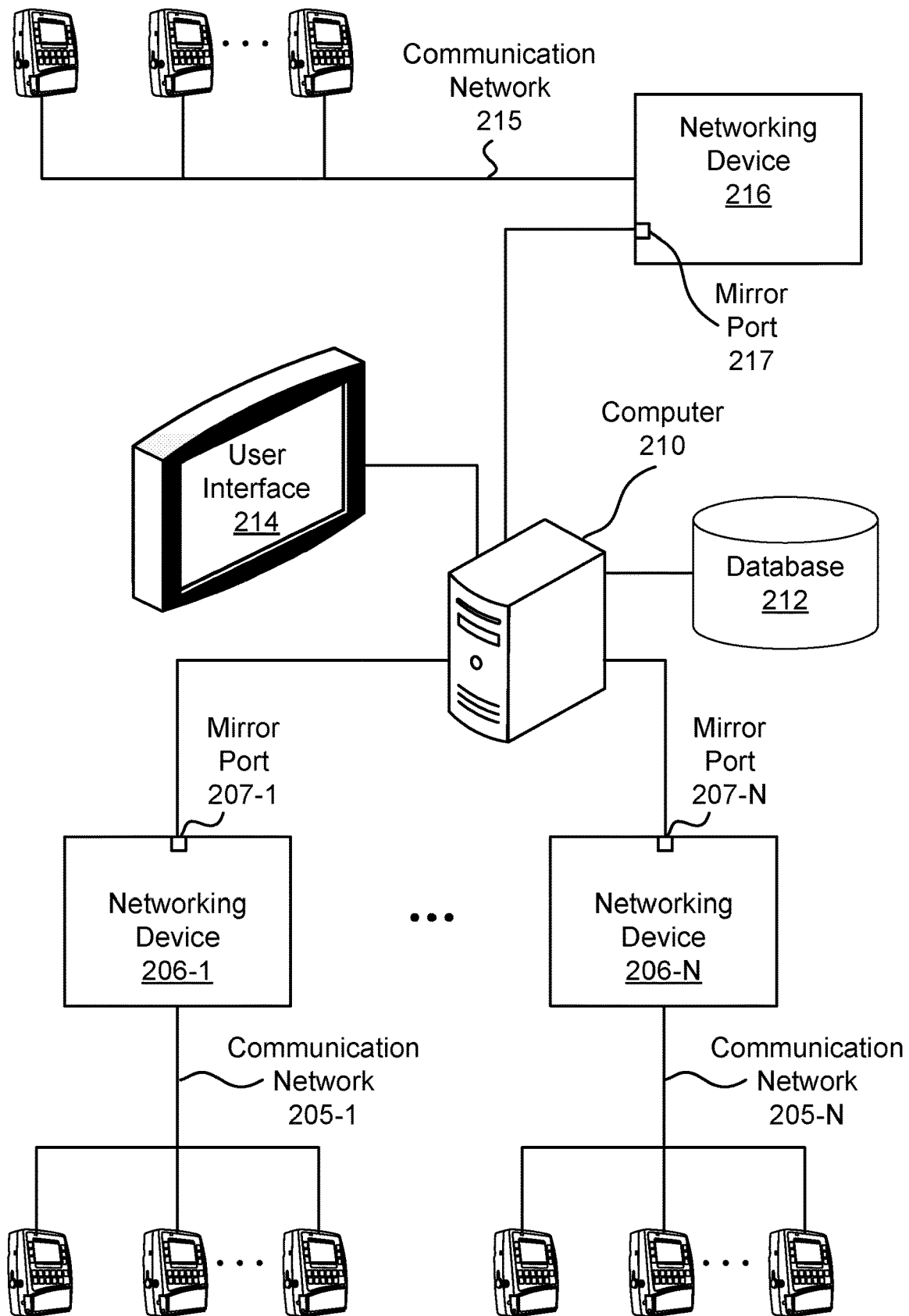
FIG. 9 illustrates one embodiment of a system configured to recommend a version of firmware for medical devices.

FIG. 9 illustrates one embodiment of a system configured to recommend a version of firmware for medical devices. The system includes a computer 210 that may include one or more of the computers described in this disclosure (e.g., the computer 400 illustrated in FIG. 18).

The computer 210 receives packets related to medical device activity at multiple medical facilities. In some embodiments, the packets are obtained from networking devices 206-1 to 206-N, which are connected to respective communication networks 205-1 to 205-N that belong to N respective different medical facilities (with networking device 206-$i$, $1 \leq i \leq N$, transmitting and/or receiving network traffic of medical facility i). Each medical facility may have a plurality of medical devices connected to its communication network, which may transmit and/or receive, packets containing medical activity data (e.g., data sent to or from an EMR of the medical facility and/or other computer systems of the medical facility). The networking devices 206-1 to 206-N have respective mirror ports 207-1 to 207-N, which duplicate the traffic on their respective communication networks. In other embodiments, at least some of the packets received by the computer 210 may be obtained through other means described in this disclosure, such as network TAPs, hosts set to operate in promiscuous mode, or plug-ins.

It is to be noted that the process of receiving packets by the computer 210 may be an ongoing process that may span long periods of time such as weeks, months, and even years, during which networking traffic comprising packets sent over the communication networks is analyzed by the computer 210.

The computer 210 performs DPI of the packets, and extracts from the results of the DPI of the packets versions of firmware installed on the medical devices. Optionally, the medical devices are of the same type and/or model (e.g., a certain model of infusion pumps or a certain brand of MRI machines) and are made by the same manufacturer. Versions of firmware may be determined in various ways from the results of the DPI. In one example, at least some of the packets include data transmitted during normal operations of a medical device, which identify a version of firmware (e.g., data transmitted by a medical device when utilized in a treatment of a patient may include the medical device's version of firmware as a data field). In another example, when a device's firmware is updated, it may run certain procedures and/or communicate with a certain server, and packets transmitted when such communications occur include information that is indicative of the version of firmware. In still another example, properties of packets transmitted by the medical device and/or to the medical device (e.g., a size of packets, their frequency, and/or protocol used) may be indicative of the version of firmware installed on the medical device. In some embodiments, information identifying versions of firmware installed on the medical devices, and optionally dates at which they were first detected, are stored in a database 212.

It is to be noted that referring to the computer 210 (or any other computer in this disclosure) in the singular form does mean the computer 210 is a single hardware unit, rather, the computer 210 should be considered a system that may include one or more hardware units. In one embodiment, the computer 210 includes multiple computers, such as having one or more computers at each of the medical facilities at which medical activity data is captured. Optionally, capturing and analyzing packets transmitted over each of the communication networks 205-1 to 205-N is done by a different hardware units, which are collectively referred to as the computer 210.

Given information about the versions of firmware installed on the medical devices at the N medical facilities (e.g., from the database 212), the computer 210 can calculate extents to which different versions of firmware were installed on the medical devices. Additionally, the computer 210 may determine for at least some of the different versions of firmware, dates they were first installed on at least some of the medical devices at the medical facilities. Optionally, this information is used to select, from among the different versions of firmware, a latest version of firmware for the medical devices. Optionally, the latest version of the firmware is a version whose extent of installation reaches a predetermined threshold. In one example, the extent of installation is a value indicative of a number and/or a proportion of the medical devices that have the latest version of firmware installed thereon. In another example, the extent of installation is a value indicative of a number and/or a proportion of the medical facilities that have medical devices with the latest version of firmware installed thereon. Optionally, the latest version is selected such that there is no other version of firmware that was first detected on a medical device at a later date than the latest version was detected, and whose extent of installation also reaches the predetermined threshold. Optionally, the extent of installation of the latest version is reported, e.g., via a message sent to a user interface 214.

Various types of values may be used for the predetermined threshold. In some embodiments, the predetermined threshold relates to the extent a version of firmware is installed on medical devices. Optionally, the predetermined threshold corresponds to at least one of the following: a minimal number of the medical devices (at the N medical facilities) having the latest version of the firmware installed thereon, and a minimal proportion of the medical devices having the latest version of the firmware installed thereon. In other embodiments, the predetermined threshold relates to the extent a version of firmware is installed on medical devices at different medical facilities. Optionally, the predetermined threshold corresponds to at least one of the following: a minimal number of facilities from among the N medical facilities having medical devices with an installation of the latest version of the firmware thereon, and a minimal proportion of the N medical facilities having medical devices with an installation of the latest version of the firmware thereon.

Once the latest version is selected by the computer 210, it can be recommended for installation on medical devices that have other versions of firmware installed thereon. In one embodiment, the computer 210 recommends an update of firmware installed on one or more medical devices at a certain medical facility to the latest version of firmware. Optionally, the certain medical facility is from among the N medical facilities. Alternatively, the certain medical facility may be some other medical facility, which is not among the N medical facilities.

In some embodiments, the computer 210 makes a recommendation to update firmware installed on the one or more medical devices at the certain medical facility to the latest version based on results of monitoring activity of medical devices at the certain medical facility. Optionally, the computer 210 receives certain packets transmitted over a communication network 215 of the certain medical facility, where the certain packets include data related to activity of certain medical devices at the certain medical facility. The computer 210 performs DPI of the certain packets and extracts, from results of the DPI of the certain packets, certain versions of firmware installed on the certain medical devices. The computer 210 selects, based on the certain versions of the firmware installed on the certain medical devices, the one or more medical devices, since a version of firmware installed on each of the one or more medical devices is older than the latest version of firmware. Optionally, the computer 210 also reports a duration it took to update the firmware installed on the one or more medical devices at the certain medical facility to the latest version.

In one embodiment, the computer 210 may monitor the progress of updating the firmware installed on the one or more medical devices at the certain medical facility. To this end, the computer 210 may receive additional packets transmitted over the communication network 215 after the recommendation to update the firmware was made, where the additional packets include data related to activity of the one or more medical devices at the certain medical facility. The computer 210 performs DPI of the additional packets and extracts, from results of the DPI of the additional packets, versions of firmware installed on the one or more medical devices, and identifies, based on said versions, a beginning of an updating process of the firmware installed on the one or more medical devices at the certain medical facility. In one example, the beginning of the update process may be based on detecting at least one medical device, from among the one or more medical devices, had had its firmware updated to the latest version. The computer 210 may keep track of which of the one or more medical devices has had its firmware updated to the latest version. In one embodiment, in an event that after a certain time, the computer 210 does not detect that a version of firmware installed on a certain medical device has been updated to the latest version, the computer 210 alerts about lack of updating of firmware of a certain medical device from among the one or more medical devices. For example, the computer 210 may send a message indicative of the lack of updating to a biomedical engineer. Optionally, the message is displayed on the user interface 214.

In another embodiment, monitoring the progress of the updating of the firmware may involve the computer 210 calculating, based on results of the DPI of the additional packets, durations the one or more medical devices at the certain medical facility were not available to treat patients due to the updating of the firmware. Optionally, an indication that a medical device is not available to treat patients may be that results of DPI of some packets indicate periods of time that the medical device was not online, and/or not in a state amenable to treat patients. Optionally, an indication that a medical device is not available to treat patients may be based on characteristics of communications of the medical device (e.g., the size of the packets it sends and/or receives, their frequency, etc.) Optionally, the computer 210 reports the aforementioned durations, e.g., by sending a notification that is displayed on the user interface 214.

In yet another embodiment, the computer 210 may compare the duration it took to update the firmware at the certain medical facility to durations of similar firmware updates (to the latest version) observed in at least some medical facilities from among the multiple medical facilities. Optionally, the durations of the similar updates may be determined from analysis of results of DPI of packets transmitted over communication networks of the at least some medical facilities. Optionally, a notification is sent by the computer 210 if the duration it took to update the firmware at the certain medical facility is significantly longer than the durations it took at the at least some medical facilities (e.g., the notification is sent if the duration is more than double than the average of the durations). In one example, the notification is presented on the user interface 214.

In order to ensure that the latest version of firmware is not hastily chosen, in some embodiments, performance of medical devices having the latest version installed thereon are monitored in order to determine the extent of operational errors that they have. The computer 210 calculates, based on information extracted from the results of the DPI of the packets, a value indicative of a rate of errors of medical devices with the latest version of firmware installed thereon. For example, the computer 210 can monitor how many error messages are transmitted by medical devices at the N medical facilities that have the latest version of firmware installed thereon. The computer 210 can then recommend the update to the latest version responsive to the rate of errors being below a certain threshold.

It is to be noted that some embodiments of the system illustrated in FIG. 4 may be designed such that they do not interfere with operations of medical devices and/or other computer systems of the N medical facilities or the certain medical facility, nor may they require changes be made to the computer systems or communication networks (beyond a mechanism for capturing the packets). Therefore, in some embodiments, the packets received by the computer 210 are not transmitted in response to a query of the computer 210 to an EMR system or any other computer system of the N medical facilities or the certain medical facility, or in response to a communication sent by the computer 210 (i.e., the packets are transmitted because of the routine operations of medical devices and not because of operations performed by the computer 210). Furthermore, the computer 210 need not be an integral part of the computing infrastructure of the N medical facilities or the certain medical facility. In one embodiment, the computer 210 does not have access to an EMR system to which at least some of the packets are sent. In another embodiment, the computer 210 does not have permission to access and/or command any at the medical devices of the N medical facilities or the certain medical facility. In yet another embodiment, the computer 210 does not transmit packets on any of the communication networks 205-1 to 205-N or communication network 215. In still another embodiment, the computer 210 is connected to a single networking device at each of the communication networks 205-1 to 205-N (the networking devices 206-1 to 206-N, respectively).

Figure 10:
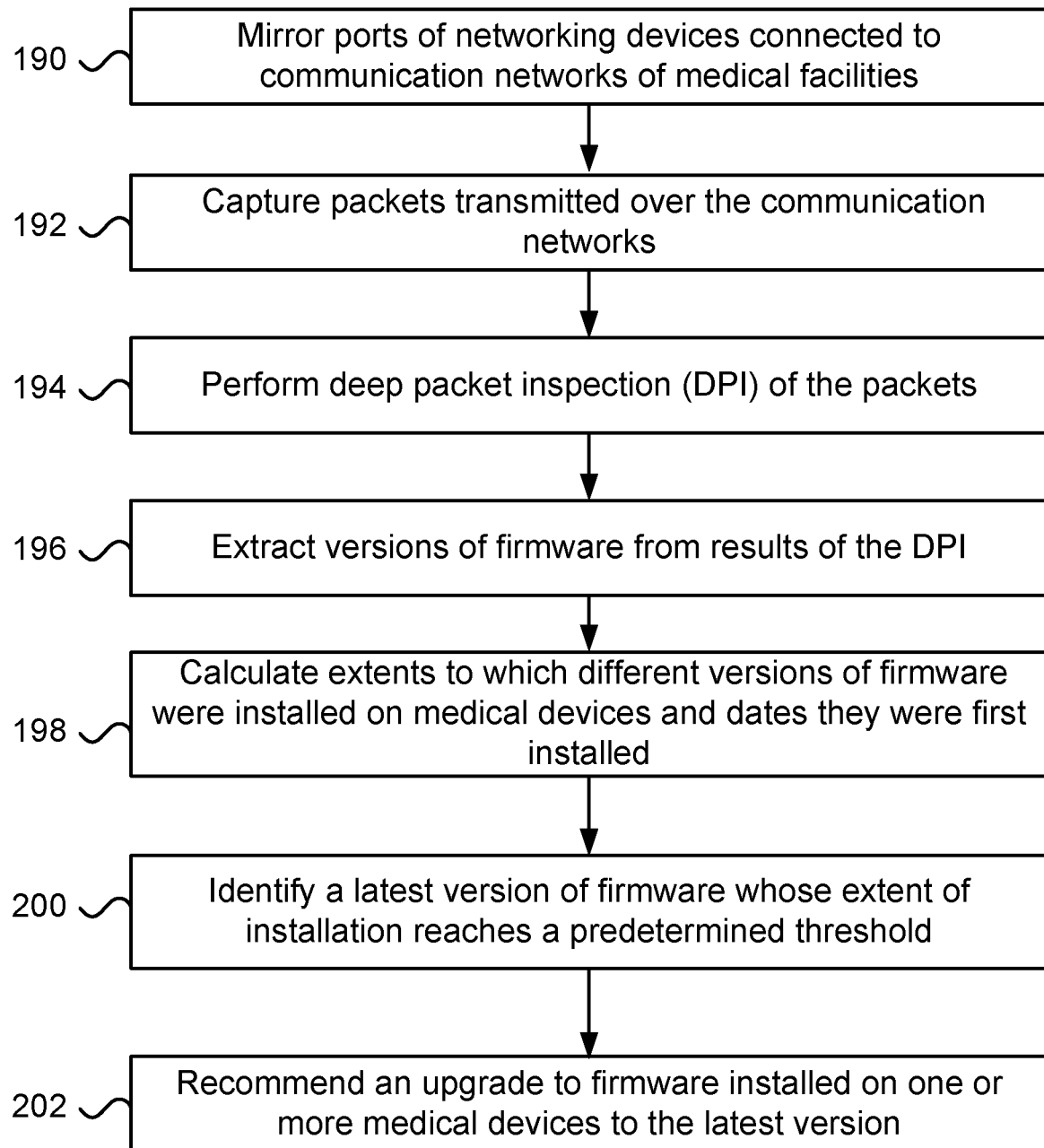
FIG. 10 illustrates steps involved in one embodiment of a method for recommending a version of firmware for medical devices.

FIG. 10 illustrates steps involved in one embodiment of a method for recommending a version of firmware for medical devices. The steps illustrated in FIG. 10 may be executed, in some embodiments, by systems modeled according to FIG. 9, which is described above. In some embodiments, instructions for implementing the method may be stored on a computer-readable medium, which may optionally be a non-transitory computer-readable medium. In response to execution by a computer system including a processor and memory (e.g., the computer 210 described above), the instructions cause the computer system to perform operations of the method.

In one embodiment, the method for recommending a version of firmware for medical devices includes at least the following steps:

In Step 192, capturing packets transmitted over communication networks of multiple medical facilities (e.g., the communication networks 205-1 to 205-N), where the packets include data related to activity of medical devices. Optionally, this step may be performed through continuous monitoring and capturing of traffic sent over the communication networks.

In Step 194, performing deep packet inspection (DPI) of the packets (e.g., by the computer 210, as described above).

In Step 196, extracting, from results of the DPI, versions of firmware installed on the medical devices. Optionally, information identifying versions of firmware installed on the medical devices, and optionally dates at which they were first detected, are stored in a database (e.g., the database 212).

In Step 198, calculating, based on the versions of firmware, extents to which different versions of firmware were installed on the medical devices.

In Step 200, identifying a latest version of firmware, from among the different versions, whose extent of installation reaches a predetermined threshold. In one example, the predetermined threshold corresponds to at least one of the following: a minimal number of the medical devices having the latest version of the firmware installed thereon, and a minimal proportion of the medical devices having the latest version of the firmware installed thereon. In another example, the predetermined threshold corresponds to at least one of the following: a minimal number of the medical devices having the latest version of the firmware installed thereon, and a minimal proportion of the medical devices having the latest version of the firmware installed thereon.

And in Step 202 recommending updating firmware installed on one or more medical devices at a certain medical facility to the latest version of firmware.

In some embodiments, the method may include optional Step 190, which involves receiving the packets captured in Step 192 utilizing port mirroring of ports on networking devices connected to the communication networks (e.g., the packets may be received via the mirror ports 207-1 to 207-N at the respective networking devices 206-1 to 206-N, as described above).

In order to ensure that the latest version of firmware is not hastily chosen, in some embodiments, performance of medical devices having the latest version installed thereon are monitored in order to determine the extent of operational errors that they have. To this end, some embodiments of the method described above may include a step of calculating, based on information extracted from the results of the DPI, a value indicative of a rate of errors of medical devices with the latest version of firmware installed thereon. In these embodiments, recommending to update firmware to the latest version is done responsive to the rate of errors being below a certain threshold.

In some embodiments, recommending to update firmware installed on one or more medical devices at a certain medical facility to the latest version is done based on results of monitoring activity of medical devices at the certain medical facility. To achieve this, embodiments of the method described above may include the following optional steps: receiving certain packets transmitted over a communication network of the certain medical facility (e.g., the communication network 215), where the certain packets include data related to activity of certain medical devices at the certain medical facility; performing DPI of the certain packet; extracting, from results of the DPI of the certain packets, certain versions of firmware installed on the certain medical devices; and selecting, based on the certain versions of the firmware installed on the certain medical devices, the one or more medical devices, where a version of firmware installed on each of the one or more medical devices is older than the latest version of firmware. Optionally, the method may also include a step of reporting a duration it took to update the firmware installed on the one or more medical devices at the certain medical facility to the latest version.

In one embodiment, the method may optionally include the following steps related to monitoring the progress of the updating of the firmware at the certain medical facility: receiving additional packets transmitted over the communication network 215 after the recommendation to update the firmware was made, where the additional packets include data related to activity of the one or more medical devices at the certain medical facility; performing DPI of the additional packets; extracting, from results of the DPI of the additional packets, versions of firmware installed on the one or more medical devices; identifying, based on said versions, a beginning of a process of updating the firmware installed on the one or more medical devices at the certain medical facility; and alerting about lack of updating of firmware of a certain medical device from among the one or more medical devices, responsive to determining that by a certain time since the beginning of the updating process, a version of firmware installed on the certain medical device has not been updated to the latest version.

In another embodiment, the method may optionally include a step of: calculating, based on results of the DPI of the additional packets, durations the one or more medical devices at the certain medical facility were not available to treat patients due to the update to the firmware. Optionally, the method may include a step of reporting said durations.

In yet another embodiment, the method may optionally include a step of: comparing the duration it took to update the firmware at the certain medical facility to durations of similar firmware updates (to the latest version) observed at least some medical facilities from among the multiple medical facilities. Optionally, the durations of the similar updates may be determined from analysis of results of DPI of packets transmitted over communication networks of the at least some medical facilities. Optionally, the method includes a step of sending a notification if the duration it took to update the firmware at the certain medical facility is significantly longer than the durations it took at the at least some medical facilities.

Figure 11:
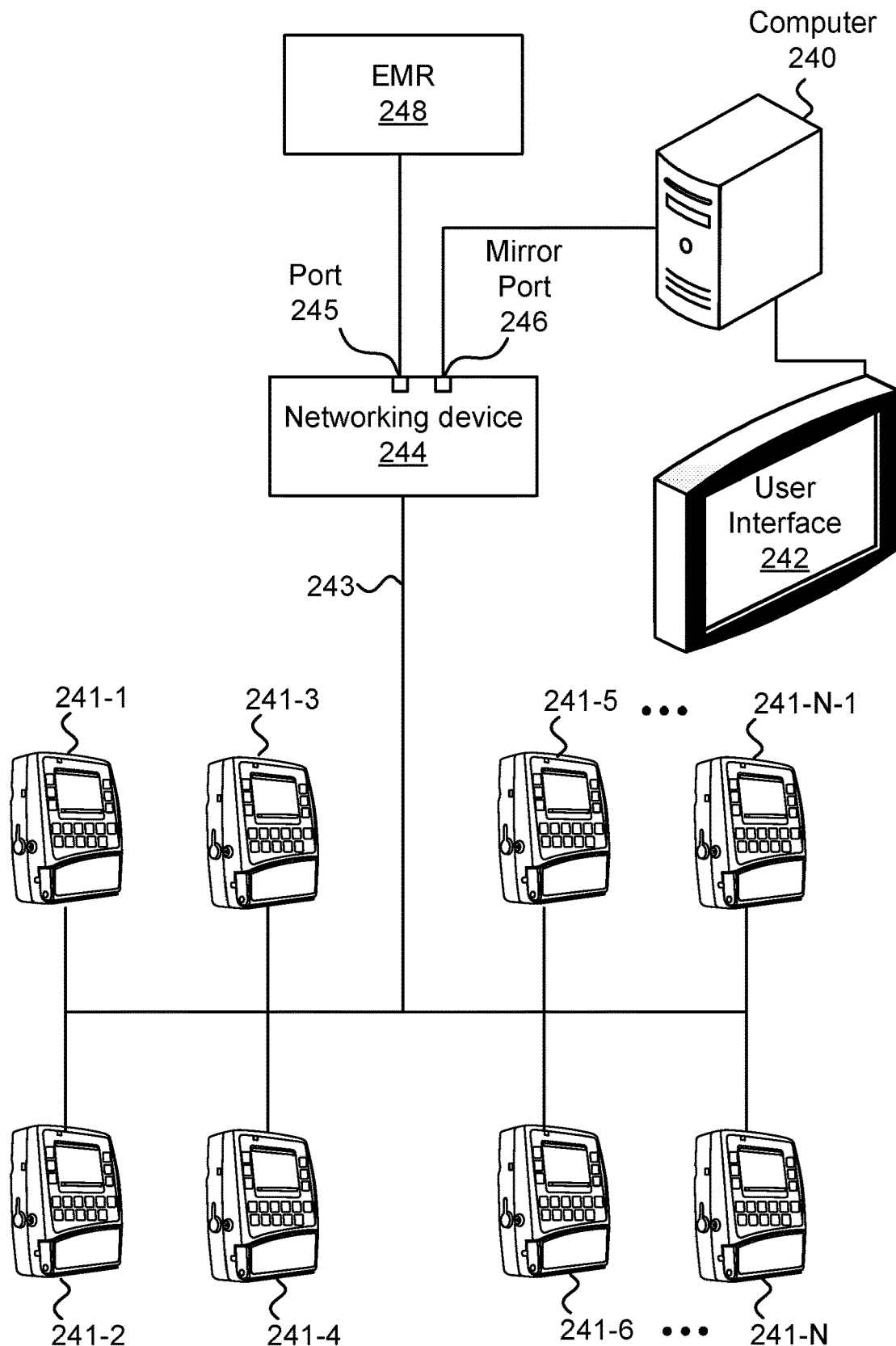
FIG. 11 illustrates one embodiment of a system configured to monitor drug library updating.

FIG. 11 illustrates one embodiment of a system configured to monitor drug library updating. In one embodiment, the system includes a computer 240, which receives and analyzes packets transmitted over a communication network 243. The computer 240 may include one or more of the computers described in this disclosure (e.g., computer 400 illustrated in FIG. 18). The system may optionally include other elements, such as a user interface 242. The computer 240 is configured to run one or more computer programs that cause it to perform operations described below (which may correspond to at least some of the steps of the method illustrated FIG. 13).

The computer 240 receives packets related to activity of infusion pump systems 241-1 to 241-N at a medical facility, which are transmitted over the communication network 243. In some embodiments, the packets are received via a mirror port 246 on a networking device 244. In other embodiments, the computer 240 may receive the packets using other mechanisms (e.g., a network TAP, a host set to operate in promiscuous mode, and plug-ins), as described further above in this disclosure.

It is to be noted that an "infusion pump system" may refer to various configurations of infusion pumps, which include both a single infusion pump unit, and a system comprising a server and/or control module that is connected to one or more pumping modules.

The networking device 244 is connected to a communication network 243 belonging to the medical facility. The N infusion pump systems 241-1 to 241-N are connected to the communication network 243 via a wired connection and/or a wireless connection. Optionally, the mirror port 246 mirrors network traffic that includes packets travelling through a port 245 of the networking device 244 and provides a copy of said traffic to the computer 240. Optionally, the packets travelling through port 245 include packets transmitted to, and/or transmitted by, an EMR 248 (or some other computer systems of the medical facility).

The computer 240 performs deep packet inspection (DPI) of the packets that include data related to the activity of the infusion pump system 241-1 to 241-N. Optionally, if results of the DPI of certain packets received by the computer 240 indicate that they are not related to activity of infusion pump systems (e.g., they were not sent by, or to, the infusion pump systems 241-1 to 241-N), the certain packets and/or results obtained from DPI of the certain packets are not utilized by the computer 240 for additional analysis.

The computer 240 extracts, from results of the DPI of the packets, identifiers of at least some of the infusion pump systems 241-1 to 241-N that had had their drug library updated to a new version. Optionally, the identifiers of at least some of the infusion pump systems 241-1 to 241-N are extracted from packets sent by the at least some of the infusion pump systems 241-1 to 241-N. For example, an infusion pump system may send a packet related to a treatment session provided to a patient, and the data payload of the packet may include an identifier of the infusion pump and an identifier of a version of the drug library installed thereon. Examples of an identifier of a version of a drug library may include a version number, a last update date, a file size of the drug library, and a digital signature (e.g., hash value) of the drug library. In another example, the drug library itself (i.e., its content) may be considered an indication of its version (thus different contents may correspond to different versions). Additionally or alternatively, the identifiers of the at least some of the infusion pump systems 241-1 to 241-N may be determined based on identifying that the new version of the drug library was sent to the at least some of the infusion pump systems 241-1 to 241-N. For example, the computer 240 may identify that certain packets include content of the new version of the drug library, which was sent to a certain infusion pump system with the intention of it being installed on the certain infusion pump system. In another example, the computer 240 may identify that an infusion pump system was sent a network destination from which it can download the new version of the drug library.

It is to be noted that the aforementioned analysis of the packets may be a continuous process. In one embodiment, the computer 240 may have access to a database that holds information related to the infusion pump systems 241-1 to 241-N, and is updated continuously ("on-the-fly") as versions of the drug library are identified in packets that are analyzed using DPI. Thus, the database can provide upon request a version of a drug library for each of the infusion pump systems 241-1 to 241-N at any time required by the computer 240.

The computer 240 may utilize information extracted from the results of the DPI of the packets to keep track of the progress of an update of drug libraries installed on infusion pump systems at the medical facility. In one embodiment, the computer 240 receives an indication when such an update process begins (e.g., from a biomedical engineer or technician). Optionally, the indication identifies the new version of the drug library (e.g., by providing an identifier of the new version and/or its content). In another embodiment, the computer 240 identifies that a new version of a drug library has been installed on at least a certain number of infusion pump systems, and infers from that the update process has begun (where the certain number may be one or a number greater than one). Optionally, the computer 240 determines that the version installed on the at least a certain number of infusion pump systems is a new version based on that version having a later creation date and/or a higher version number than other versions installed on infusion pump systems at the medical facility.

Following a beginning of an update process, the computer 240 may identify which of the infusion pump systems 241-1 to 241-N had not had its drug library updated yet to the new version. Optionally, if a certain infusion pump system had not had its drug library updated to the new version by a certain time, the computer 240 may alert about a lack of updating to the new version of a drug library of the certain infusion pump system. For example, the computer 240 may send a notification indicating the lack of updating of the certain infusion pump to a user interface 242 that may belong to a biomedical engineer, a technician, and/or some other employee of the medical facility.

Identifying the certain infusion pump system may be done in different ways. In one embodiment, when drug libraries start being updated (or even before the process begins), the computer 240 creates a list of all infusion pump systems 241-1 to 241-N, and then removes from the list any infusion pump system whose update is detected from the results of the DPI of the packets. Optionally, any infusion pump system that is still on the list after the certain time may be considered to have had an unacceptable delay to the updating, which should be notified about. In another embodiment, the computer 240 may create and update a list of all infusion pump systems that had been updated. After the certain time, this list may be compared to an inventory of all infusion pump systems at the medical facility in order to identify infusion pump systems that had yet to have their drug library updated.

There are various ways in which the certain time may be selected or set. In one embodiment, the certain time may be a predetermined parameter (e.g., set by an administrator at the medical facility). For example, the certain time may correspond to a day, a week, or even a month. In another embodiment, the certain time may be set by the system. For example, the certain time may be proportional to the time it took to update drug libraries of a certain portion of the infusion pump systems at the medical facility. For example, the certain time may be double the time it took to have 40% of the infusion pump system updated (or some other proportion such as 50%, 66%, or some other proportion).

The computer 240 may monitor utilization of infusion pump systems to ensure that infusion pump systems that have not been updated do not get used. In one embodiment, the computer 240 identifies, based on results DPI of one or more of the packets that were transmitted after the certain time, that the certain infusion pump system was being utilized in a treatment session. The computer 240 then sends a notification (e.g., to the user interface 242) indicating not to utilize the certain infusion pump system in a new treatment session until its drug library has been updated to the new version. Optionally, the computer 240 suggests to use an alternative infusion pump system, which has already had its drug library updated to the new version.

In some embodiments, the computer 240 may determine locations of the infusion pump systems 241-1 to 241-N based on results of the DPI of the packets. Optionally, the computer 240 determines the location of the certain infusion pump system based on DPI of the one or more of the packets, and provide the location in the notification it sends when it alerts about the lack of updating of the drug library of the certain infusion pump system. Optionally, the location of an infusion pump system refers to a physical location of a control module of the infusion pump system.

Figure 12:
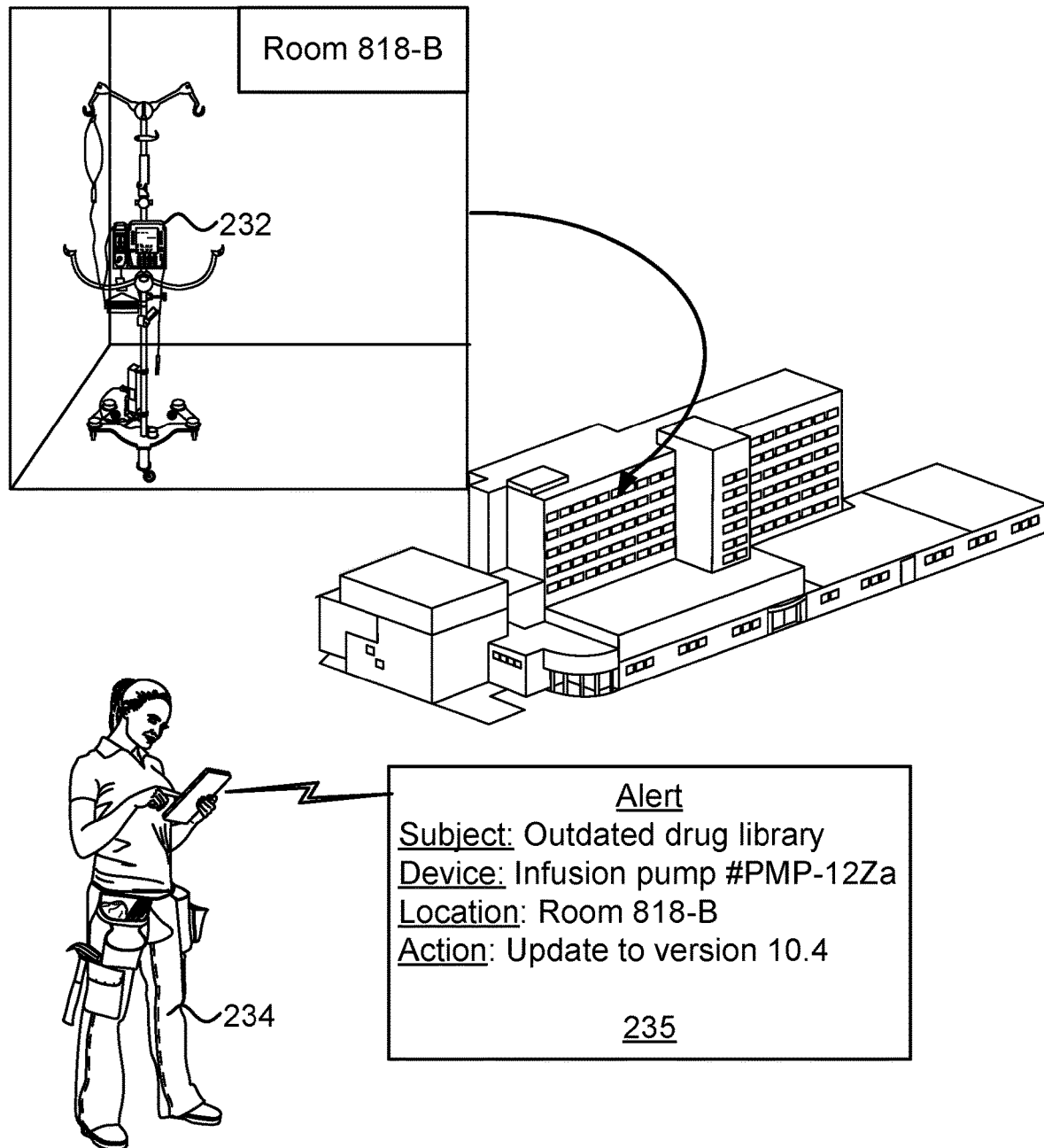
FIG. 12 illustrates a scenario in which an alert about an infusion pump system that has not had its drug library updated includes the location of the infusion pump system.

A scenario in which an alert about an infusion pump system includes the location of the infusion pump system is illustrated in FIG. 12, which illustrates how technician 234 receives alert 235 indicating a location (room 818-B in the figure) of a certain infusion pump system 232 that has not had its drug library updated to the new version yet.

In some embodiments, the computer 240 may alert about infusion pump systems that are not connected or not online. Optionally, the computer 240 identifies a specific infusion pump system, from among the infusion pump systems 241-1 to 241-N, which was not online after the certain time (and for which no indication about an update of the drug library was detected based on results of the DPI of the packets). In this event, the computer 240 may provide a notification indicating not to utilize the specific infusion pump system until its drug library is updated to the new version (e.g., by sending a notification to the user interface 242). Optionally, the computer 240 may look up and/or determine a last known location of the specific infusion pump system based on results of DPI of one or more of the packets that were transmitted before the certain time, and provide the last known location in the notification.

Through its monitoring of activity of the infusion pump systems 241-1 to 241-N, the computer 240 may determine when the process of updating the drug library has been completed. Optionally, the computer 240 makes such a determination based on additional results of DPI of additional packets transmitted over the communication network 243 after the certain time. Optionally, the additional results indicate that all the infusion pump systems that had not been updated by the certain time, have been updated by a later time. Optionally, the computer 240 sends a notification (e.g., to the user interface 242) indicating completion of the updating process of drug libraries on all of the infusion pump systems 241-1 to 241-N. Optionally, the notification includes the duration it took to update the drug libraries of the infusion pump systems 241-1 to 241-N.

In one embodiment, the computer 240 compares the duration of the drug libraries' updating at the medical facility to durations of updating drug libraries of infusion pump systems at multiple medical facilities. Optionally, the durations of updating drug libraries at other medical facilities is determined based on monitoring of network traffic over communication networks of the medical facilities and analyzing results of DPI of packets transmitted over those communication networks similar to the monitoring of traffic transmitted over the communication network 243 by the computer 240, as described above. Optionally, the comparison is indicative of whether the updating at the medical facility was faster or slower than updating of drug libraries at medical facilities with a similar number of infusion pump systems to update (e.g., medical facilities with ±25% infusion pump systems).

In some embodiments, the computer 240 may receive contents of drug libraries obtained from multiple medical facilities (e.g., through monitoring traffic comprising packets sent over communication networks of the multiple medical facilities, similar to the monitoring utilizing results of DPI of packets sent over the communication network 243). Optionally, the computer 240 compares parameters of the new version of the drug library (as detected based on results of the DPI of the packets transmitted over the communication network 243) with parameters of drug libraries used at the multiple medical facilities, as determined based on results of DPI of additional packets transmitted over communication networks of the multiple medical facilities. Optionally, the comparison involves detecting different operating parameters used at the medical facility compared to the multiple facilities. In one example, the comparison involves determining that a dosage limit for a certain drug used at the medical facility is higher (e.g., at least 25% higher) than similar dosage limits for the certain drug used at the multiple medical facilities.

It is to be noted that some embodiments of the system illustrated in FIG. 11 may be designed such that they do not interfere with operations of medical devices and/or other computer systems of the medical facility, nor may they require changes be made to the computer systems or communication networks (beyond a mechanism for capturing the packets). Therefore, in some embodiments, the packets received by the computer 240 are not transmitted in response to a query of the computer 240 to an EMR system or to any other computer system of the medical facility, and are not transmitted in response to a communication sent by the computer 240 (i.e., the packets are transmitted because of the routine operations of the infusion pump systems 241-1 to 241-N and not because of operations performed by the computer 240). Furthermore, the computer 240 need not be an integral part of the computing infrastructure of the medical facility. In one embodiment, the computer 240 does not have access to an EMR system to which at least some of the packets are sent. In another embodiment, the computer 240 does not have permission to access and/or command any of the infusion pump systems 241-1 to 241-N. In yet another embodiment, the computer 240 does not transmit packets over the communication network 243. In still another embodiment, the computer 240 is connected to a single networking device 244 that is connected to the communication network 243.

Figure 13:
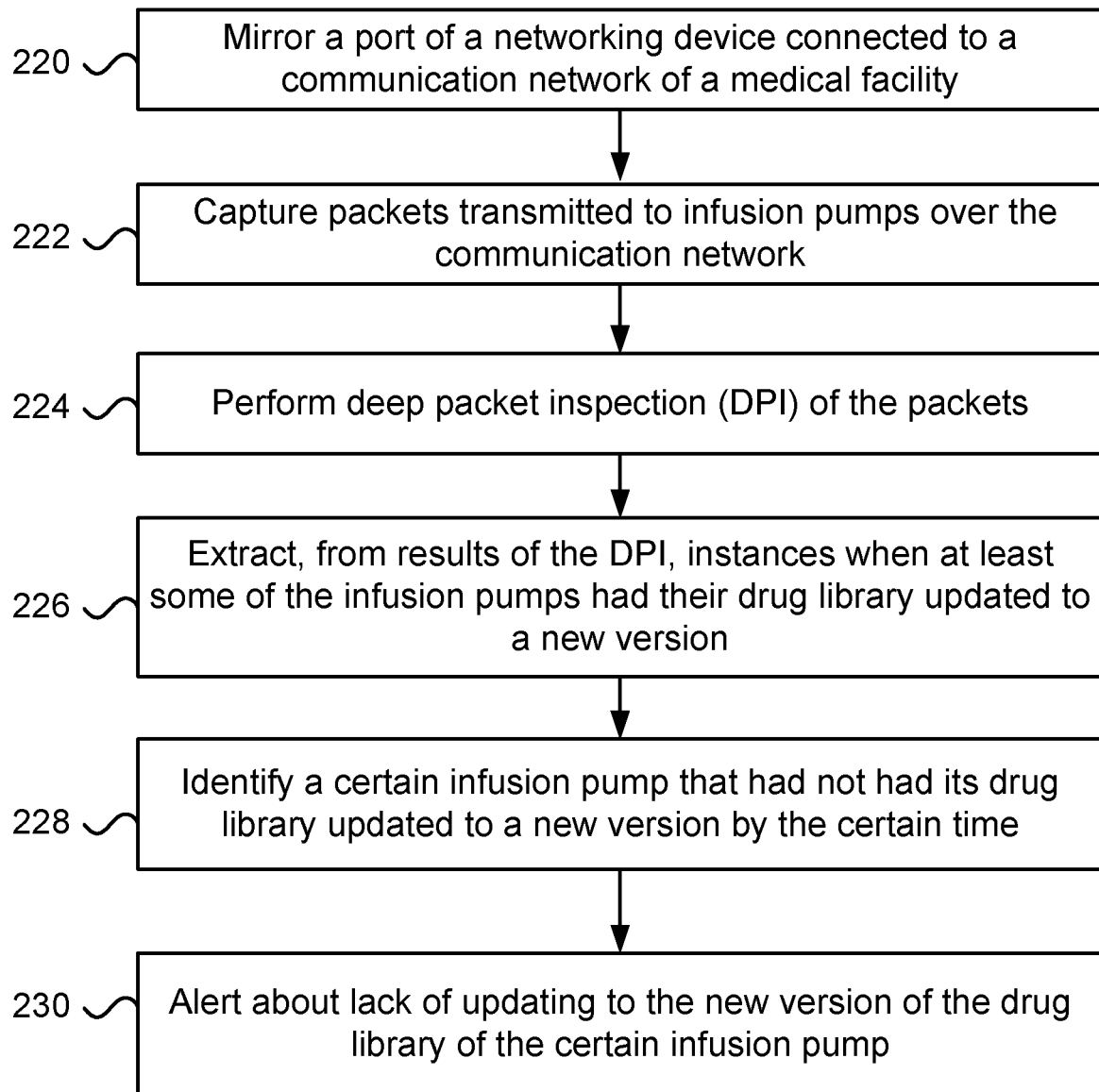
FIG. 13 illustrates steps involved in one embodiment of a method for monitoring drug library updating.

FIG. 13 illustrates steps involved in one embodiment of a method for monitoring drug library updating. The steps illustrated in FIG. 13 may be executed, in some embodiments, by systems modeled according to FIG. 11, as described above. In some embodiments, instructions for implementing the method may be stored on a computer-readable medium, which may optionally be a non-transitory computer-readable medium. In response to execution by a computer system including a processor and memory (e.g., the computer 240 described above), the instructions cause the computer system to perform operations of the method.

In one embodiment, the method for monitoring drug library updating includes at least the following steps:

In Step 222, capturing packets transmitted over a communication network (e.g., the communication network 243), as part of communications with the infusion pump systems 241-1 to 241-N. Optionally, this step may be performed through continuous monitoring and capturing of traffic sent over the communication network.

In Step 224, performing deep packet inspection (DPI) of the packets.

In Step 226, extracting, from results of the DPI of the packets, identifiers of at least some of the infusion pump systems that had had their drug library updated to a new version.

In Step 228, identifying, based on the identifiers, a certain infusion pump system that had not had its drug library updated to the new version by a certain time.

And in Step 230, alerting about a lack of updating to the new version of a drug library of the certain infusion pump system.

In some embodiments, the method may include optional Step 220, which involves receiving the packets captured in Step 222 utilizing port mirroring of a port on a networking device connected to the communication network (e.g., the packets may be received via the mirror port 246 that mirrors the port 245, as described above).

In one embodiment, the method described above may optionally include steps involving capturing additional packets, transmitted over the communication network, determining based on additional results of DPI of the additional packets that drug libraries of all infusion pump systems were updated to the new version, and providing a report indicating completion of drug libraries' updating. Optionally, the method may also include steps involving comparing the duration of the drug libraries' updating to durations of updating drug libraries of infusion pump systems at multiple medical facilities.

In another embodiment, the method described above may optionally include a step involving comparing parameters in the new version of the drug library with parameters of drug libraries used at multiple medical facilities, as determined based on results of DPI of additional packets transmitted over communication networks of the multiple medical facilities.

In one embodiment, the method may include the following steps: identifying, based on results of DPI of one or more packets that were transmitted after the certain time, that the certain infusion pump system was being utilized in a treatment session, and providing a notification indicating not to utilize the certain infusion pump system in a new treatment session until its drug library has been updated to the new version. Optionally, the method may also involve determining the location of the certain infusion pump system based on the results of the DPI of the one or more packets and providing the location in the notification.

In another embodiment, the method may optionally include the following steps: identifying a specific infusion pump, from among the infusion pumps, which was not online after the certain time, and providing a notification indicating not to utilize the specific infusion pump until its drug library has been updated to the new version. Optionally, the method may include steps involving determining a last known location of the specific infusion pump based on results of DPI of one or more packets that were transmitted before the certain time, and providing the last known location in the notification.

Figure 14:
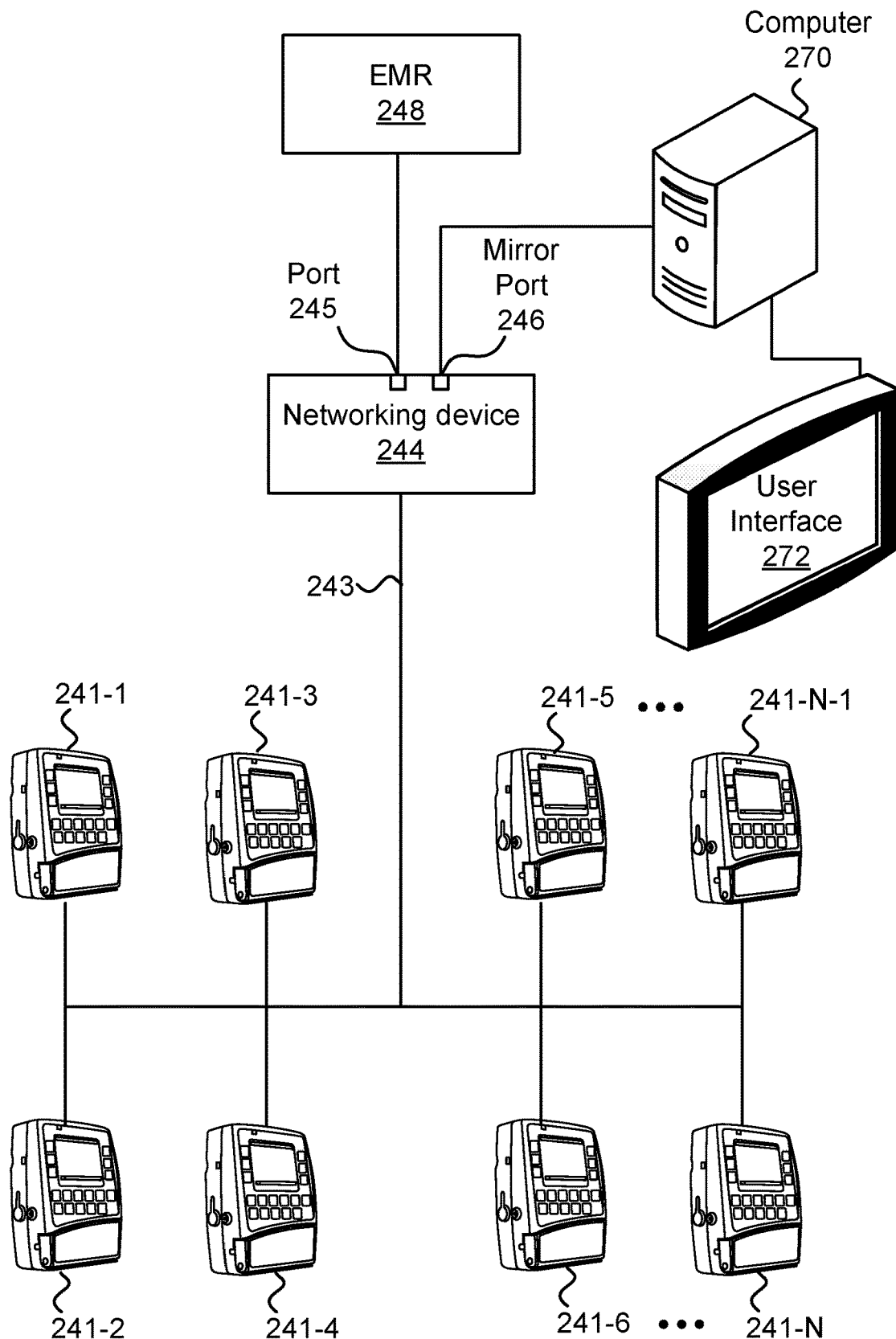
FIG. 14 illustrates one embodiment of a system configured to audit reported amounts of infused medications.

FIG. 14 illustrates one embodiment of a system configured to audit reported amounts of infused medications. In one embodiment, the system includes a computer 270, which receives and analyzes packets transmitted over the communication network 243. The computer 270 may include one or more of the computers described in this disclosure (e.g., computer 400 illustrated in FIG. 18). The system may optionally include other elements, such as a user interface 272. The computer 270 is configured to run one or more computer programs that cause it to perform operations described below (which may correspond to at least some of the steps of the method illustrated FIG. 15).

In a similar fashion to the computer 240, the computer 270 receives packets related to activity of the infusion pump systems 241-1 to 241-N at a medical facility, which are transmitted over the communication network 243. In some embodiments, the packets are received via the mirror port 246 on the networking device 244. In other embodiments, the computer 270 may receive the packets using other mechanisms (e.g., a network TAP, a host set to operate in promiscuous mode, and plug-ins.

The computer 270 performs deep packet inspection (DPI) of the packets related to the activity of the infusion pump system 241-1 to 241-N. Optionally, if results of the DPI of certain packets received by the computer 270 indicate that they are not related to activity of infusion pump systems (e.g., they were not sent by, or to, the infusion pump systems 241-1 to 241-N), the certain packets and/or results obtained from DPI of the certain packets are not utilized by the computer 270 for additional analysis.

The computer 270 extracts, from results of the DPI of the packets, values comprising dosages of medications delivered to patients during treatment sessions using the infusion pump systems 241-1 to 241-N. Optionally, the computer 270 may extract from the packets other information related to the treatment sessions, such as identifiers of patients, caregivers administering the treatment sessions, locations of the infusion pump systems, and more.

The packets from which the dosages are extracted may originate from various devices and/or have various addressees. In one embodiment, at least some of the dosages of the medications delivered to the patients are extracted from packets sent to infusion pump systems from a computer system at the medical facility, such as a computer terminal at a doctor's office or a nurse station. For example, a dosage of a medication may be extracted from a data payload of a packet that includes operating instructions sent to a control unit of an infusion pump system. In another embodiment, at least some of the dosages of the medications delivered to the patients are extracted from packets sent by infusion pump systems to other computer systems at the medical facility, such as the EMR 248. For example, a dosage of a medication may be extracted from a data payload of a packet that includes a report sent by an infusion pump system to the EMR 248.

It is to be noted that the aforementioned analysis of the packets may be a continuous process. In one embodiment, the computer 270 may have access to a database that holds information related amounts of medications provided at the medical facility, and is updated continuously ("on-the-fly"), as new values are related to dosages of the medications provided treatment sessions are obtained. Thus, the database can provide upon request reports on amounts of medications provided in treatment sessions at the medical facility in response to a query of the computer 270.

The computer 270 may utilize the values of dosages of medications delivered to patients, extracted from results of the DPI, to calculate amounts of the medications that were provided to the patients during the treatment sessions (referred to herein as "actual amounts"). Optionally, the actual amounts include cumulative quantities of each of the medications that were provided in treatment sessions at the medical facility during a certain period (e.g., a certain day, a certain week, a certain month, or a certain year). Optionally, the actual amounts may be cumulative quantities of each of the medications that were provided since a certain date (e.g., the certain date may correspond to the last time an evaluation of medication utilization was performed at the medical facility).

The computer 270 also receives amounts of the medications reported as being provided to the patients during the treatment sessions (referred to as "reported amounts"). Optionally, the reported amounts corresponding to the same periods as the actual amounts. Optionally, the reported amounts are not derived from analysis of the packets utilized to calculate the actual amounts. Optionally, the reported amounts are not generated based on data provided by the infusion pump systems 241-1 to 241-N. Optionally, the reported amounts include reports of cumulative quantities of each of the medications supposedly provided in treatment sessions at the medical facility during a certain period (e.g., a certain day, a certain week, a certain month, or a certain yea). Optionally, the reported amounts include reports of cumulative quantities of each of the medications that were supposedly provided since a certain date (e.g., the certain date may correspond to the last time an evaluation of medication utilization was performed at the medical facility).

In one embodiment, the computer 270 calculates the reported amounts based on indications of changes in amounts of the medications in an inventory of the medical facility, which were received from a computer system having access to state information of said inventory. For example, the reported amount of a medication corresponding to a certain period may be calculated by subtracting the an amount of the medication in the inventory at the end of the certain period from the amount of the medication in the inventory at the beginning of the certain period, and adding to that number any increase in the inventory (e.g., due to restocking) that occurred in between.

In order to audit reported amounts of infused medications, in some embodiments, the computer 270 performs a comparison between the actual amounts and the reported amounts. Optionally, the comparison is done with regards to a certain period, and the actual amounts being compared describe amounts of medications that are determined based on analysis of the packets sent over communication network 243, while the reported amounts being compared describe amounts of medications that were supposedly utilized based on an inventory and/or some other source of information (which does not include the packets). In one example, the comparison may be indicative of a difference in quantities between the actual amounts and the reported amounts. In another example, the comparison may be indicative of a ratio in quantities between the actual amounts and the reported amounts. Optionally, a result of a comparison between the actual amounts and the reported amounts is forwarded by the computer 270. For example, the result may describe the comparison (e.g., via a table), which is presented on a user interface, such as user interface 272, which may belong to an administrator at the medical facility. In some embodiments, the forwarded report indicates for each of the medications, a difference between a reported amount for the medication and an actual amount for the medication (which is derived from results of the DPI of the packets, as mentioned above). Optionally, the report highlights medications for which the difference between the actual amount and the reported amount reaches a threshold.

In one embodiment, if a difference between the actual amounts and the reported amounts reaches a threshold, the computer 270 will issue an alert thereof. For example, if for one or more medications, the actual amounts are lower than the reported amounts by 10% or more, this may indicate theft of the one or more medications, which an administrator at the medical facility should be aware of.

A comparison between the actual amounts and the reported amounts may be done in various ways. In particular, the comparison may be stratified and performed with respect to certain parameters, such as care areas were treatments were administered or caregivers who administered the treatments. Optionally, performing a comparison between stratified values can enable identification of certain problematic elements (such as a certain care area or caregiver) for which discrepancies between the reported amounts and the actual amounts are especially high.

In some embodiments, the computer 270 may compare between the actual amounts and the reported amounts, when these values are broken down (stratified) with respect to each care area (e.g., ICU, pediatrics, dialysis, etc.). The computer 270 extracts, from the results of the DPI of the packets, indications of care areas at which the treatments sessions were conducted (e.g., by determining from the results of the DPI the locations of the infusion pump systems used in the treatments sessions). The computer 270 can then calculate, based on the values comprising the dosages of medications and these indications, amounts of the medications that were provided to patients during the treatment sessions at each of the care areas (referred to herein as "actual care area amounts"). The computer 270 may also receive amounts of the medications reported as being provided to the patients during the treatment sessions in each care area (referred to herein as "reported care area amounts"). For example, the received amounts may be compiled from an EMR system that stores records of treatment sessions at the medical facility. This now enables the computer 270 to make a comparison for each of the care areas, and forward a result of a comparison between the actual care area amounts and the reported care area amounts. Optionally, the computer 270 may identify a certain care area for which a discrepancy between the actual amount and reported amount for a certain medication is larger than a threshold, and report the certain care area. Optionally, for most of the other care areas at the medical facility, a discrepancy between the actual amount and reported amount for the certain medication is below the threshold.

In other embodiments, the computer 270 may compare between the actual amounts and the reported amounts, when these values are broken down (stratified) with respect to caregiver who administered the treatment sessions in which the medications were provided. The computer 270 extracts, from the results of the DPI, identities of caregivers that administered the treatment sessions (e.g., they may be required to enter a personal code in order to administer the treatment). The computer 270 can then calculate, based on the values comprising the dosages of medications and these identities, amounts of the medications that were provided to patients during the treatment sessions by each of the caregivers (referred to herein as "actual caregiver amounts"). The computer 270 may also receive amounts of the medications reported as being provided to the patients during the treatment sessions administered by each of the caregivers (referred to herein as "reported caregiver amounts"). For example, the received amounts may be compiled from an EMR system that stores records of treatment sessions at the medical facility (which include indications of the caregivers who administered the treatment sessions). This now enables the computer 270 to make a comparison for each of the caregiver, and forward a result of a comparison between the actual caregiver amounts and the reported caregiver amounts. Optionally, the computer 270 may identify a certain caregiver for whom a discrepancy between the actual amount and reported amount for a certain medication is larger than a threshold, and report the certain caregiver. Optionally, for most of the other caregivers at the medical facility, a discrepancy between the actual amount and reported amount for the certain medication is below the threshold.

Results of the comparison between the actual amounts and the reported amounts may be evaluated with respect to similar comparisons that were performed at other medical facilities. Such an evaluation can assist in identifying whether a difference between the actual amounts and the reported amounts at the medical facility is significant. For example, if the magnitude of the difference is greater than the magnitude of similar differences at other medical facilities, this may mean that something irregular is happening at the medical facility.

In order to enable a comparison of a difference between the actual amounts and the reported amounts with similar difference at other medical facilities, in one embodiment, the computer 270 receives additional packets that were transmitted over communication networks of multiple medical facilities. The additional packets include data related to activity of additional infusion pump systems. The computer 270 performs DPI of the additional packets, and extracts, from results of the DPI of the additional packets, additional values that include dosages of medications delivered to additional patients during additional treatment sessions using the additional infusion pump systems. The computer 270 calculates, based on the additional values, amounts of the medications that were provided to the additional patients during the additional treatment sessions (referred to herein as "additional actual amounts"). Additionally, the computer 270 receives amounts of the medications reported as being provided to the patients during the additional treatment sessions (referred to herein as "additional reported amounts"). For example, the additional reported amounts may be obtained from monitoring changes to medication inventories at the multiple medical facilities. The computer 270 can then report a comparison between (i) a magnitude of a difference between the actual amounts and the reported amounts and (ii) magnitudes of differences between the additional actual amounts and the additional reported amounts. Optionally, the report includes an indication of a statistical significance of the magnitude of the difference between the actual amounts and the reported amounts, which is based on a distribution of the magnitudes of differences between the additional actual amounts and the additional reported amounts. For example, the statistical significance may be in the form of a p-value or an indication of how many standard deviations the difference observed at the medical facility is from the mean of similar differences calculated for the multiple medical facilities.

The comparison between the magnitude of the difference between the actual amounts and the reported amounts at the medical facility and the magnitudes of differences between the additional actual amounts and the additional reported amounts, may also be broken down according to care area. To this end, in some embodiments, the computer 570 reports a comparison between (i) a magnitude of a difference between the actual amounts and the reported amounts for a certain care area at the medical facility and (ii) magnitudes of differences between the additional actual amounts and the additional reported amounts for the certain care area at the multiple medical facility.

It is to be noted that referring to the computer 270 (or any other computer in this disclosure) in the singular form does mean the computer 270 is a single hardware item, rather, the computer 270 should be considered a system that may include one or more hardware units. In one embodiment, the computer 270 includes multiple computers, such as having one or more computers at each of the multiple medical facilities at which the aforementioned medical activity data, related to infusion pump systems, is captured. Optionally, capturing and analyzing the additional packets transmitted over each of the communication networks of the multiple facilities may be done by a different hardware element, which collectively can be referred to as computer 270.

Data obtained from other medical facilities may be utilized to analyze differences that relate to a certain medication. In one embodiment, the computer 270 receives additional packets that were transmitted over communication networks of multiple medical facilities, where the additional packets include data related to activity of additional infusion pump systems. The computer performs DPI of the additional packets and extracts, from results of the DPI of the additional packets, additional values that include dosages of a certain medication delivered to additional patients during additional treatment sessions using the additional infusion pump systems. The computer 270 calculates, based on the additional values, amounts of the certain medication that were provided to the additional patients during the additional treatment sessions (referred to as "certain additional actual amounts"). Additionally, the computer 270 receives amounts of the medications reported as being provided to the patients during the additional treatment sessions (referred to as "certain additional reported amounts"). The computer 270 reports a comparison between (i) a magnitude of a difference between amount of the certain medication provided to the patients during the treatment sessions and amount of the certain medication reported as being provided to the patients during the treatment sessions (at the medical facility), and (ii) magnitudes of differences between the certain additional actual amounts and the certain additional reported amounts.

It is to be noted that some embodiments of the system illustrated in FIG. 14 may be designed such that they do not interfere with operations of medical devices and/or other computer systems of the medical facility, nor may they require changes be made to the computer systems or communication networks (beyond a mechanism for capturing the packets). Therefore, in some embodiments, the packets received by the computer 270 are not transmitted in response to a query of the computer 270 to an EMR system or to any other computer system of the medical facility, and are not transmitted in response to a communication sent by the computer 270 (i.e., the packets are transmitted because of the routine operations of the infusion pump systems 241-1 to 241-N and not because of operations performed by the computer 270). Furthermore, the computer 270 need not be an integral part of the computing infrastructure of the medical facility. In one embodiment, the computer 270 does not have access to an EMR system to which at least some of the packets are sent. In another embodiment, the computer 270 does not have permission to access and/or command any of the infusion pump systems 241-1 to 241-N. In yet another embodiment, the computer 270 does not transmit packets over the communication network 243. In still another embodiment, the computer 270 is connected to a single networking device 244 that is connected to the communication network 243.

Figure 15:
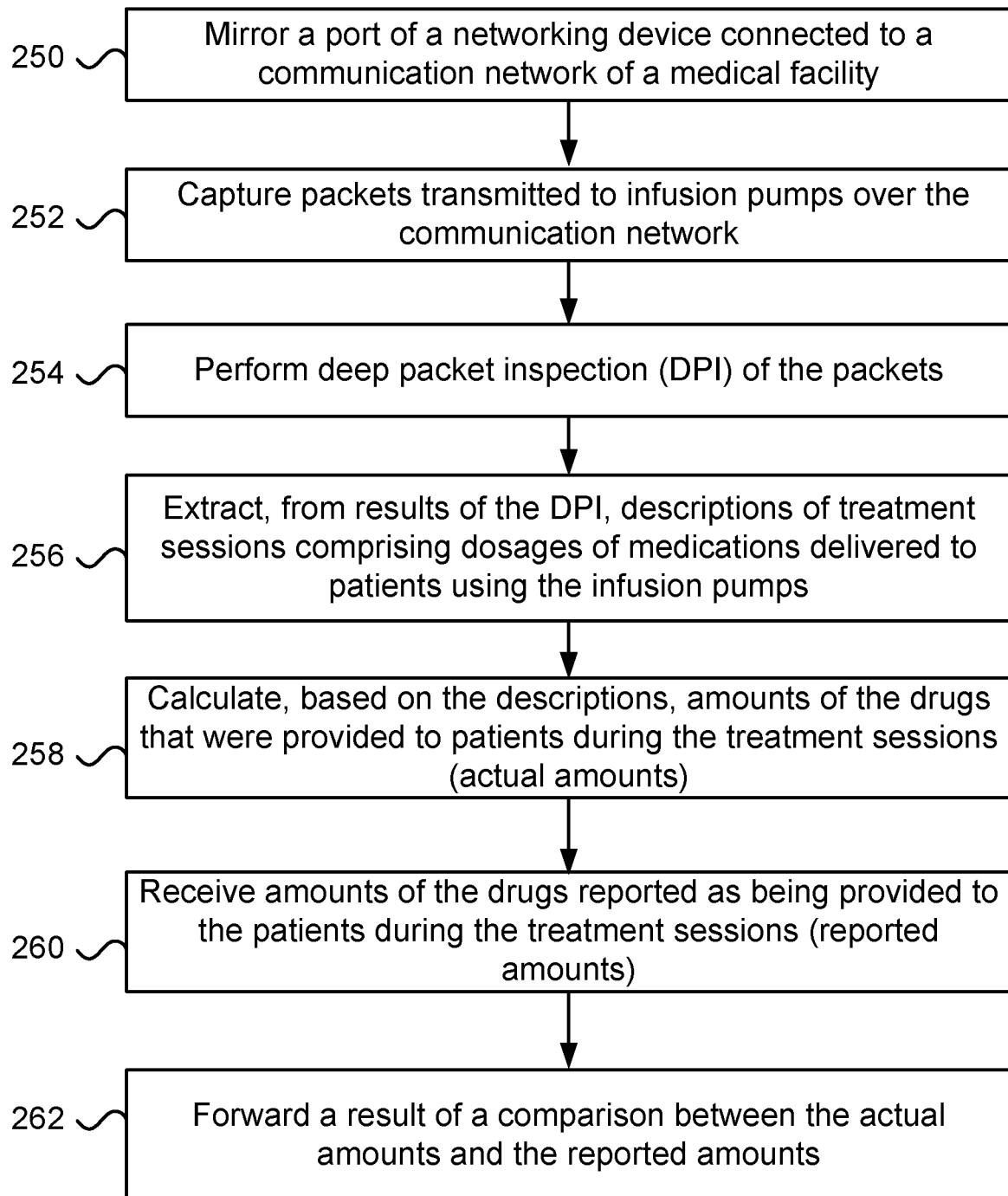
FIG. 15 illustrates steps involved in one embodiment of a method for auditing reported amounts of infused medications.

FIG. 15 illustrates steps involved in one embodiment of a method for auditing reported amounts of infused medications. The steps illustrated in FIG. 15 may be executed, in some embodiments, by systems modeled according to FIG. 14, as described above. In some embodiments, instructions for implementing the method may be stored on a computer-readable medium, which may optionally be a non-transitory computer-readable medium. In response to execution by a computer system including a processor and memory (e.g., the computer 270 described above), the instructions cause the computer system to perform operations of the method.

In one embodiment, the method for auditing reported amounts of infused medications includes at least the following steps:

In Step 252, capturing packets transmitted over a communication network (e.g., the communication network 243), as part of communications with the infusion pump systems 241-1 to 241-N. Optionally, this step may be performed through continuous monitoring and capturing of traffic sent over the communication network.

In Step 254, performing deep packet inspection (DPI) of the packets.

In Step 256, extracting, from results of the DPI, values comprising dosages of medications delivered to patients during treatment sessions using the infusion pump systems.

In Step 258, calculating, based on the values, amounts of the medications that were provided to the patients during the treatment sessions (actual amounts).

In Step 260, receiving amounts of the medications reported as being provided to the patients during the treatment sessions (reported amounts). Optionally, the reported amounts are calculated based on indications of changes in amounts of the medications in an inventory of the medical facility, which were received from a computer system having access to state information of said inventory.

And in Step 262, forwarding a result of a comparison between the actual amounts and the reported amounts. Optionally, the forwarded result indicates for each of the medications, a difference between a reported amount for the medication and an actual amount for the medication (which is derived from results of the DPI of the packets, as mentioned above). Optionally, the report highlights medications for which the difference between the actual amount and the reported amount reaches a threshold.

In some embodiments, the method may include optional Step 250, which involves receiving the packets captured in Step 252 utilizing port mirroring of a port on a networking device connected to the communication network (e.g., the packets may be received via the mirror port 246 that mirrors the port 245, as described above).

Results of the comparison between the actual amounts and the reported amounts may be stratified according to care area. In one embodiment, the method may optionally include the following steps: extracting, from the results of the DPI, indications of care areas at which the treatments sessions were conducted; calculating, based on the values and the indications, amounts of the medications that were provided to patients during the treatment sessions at each of the care areas (actual care area amounts); receiving amounts of the medications reported as being provided to the patients during the treatment sessions in each care area (reported care area amounts); and forwarding a result of a comparison between the actual care area amounts and the reported care area amounts.

Results of the comparison between the actual amounts and the reported amounts may be stratified according to caregiver. In one embodiment, the method may optionally include the following steps: extracting, from the results of the DPI, identities of caregivers that administered the treatment sessions; calculating, based on the values and the identities, amounts of the medications that were provided to patients during the treatment sessions by each of the caregivers (actual caregiver amounts); receiving amounts of the medications reported as being provided to the patients during the treatment sessions administered by each of the caregivers (reported caregiver amounts); and forwarding a result of a comparison between the actual caregiver amounts and the reported caregiver amounts.

Results of the comparison between the actual amounts and the reported amounts may be evaluated with respect to similar comparisons that were performed at other medical facilities. In one embodiment, the method may optionally include the following steps: capturing additional packets transmitted over communication networks of multiple medical facilities, where the additional packets include data related to activity of additional infusion pump systems; performing DPI of the additional packets; extracting, from results of the DPI of the additional packets, additional values that include dosages of medications delivered to additional patients during additional treatment sessions using the additional infusion pump systems; calculating, based on the additional values, amounts of the medications that were provided to the additional patients during the additional treatment sessions (additional actual amounts); receiving amounts of the medications reported as being provided to the patients during the additional treatment sessions (additional reported amounts); and reporting a comparison between (i) a magnitude of a difference between the actual amounts and the reported amounts and (ii) magnitudes of differences between the additional actual amounts and the additional reported amounts.

Data obtained from other medical facilities may be utilized to analyze differences that relate to a certain medication. In one embodiment, the method may optionally include the following steps: capturing additional packets transmitted over communication networks of multiple medical facilities, where the additional packets include data related to activity of additional infusion pump systems; performing DPI of the additional packets; extracting, from results of the DPI of the additional packets, additional values that include dosages of a certain medication delivered to additional patients during additional treatment sessions using the additional infusion pump systems; calculating, based on the additional values, amounts of the certain medication that were provided to the additional patients during the additional treatment sessions (additional actual amounts); receiving amounts of the medications reported as being provided to the patients during the additional treatment sessions (additional reported amounts); and reporting a comparison between (i) a magnitude of a difference between amount of the certain medication provided to the patients during the treatment sessions and amount of the certain medication reported as being provided to the patients during the treatment sessions, and (ii) magnitudes of differences between the additional actual amounts and the additional reported amounts.

Figure 16:
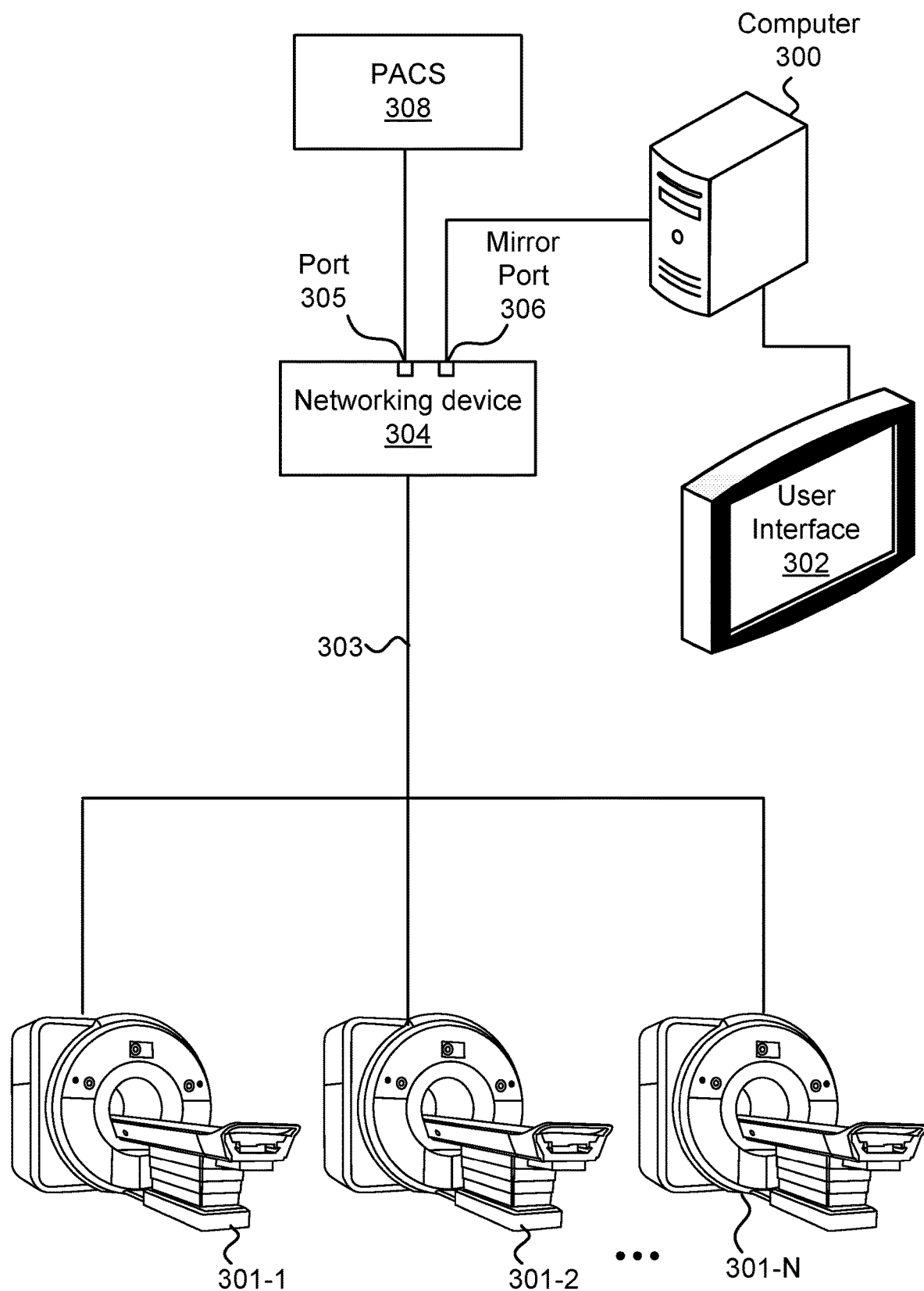
FIG. 16 illustrates one embodiment of a system configured to calculate prevalence of repeated medical imaging.

FIG. 16 illustrates one embodiment of a system configured to calculate prevalence of repeated medical imaging. In one embodiment, the system includes a computer 300, which receives and analyzes packets transmitted over a communication network 303. The computer 300 may include one or more of the computers described in this disclosure (e.g., computer 400 illustrated in FIG. 18). The system may optionally include other elements, such as a user interface 302. The computer 300 is configured to run one or more computer programs that cause it to perform operations described below (which may correspond to at least some of the steps of the method illustrated FIG. 17).

The computer 300 receives packets related to activity of one or more medical imaging devices denoted 301-1 to 301-N at a medical facility. The packets include data related to operation of one or more medical imaging devices 301-1 to 301-N. Optionally, at least of the packets are sent according to the Digital Imaging and Communications in Medicine (DICOM) standard.

It is to be noted that the use of the index "N" above is intended to include the case where N=1. Thus, even though multiple medical imaging devices are illustrated in FIG. 16, some embodiments may involve a single medical imaging device.

In some embodiments, the packets are received via a mirror port 306 on a networking device 304. In other embodiments, the computer 300 may receive the packets using other mechanisms (e.g., a network TAP, a host set to operate in promiscuous mode, and plug-ins), as described further above in this disclosure.

The networking device 304 is connected to a communication network 303 belonging to the medical facility. The N medical imaging devices 301-1 to 301-N are connected to the communication network 303 via a wired connection and/or a wireless connection. Optionally, the mirror port 306 mirrors network traffic that includes packets travelling through a port 305 of the networking device 304 and provides a copy of said traffic to the computer 300. Optionally, the packets travelling through port 305 include packets transmitted to, and/or transmitted by, Picture Archiving and Communication System (PACS) server 308 or some other computer systems of the medical facility such as an EMR.

In some embodiments, the packets are transmitted as part of routine operations of the medical imaging devices 301-1 to 301-N (e.g., some packets may include image data and/or other DICOM-compliant data), and not as a result of operations of the computer 300. In one example, the packets are not transmitted in response to a query of the packets are not transmitted in response to a communication sent by the computer 300 (e.g., to the medical imaging devices 301-1 to 301-N).

The computer 300 performs deep packet inspection (DPI) of the packets related to the activity of the one or more medical imaging devices 301-1 to 301-N. Optionally, if results of the DPI of certain packets received by the computer 300 indicate that they are not related to activity of medical imaging devices (e.g., they were not sent by, or to, the one or more medical imaging devices 301-1 to 301-N), the certain packets and/or results obtained from DPI of the certain packets are not utilized by the computer 300 for additional analysis.

The computer 300 extracts, from results of the DPI of the packets, values indicative of medical images acquired using the one or more medical imaging devices 301-1 to 301-N. Optionally, the values include one or more of the following: patient identifiers, medical imaging device identifiers, identifiers of body parts being image, parameters used to run imaging devices, and/or dates and times the medical images were taken. Optionally, the values are obtained from headers and/or data payloads of at least some of the packets which were sent using the DICOM standard. Additionally or alternatively, the values are obtained from headers and/or data payloads of certain packets sent according to some other standard.

It is to be noted that the collection and analysis of the packets described above may be an ongoing process in which data related to activity of the medical imaging devices 301-1 to 301-N is collected over a period of time, such as at least one day, at least one week, at least one month, and even over a year. Collecting data over a long period enables to more accurately determine the prevalence of repeated medical imaging (and with higher significance), compared to analysis of data collected over relatively short periods. Additionally, collecting and analyzing a large body of data may enable to stratify results, as discussed in more detail below.

The computer 300 utilizes the values extracted from the results of the DPI of the packets to identify instances of repeated medical imaging. Optionally, an instance of a repeated image involves acquiring images of the same patient and body part multiple times, utilizing a certain type of medical imaging device within a predetermined period. Optionally, a certain type may refer to using a specific imaging technology (e.g., an MRI device may be a different type than an X-RAY). Optionally, a certain type of device may refer to a device of a certain manufacturer and model (e.g., a "GE 1.5T Optima"). Optionally, the predetermined period is shorter than one week. Optionally, the predetermined period is shorter than one day. Optionally, the predetermined period is shorter than two hours.

The computer 300 may utilize identified instances of repeated medical images to calculate a value indicative of the prevalence of repeated medical imaging. In one example, the value is indicative of the proportion of images that are considered repeated medical images. In another example, the value may be indicative of the proportion of patients who were subjected to repeated imaging. In still another example, the value may be indicative of the amount of time spent acquiring medical images that are considered instances repeated medical imaging. Optionally, the value is forwarded to a user interface 302 (e.g., a terminal of an administrator at the medical facility).

In one embodiment, the computer 300 sends an alert about excessive repeated medical imaging responsive to the prevalence reaching a predetermined threshold. Optionally, the predetermined threshold is set to a value such as 6%, 8%, 10%, 12%, 15%, or more. Optionally, the computer 300 calculates the predetermined threshold based values indicative of prevalence of repeated medical imaging at other medical facilities. Optionally, values indicative of the prevalence at the other medical facilities is obtained based on extracting values from additional results of DPI of additional packets sent over communications networks of the medical facilities, in a manner explained below. Optionally, the predetermined threshold is set to a value that is greater than the average prevalence of repeated medical imaging at the multiple medical facilities.

In addition to being utilized for calculating the predetermined threshold, or instead of being used to calculate it, data from multiple medical facilities may be utilized to compare the prevalence of repeated imaging at the facility with prevalence at the other medical facilities. To this end, in one embodiment, the computer 300 receives additional packets transmitted over communication networks of multiple medical facilities, where the additional packets include data related to operations of additional medical imaging devices at the multiple facilities. The computer 300 performs DPI of the additional packets, and extracts, from results of the DPI of the additional packets, additional values indicative of medical images acquired using the additional medical imaging devices. The computer 300 identifies, based on the additional values, additional instances of repeated medical imaging (at the multiple medical facilities), and calculates, based on the additional instances, values indicative of the prevalence of repeated medical imaging at the multiple medical facilities. The computer 300 may then report a comparison between the prevalence of repeated medical imaging at the medical facility and the prevalence of repeated medical imaging at the multiple medical facilities. Optionally, the report includes an indication of a statistical significance of a hypothesis that the magnitude of the prevalence at the medical facility is greater than its prevalence at the multiple facilities, which is based on a distribution of the prevalences at the multiple facilities. For example, the report may include a p-value calculated for the prevalence of repeated imaging at the medical facility (based on the distribution) or an indication of how many standard deviations the prevalence at the medical facility is from the mean of the multiple medical facilities. In another example, the report may include an indication of a percentile of the prevalence of repeated medical imaging at medical facility based on said distribution.

The calculation of the prevalence of repeated medical imaging may be broken down (stratified) and involve calculation of values indicative of the prevalence with respect to various parameters, such as the technician performing the imaging, the type of medical device used, and/or the body part being imaged. This can help point out specific problems that might not be identified when the repeated medical imaging is evaluated at a larger scale.

In one embodiment, the computer 300 identifies, based on the results of the DPI of the packets, additional values identifying technicians who acquired medical images (e.g., based on their identifiers which are sent in some of the packets), and calculates values indicative of prevalence of repeated medical imaging by each of the technicians. Optionally, the computer 300 sends an alert (e.g., to the user interface 302) about excessive repeated medical imaging by a certain technician responsive to prevalence of repeated medical imaging by the certain technician reaching a predetermined threshold. Optionally, the alert may involve recommending additional training for the certain technician.

In another embodiment, the computer 300 identifies, based on the results of the DPI of the packets, additional values identifying body parts that were imaged, and calculates values indicative of prevalence of repeated medical imaging of different body parts. Optionally, if prevalence of repeated imaging of a certain body part reaches a threshold, the computer 300 alerts thereof (e.g., by sending a notification to the user interface 302).

In yet another embodiment, the computer 300 identifies, based on the results of the DPI of the packets, additional values that identify models of medical imaging devices that were utilized, and calculates values indicative of prevalence of repeated medical imaging when utilizing different models. Optionally, if prevalence of repeated imaging using a certain model of an imaging device reaches a threshold, the computer 300 alerts thereof (e.g., by sending a notification to the user interface 302).

It is to be noted that some embodiments of the system illustrated in FIG. 16 may be designed such that they do not interfere with operations of medical devices and/or other computer systems of the medical facility, nor may they require changes be made to the computer systems or communication networks (beyond a mechanism for capturing the packets). Therefore, in some embodiments, the packets received by the computer 300 are not transmitted in response to a query of the computer 300 to an EMR system or any other computer system of the medical facility (e.g., the PACS server 308), or in response to a communication sent by the computer 300 (i.e., the packets are transmitted because of the routine operations of the medical imaging devices 301-1 to 301-N and not because of operations performed by the computer 300). Furthermore, the computer 300 need not be an integral part of the computing infrastructure of the medical facility. In one embodiment, the computer 300 does not have access to a PACS server system to which at least some of the packets are sent. In another embodiment, the computer 300 does not have permission to access and/or command any of the medical imaging devices 301-1 to 301-N. In yet another embodiment, the computer 300 does not transmit packets over the communication network 303. In still another embodiment, the computer 300 is connected to a single networking device 304 that is connected to the communication network 303.

Figure 17:
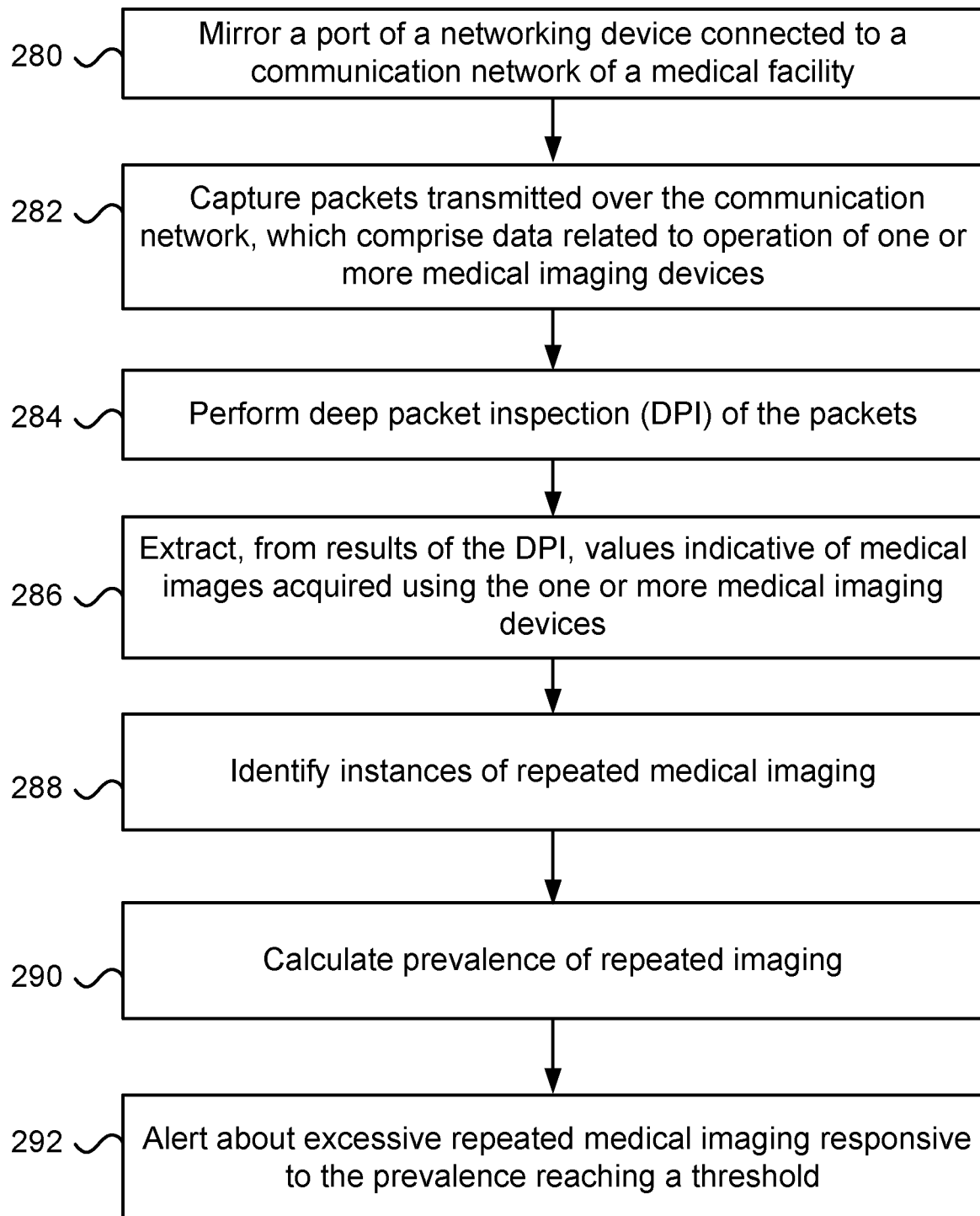
FIG. 17 illustrates steps involved in one embodiment of a method for calculating prevalence of repeated medical imaging.

FIG. 17 illustrates steps involved in one embodiment of a method for calculating prevalence of repeated medical imaging. The steps illustrated in FIG. 17 may be executed, in some embodiments, by systems modeled according to FIG. 16, as described above. In some embodiments, instructions for implementing the method may be stored on a computer-readable medium, which may optionally be a non-transitory computer-readable medium. In response to execution by a computer system including a processor and memory (e.g., the computer 300 described above), the instructions cause the computer system to perform operations of the method.

In one embodiment, the method for calculating prevalence of repeated medical imaging includes at least the following steps:

In Step 282, capturing packets transmitted over a communication network (e.g., the communication network 303), as part of communications with the one or more medical imaging devices 301-1 to 301-N. Optionally, this step may be performed through continuous monitoring and capturing of traffic sent over the communication network.

In Step 284, performing deep packet inspection (DPI) of the packets.

In Step 286, extracting, from results of the DPI, values indicative of medical images acquired using the one or more medical imaging devices. Optionally, the values include one or more of the following: patient identifiers, medical imaging device identifiers, identifiers of body parts being image, parameters used to run imaging devices, and dates and times the medical images were taken.

In Step 288, identifying, based on the values, instances of repeated images, where a repeated image involves acquiring images of the same patient and body part multiple times, utilizing a certain type of medical imaging device within a predetermined period.

And in Step 290, calculating, based on the instances, a value indicative of the prevalence of repeated medical imaging.

In some embodiments, the method may include optional Step 280, which involves receiving the packets captured in Step 282 utilizing port mirroring of a port on a networking device connected to the communication network (e.g., the packets may be received via the mirror port 306 that mirrors the port 305, as described above).

In some embodiments, the method may include optional Step 292, which involves alerting about excessive repeated medical imaging responsive to the prevalence reaching a predetermined threshold. Optionally, the method also includes a step involving calculating the predetermined threshold based on results of DPI of other packets transmitted over one or more communication networks of one or more medical facilities.

The prevalence of repeated medical imaging at the medical facility may be compared, in some embodiments, with a prevalence of repeated medical imaging at other facilities. To this end, in some embodiments, the method may optionally include the following steps: capturing additional packets transmitted over communication networks of multiple medical facilities, where the additional packets include data related to operation of additional medical imaging devices at the multiple facilities; performing DPI of the additional packets; extracting, from results of the DPI of the additional packets, additional values indicative of medical images acquired using the additional medical imaging devices; identifying, based on the additional values, additional instances of repeated medical imaging; calculating, based on the additional instances, values indicative of the prevalence of repeated medical imaging at the multiple medical facilities; and reporting a comparison between the prevalence of repeated medical imaging at the medical facility and the prevalence of repeated medical imaging at the multiple medical facilities. Optionally, the method may include a step of calculating a distribution of the prevalence of repeated medical imaging at the multiple medical facilities, and indicating a percentile of the prevalence of repeated medical imaging at medical facility based on said distribution.

In some embodiments, a calculation of the prevalence of repeated medical imaging may be broken down (stratified) and involve calculation of values indicative of the prevalence with respect to various parameters, such as the technician performing the imaging, the type of medical device used, and/or the body part being imaged.

In one embodiment, the prevalence of repeated medical imaging may be evaluated with respect to technicians who performed the imaging. Optionally, the method may include the following steps: identifying, based on the results of the DPI, additional values identifying technicians who acquired medical images, and calculating values indicative of prevalence of repeated medical imaging by each of the technicians. Optionally, the method also includes a step of alerting about excessive repeated medical imaging by a certain technician responsive to prevalence of repeated medical imaging by the certain technician reaching a predetermined threshold.

In another embodiment, the prevalence of repeated medical imaging may be evaluated with respect to body parts that were imaged. Optionally, the method may include the following steps: identifying, based on the results of the DPI, additional values identifying body parts that were imaged, and calculating values indicative of prevalence of repeated medical imaging of different body parts.

In still another embodiment, the prevalence of repeated medical imaging may be evaluated with respect to models of medical imaging devices utilized to perform the imaging. Optionally, the method may include the following steps: identifying, based on the results of the DPI, additional values that identify models of medical imaging devices that were utilized, and calculating values indicative of prevalence of repeated medical imaging when utilizing different models.

Figure 18:
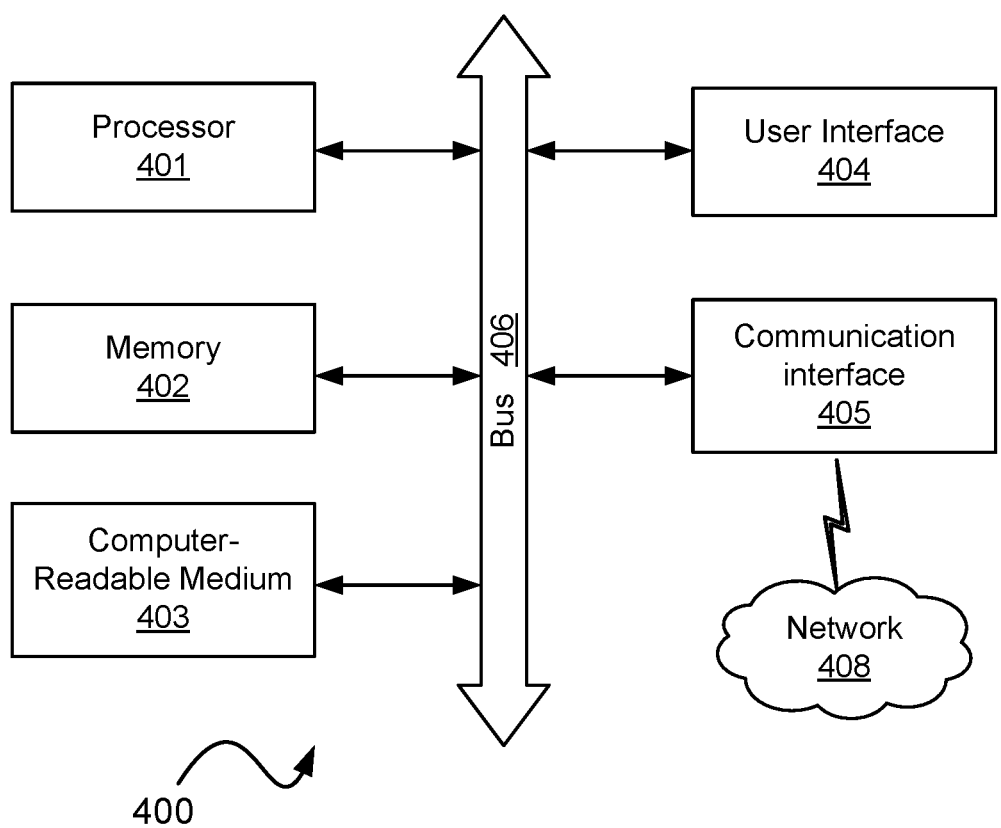
FIG. 18 is a schematic illustration of possible embodiments for a computer that is able to realize one or more of the embodiments discussed herein.

FIG. 18 is a schematic illustration of possible embodiments for a computer that is able to realize one or more of the embodiments discussed herein that include a "computer" (which may be referred to herein using different reference numerals). The computer 400 may be implemented in various ways, such as, but not limited to, a server, a client, a personal computer, a network device, and/or any other computer form capable of executing a set of computer instructions. The computer 400 includes one or more of the following components: a processor 401, memory 402, computer-readable medium 403, user interface 404, communication interface 405, and bus 406.

Herein, references to a computer or processor may include any collection of one or more computers and/or processors, which may be at different locations, that individually or jointly execute one or more sets of computer instructions. For example, reference to "a computer" may involve first computer located at a medical facility, which receives captured packets, and a second computer that is a remote server (e.g., a cloud-based device) that performs certain processing operations on the captured packets.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

References to computer-readable medium may refer to a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store, Google Play, or a repository of a hardware manufacturer (e.g., of a medical device). Optionally, the computer program may be downloaded from a repository, such as an open source and/or community run repository (e.g., GitHub).

At least some of the methods described herein that are methods implemented on a computer (also referred to as "computer-implemented methods"). Implementing these methods may involve utilizing a computer, such as the computer 400, by executing instructions on the processor 401. Additionally, at least some of these instructions may be stored on a non-transitory computer-readable medium.

As used herein, references to "one embodiment" (and its variations) mean that the feature being referred to may be included in at least one embodiment of the invention. Moreover, separate references to "one embodiment", "some embodiments", "another embodiment", "other embodiments", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal when X did not happen.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise.

The phrase "based on" is intended to mean "based, at least in part, on". Additionally, stating that a value is calculated "based on X", and following that, in a certain embodiment, that the value is calculated "also based on Y", means that in the certain embodiment the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the inventions described herein may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to audit reported amounts of infused medications, comprising:
a computer configured to:
receive packets captured from transmissions sent over a communication network, wherein the packets comprise data related to activity of infusion pump systems, sent to be stored in an electronic medical record system (EMR system) of a medical facility, and not in response to a communication sent by the computer;
perform deep packet inspection of the packets;
determine, based on results of the deep packet inspection, a type of the infusion pump systems;
utilize a predetermined payload format, used by devices of the type of the infusion pump systems, to extract from the packets values comprising dosages of medications delivered to patients during treatment sessions using the infusion pump systems;
calculate, based on the values, actual amounts, which are amounts of the medications that were provided to the patients during the treatment sessions;
receive reported amounts, which are amounts of the medications reported as being provided to the patients during the treatment sessions; and
forward a result of a comparison between the actual amounts and the reported amounts.

2. The system of claim 1, wherein the computer is further configured to: receive additional packets that were transmitted over communication networks of multiple medical facilities, wherein the additional packets comprise data related to activity of additional infusion pump systems; perform deep packet inspection of the additional packets; extract, from results of the deep packet inspection of the additional packets, additional values comprising dosages of medications delivered to additional patients during additional treatment sessions using the additional infusion pump systems; calculate, based on the additional values, additional actual amounts, which are amounts of the medications that were provided to the additional patients during the additional treatment sessions; receive additional reported amounts, which are amounts of the medications reported as being provided to the patients during the additional treatment sessions; and report a comparison between (i) a magnitude of a difference between the actual amounts and the reported amounts, and (ii) magnitudes of differences between the additional actual amounts and the additional reported amounts.

3. The system of claim 2, wherein the computer is further configured to report a comparison between (i) a magnitude of a difference between the actual amounts and the reported amounts for a certain care area and (ii) magnitudes of differences between the additional actual amounts and the additional reported amounts for the certain care area at the multiple medical facilities.

4. The system of claim 1, wherein the computer is further configured to: receive additional packets that were transmitted over communication networks of multiple medical facilities, wherein the additional packets comprise data related to activity of additional infusion pump systems; perform deep packet inspection of the additional packets; extract, from results of the deep packet inspection of the additional packets, additional values comprising dosages of a certain medication delivered to additional patients during additional treatment sessions using the additional infusion pump systems; calculate, based on the additional values, additional actual amounts, which are amounts of the certain medication that were provided to the additional patients during the additional treatment sessions; receive additional reported amounts, which are amounts of the medications reported as being provided to the patients during the additional treatment sessions; and report a comparison between (i) a magnitude of a difference between an amount of the certain medication provided to the patients during the treatment sessions and an amount of the certain medication reported as being provided to the patients during the treatment sessions, and (ii) magnitudes of differences between the additional actual amounts and the additional reported amounts.

5. The system of claim 1, wherein the computer is further configured to calculate the reported amounts based on indications of changes in amounts of the medications in an inventory of the medical facility, which were received from a computer system having access to state information of said inventory.

6. The system of claim 1, wherein the communication network comprises a networking device that has a mirror port that is configured to duplicate the packets, which are transmitted over the communication network; and wherein the computer is connected to the mirror port and is configured to receive the packets via the mirror port.

7. The system of claim 1, wherein the computer is further configured to: extract, from the results of the deep packet inspection, indications of care areas at which the treatments sessions were conducted; calculate, based on the values and the indications, actual care area amounts, which are amounts of the medications that were provided to patients during the treatment sessions at each of the care areas; receive reported care area amounts, which are amounts of the medications reported as being provided to the patients during the treatment sessions in each care area; and forward a result of a comparison between the actual care area amounts and the reported care area amounts.

8. The system of claim 1, wherein the computer is further configured to: extract, from the results of the deep packet inspection, identities of caregivers that administered the treatment sessions; calculate, based on the values and the identities, actual caregiver amounts, which are amounts of the medications that were provided to patients during the treatment sessions by each of the caregivers; receive reported caregiver amounts, which are amounts of the medications reported as being provided to the patients during the treatment sessions administered by each of the caregivers; and forward a result of a comparison between the actual caregiver amounts and the reported caregiver amounts.

9. The system of claim 1, wherein the computer does not have access to an EMR system to which at least some of the packets are sent.

10. The system of claim 1, wherein the computer does not have permission to access and/or command any of the infusion pump systems.

11. The system of claim 1, wherein the computer does not transmit packets over the communication network.

12. The system of claim 1, wherein the computer is connected to a single networking device that is connected to the communication network.

13. A method for auditing reported amounts of infused medications, comprising:
receiving, by a computer, packets captured from transmissions sent over a communication network, wherein the packets comprise data related to operation of infusion pump systems, sent to be stored in an electronic medical record system (EMR system) of a medical facility, and not in response to a communication sent by the computer;
performing deep packet inspection of the packets;
determining, based on results of the deep packet inspection, a type of the infusion pump systems;
utilizing a predetermined payload format used by devices of the type of the infusion pump systems, to extract from the packets values comprising dosages of medications delivered to patients during treatment sessions using the infusion pump systems;
calculating, based on the values, actual amounts, which are amounts of the medications that were provided to the patients during the treatment sessions;
receiving reported amounts, which are amounts of the medications reported as being provided to the patients during the treatment sessions; and
forwarding a result of a comparison between the actual amounts and the reported amounts.

14. The method of claim 13, further comprising: extracting, from the results of the deep packet inspection, indications of care areas at which the treatments sessions were conducted; calculating, based on the values and the indications, actual care area amounts, which are amounts of the medications that were provided to patients during the treatment sessions at each of the care areas; receiving reported care area amounts, which are amounts of the medications reported as being provided to the patients during the treatment sessions in each care area; and forwarding a result of a comparison between the actual care area amounts and the reported care area amounts.

15. The method of claim 13, further comprising: extracting, from the results of the deep packet inspection, identities of caregivers that administered the treatment sessions; calculating, based on the values and the identities, actual caregiver amounts, which are amounts of the medications that were provided to patients during the treatment sessions by each of the caregivers; receiving reported caregiver amounts, which are amounts of the medications reported as being provided to the patients during the treatment sessions administered by each of the caregivers; and forwarding a result of a comparison between the actual caregiver amounts and the reported caregiver amounts.

16. The method of claim 13, further comprising: capturing additional packets transmitted over communication networks of multiple medical facilities, wherein the additional packets comprise data related to activity of additional infusion pump systems; performing deep packet inspection of the additional packets; extracting, from results of the deep packet inspection of the additional packets, additional values comprising dosages of medications delivered to additional patients during additional treatment sessions using the additional infusion pump systems; calculating, based on the additional values, additional actual amounts, which are amounts of the medications that were provided to the additional patients during the additional treatment sessions; receiving additional reported amounts, which are amounts of the medications reported as being provided to the patients during the additional treatment sessions; and reporting a comparison between (i) a magnitude of a difference between the actual amounts and the reported amounts and (ii) magnitudes of differences between the additional actual amounts and the additional reported amounts.

17. The method of claim 13, further comprising: capturing additional packets transmitted over communication networks of multiple medical facilities, wherein the additional packets comprise data related to activity of additional infusion pump systems; performing deep packet inspection of the additional packets; extracting, from results of the deep packet inspection of the additional packets, additional values comprising dosages of a certain medication delivered to additional patients during additional treatment sessions using the additional infusion pump systems; calculating, based on the additional values, additional actual amounts, which are amounts of the certain medication that were provided to the additional patients during the additional treatment sessions; receiving additional reported amounts, which are amounts of the medications reported as being provided to the patients during the additional treatment sessions; and reporting a comparison between (i) a magnitude of a difference between amount of the certain medication provided to the patients during the treatment sessions and amount of the certain medication reported as being provided to the patients during the treatment sessions, and (ii) magnitudes of differences between the additional actual amounts and the additional reported amounts.

18. The method of claim 13, further comprising calculating the reported amounts based on indications of changes in amounts of the medications in an inventory of the medical facility, which were received from a computer system having access to state information of said inventory.

19. The method of claim 13, further comprising receiving at least some of the packets utilizing port mirroring of a port on a networking device connected to a communication network.

20. A non-transitory computer-readable medium having instructions stored thereon that, in response to execution by a system including a processor and memory, causes the system to perform operations comprising:

receiving, by a computer, packets transmitted over a communication network, wherein the packets comprise data related to operation of infusion pump systems, sent to be stored in an electronic medical record system (EMR system) of a medical facility, and not in response to a communication sent by the computer;

performing deep packet inspection of the packets;

determining based on results of the deep packet inspection, a type of the infusion pump systems;

utilizing a predetermined payload format, used by devices of the type of the infusion pump systems, to extract from the packets values comprising dosages of medications delivered to patients during treatment sessions using the infusion pump systems;

calculating, based on the values, actual amounts, which are amounts of the medications that were provided to the patients during the treatment sessions;

receiving reported amounts, which are amounts of the medications reported as being provided to the patients during the treatment sessions; and forwarding a result of a comparison between the actual amounts and the reported amounts.

* * * * *